(12) United States Patent
Scarselli et al.

(10) Patent No.: US 8,017,387 B2
(45) Date of Patent: Sep. 13, 2011

(54) TELOMERASE REVERSE TRANSCRIPTASE FUSION PROTEIN, NUCLEOTIDES ENCODING IT, AND USES THEREOF

(75) Inventors: Elisa Scarselli, Rome (IT); Carmela Mennuni, Rome (IT); Nicola La Monica, Rome (IT); Gennaro Ciliberto, Rome (IT)

(73) Assignee: Istituto di Ricerche di Biologia Molecolare P. Angeletti SpA, Rome (IT)

( * ) Notice: Subject to any disclaimer, the term of this patent is extended or adjusted under 35 U.S.C. 154(b) by 700 days.

(21) Appl. No.: 11/974,067

(22) Filed: Oct. 11, 2007

(65) Prior Publication Data
US 2008/0090778 A1    Apr. 17, 2008

Related U.S. Application Data

(60) Provisional application No. 60/851,183, filed on Oct. 12, 2006.

(51) Int. Cl.
*C12N 15/00* (2006.01)
*C12N 5/10* (2006.01)

(52) U.S. Cl. ............... 435/320.1; 435/252.3; 435/325; 435/455; 435/457; 435/471; 424/93.2; 536/23.1; 536/23.4; 536/23.71

(58) Field of Classification Search .............. 435/320.1, 435/252.3, 325, 455, 456, 471; 424/93.2; 536/23.1, 23.4, 23, 71
See application file for complete search history.

(56) References Cited

U.S. PATENT DOCUMENTS

| | | | |
|---|---|---|---|
| 5,241,053 A | 8/1993 | Fujisawa et al. | |
| 6,166,178 A | 12/2000 | Cech et al. | |
| 6,261,836 B1 | 7/2001 | Cech et al. | |
| 6,413,523 B1 | 7/2002 | Clements | |
| 6,927,285 B2 | 8/2005 | Cech et al. | |
| 7,262,288 B1 | 8/2007 | Cech et al. | |
| 2003/0044421 A1 | 3/2003 | Emini et al. | |
| 2003/0096344 A1 | 5/2003 | Cech et al. | |
| 2004/0242529 A1 | 12/2004 | Cech et al. | |
| 2004/0247615 A1 | 12/2004 | Emini et al. | |

FOREIGN PATENT DOCUMENTS

| | | |
|---|---|---|
| WO | WO 86/00647 A1 | 1/1986 |
| WO | WO 90/06366 A1 | 6/1990 |
| WO | WO 98/37181 A2 | 8/1998 |
| WO | WO 98/42375 A1 | 10/1998 |
| WO | WO 98/59040 A2 | 12/1998 |
| WO | WO 99/26654 A1 | 6/1999 |
| WO | WO 2004/002408 A2 | 1/2004 |
| WO | WO 2005/077977 A2 | 8/2005 |
| WO | WO 2006/008154 * | 1/2006 |
| WO | WO 2006/011151 A2 | 2/2006 |
| WO | WO 2006/123155 A2 | 11/2006 |

OTHER PUBLICATIONS

Shiver et al., Replication-incompetent adenoviral vaccine vector elicits effective anti-immunodeficiency-virus immunity Nature 415, 331-335 (Jan. 17, 2002).*
Poole et al., Review Activity, function, and gene regulation of the catalytic subunit of telomerase (hTERT) Gene vol. 269, Issues 1-2, May 16, 2001, pp. 1-12.*
Rudinger (in Peptide Hormones, Parsons (ed.), University Park Press: Baltimore, MD, pp. 1-7, 1976.*
Voet et al Biochemistry, John Wiley and Sons, 1990, pp. 126-128.*
Ngo, in the Protein Folding Problem and Tertiary Structure Prediction, Merz et al. pp. 492-506).*
Kimchi-Sarfaty et al., 2007, Science, pp. 525-528.*
Arai, K. et al. "Two independent Regions of Human Telomerase Reverse Transcriptase Are Important for Its Oligomerization and Telomerase Activity", The Journal of Biological Chemistry, 2002, vol. 277, pp. 8538-8544.
Danthinne, X. et al. "Production of first generation adenovirus vectors: a review", Gene Therapy, 2000, Vol. 7, pp. 1707-1714.
Dupont, J. et al. "Artificial Antigen-Presenting Cells Transduced with Telomerase Efficiently Expand Epitope-Specific, Human Leukocyte Antigen-Restricted Cytotoxic T Cells", Cancer Research, 2005, vol. 65, pp. 5417-5427.
Fingerut, E. et al. "Vaccine and adjuvant activity of recombinant subunit B of *E. coli* enterotoxin produced in yeast", Vaccine, 2005, vol. 23, pp. 4685-4696.
Graham, F. "Adenovirus vectors for high-efficiency gene transfer into mammalian cells", Trends Immunology Today, 2000, vol. 21, pp. 426-428.
Haddad, D. et al. "Comparative study of DNA-based immunization vectors: effect of secretion signals on the antibody responses in mice", FEMS Immunology and Medical Microbiology, 1997, vol. 18, pp. 193-202.
Kilian, A. et al. "Isolation of a candidate human telomerase catalytic subunit gene, which reveals complex splicing patterns in different cell types", Human Molecular Genetics, 1997, vol. 6, pp. 2011-2019.

(Continued)

*Primary Examiner* — Maria Leavitt
(74) *Attorney, Agent, or Firm* — Alysia A. Finnegan; Sheldon O. Heber

(57) ABSTRACT

Polynucleotides encoding telomerase reverse transcriptase (TERT) fusion proteins are provided, the TERT fusion proteins comprising a TERT protein, or functional variant thereof, fused to a substantial portion of the B subunit of heat labile enterotoxin (LTB). TERT variants useful in TERT-LTB fusion proteins of the invention comprise mutations that function to eliminate telomerase catalytic activity. The polynucleotides of the present invention can elicit an immune response in a mammal, which, in preferred embodiments, is stronger than the immune response elicited by a wild-type TERT. TERT expression is commonly associated with the development of human carcinomas. The present invention provides compositions and methods to elicit or enhance immunity to the protein product expressed by the TERT tumor-associated antigen, wherein aberrant TERT expression is associated with a carcinoma or its development. This invention specifically provides adenoviral vector and plasmid constructs carrying polynucleotides encoding TERT fusion proteins and TERT variants and discloses their use in vaccines and pharmaceutical compositions for preventing and treating cancer.

5 Claims, 24 Drawing Sheets

OTHER PUBLICATIONS

Kim, N. et al. "Specific Association of Human Telomerase Activity with Immortal Cells and Cancer", Science, 1994, vol. 266, pp. 2011-2015.

Lathe, R. "Sythetic Oligonucleotide Probes Deduced from Amino Acid Sequence Data Theoretical and Practical Considerations", Journal of Molecular Biology, 1985, vol. 183, pp. 1-12.

Meyerson, M. et al. "*hEST2*, the Putative Human Telomerase Catalytic Subunit Gene, Is Up-Regulated in Tumor Cells and during Immortalization", Cell, 1997, vol. 90, pp. 785-795.

Nakamura, T. et al. "Telomerase Catalytic Subunit Homologs from Fission Yeast and Human", Science, 1997, vol. 277, pp. 955-959.

Patel, K. et al. "Telomerase as a tumor-associated antigen for cancer immunotherapy", Cytotechnology, 2004, vol. 45, pp. 91-99.

Rigano, M. et al. "Production of a fusion protein consisting of the enterotoxigenic *Escherichia coli* heat-labile toxin B subunit and a tuberculosis antigen in *Arabidopsis thaliana*", Plant Cell Reports, 2004, vol. 22, pp. 502-508.

Simmons, C. et al. "Immunomodulation Using Bacterial Enterotoxins", Scandinavian Journal of Immunology, 2001, vol. 53, pp. 218-226.

\* cited by examiner

```
       M   D   A       M   K   R       G   L   C       C   V   L       L   L   C       G   A   V       F   V   S       P   S   E
  1  ATGGATGCA ATGAAGAGG GGCCTGTGC TGCGTGCTG CTGCTGTGT GGCGCCGTG TTTGTGAGC CCTAGCGAG
       I   P   R       A   P   R       C   R   A       V   R   S       L   L   R       S   H   Y       R   E   V       L   P   L
 73  ATCCCCAGA GCCCCCAGA TGCAGAGCC GTGCGGAGC CTGCTGCGG AGCCACTAC CGGGAAGTG CTGCCCCTG
       A   T   F       V   R   R       L   G   P       Q   G   W       R   L   V       Q   R   G       D   P   A       A   F   R
145  GCCACCTTC GTGCGGCGG CTGGGCCCC CAGGGCTGG CGGCTGGTG CAGCGGGGC GACCCTGCC GCCTTCCGG
       A   L   V       A   Q   C       L   V   C       V   P   W       D   A   R       P   P   P       A   A   P       S   F   R
217  GCCCTGGTG GCTCAGTGC CTGGTGTGC GTGCCCTGG GACGCCAGA CCCCCCCCA GCCGCCCCT AGCTTCCGG
       Q   V   S       C   L   K       E   L   V       A   R   V       L   Q   R       L   C   E       R   G   A       K   N   V
289  CAGGTGAGC TGCCTGAAG GAACTGGTG GCCAGAGTG CTGCAGCGG CTGTGCGAG AGAGGCGCC AAGAACGTG
       L   A   F       G   F   A       L   L   D       G   A   R       G   G   P       P   E   A       F   T   T       S   V   R
361  CTGGCCTTC GGCTTCGCC CTGCTGGAC GGCGCCAGA GGCGGGCCT CCCGAGGCC TTCACCACA AGCGTGCGG
       S   Y   L       P   N   T       V   T   D       A   L   R       G   S   G       A   W   G       L   L   L       R   R   V
433  AGCTACCTG CCCAACACC GTGACCGAC GCCCTGCGG GGCAGCGGC GCCTGGGGC CTGCTGCTG AGAAGAGTG
       G   D   D       V   L   V       H   L   L       A   R   C       A   L   F       V   L   V       A   P   S       C   A   Y
505  GGGGACGAC GTGCTGGTG CACCTGCTG GCCCGGTGC GCCCTGTTC GTGCTGGTG GCCCCCAGC TGCGCCTAC
       Q   V   C       G   P   P       L   Y   Q       L   G   A       A   T   Q       A   R   P       P   P   H       A   S   G
577  CAGGTGTGC GGCCCCCAC CCCGAGGCC CTGTACCAG CTGGGAGCC GCCACCCAG GCCAGGCCC CCACCCCAC GCCAGCGGC
       P   R   R       R   L   G       C   E   R       A   W   N       H   S   V       R   E   A       G   V   P       L   G   L
649  CCCAGACGG AGACTGGGC TGCGAGCGG GCCTGGAAC CACAGCGTG AGAGAGGCC GGCGTGCCC CTGGGCCTG
       P   A   P       G   A   R       R   R   G       G   S   A       S   R   S       L   P   L       P   K   R       P   R   R
721  CCAGCCCCT GGCGCCAGA AGAAGAGGC GGCAGCGCC AGCCGGAGC CTGCCCCTG CCCAAGCGG CCCAGAAGA
       G   A   A       P   E   P       E   R   T       P   V   G       Q   G   S       W   A   H       P   G   R       T   R   G
793  GGCGCTGCC CCCGAGCCC GAGCGGACC CCCGTGGGC CAGGGCAGC TGGGCCCAC CCCGGCAGA ACCAGAGGC
       P   S   D       R   G   F       C   V   V       S   P   A       R   P   A       E   E   A       T   S   L       E   G   A
865  CCCAGCGAC CGGGGCTTC TGCGTGGTG AGCCCCGCC AGACCCGCC GAGGAGGCC ACAAGCCTG GAGGGCGCC
       L   S   G       T   R   H       S   H   P       S   V   G       R   Q   H       H   A   G       P   P   S       T   S   R
937  CTGAGCGGC ACCCGGCAC AGCCACCCC AGCGTGGGG CGGCAGCAC CACGCCGGA CCCCCCAGC ACCAGCAGA
```

FIG.1A

```
     P P R   P W D   T P C   P P V   Y A E   T K H   F L Y   S S G
1009 CCCCCAGA CCCTGGGAC ACCCCCTGC CCCCCTGTG TACGCCGAG ACCAAGCAC TTCCTGTAC AGCAGCGGC
     D K E   Q L R   P S F   L L S   S L R   P S L   T G A   R R L
1081 GACAAGGAG CAGCTGCGG CCCAGCTTC CTGCTGAGC AGCCTGAGA CCCAGCCTG ACCGGCGCC AGGAGACTG
     V E T   I F L   G S R   P W M   P G T   P R R   L P R   L P Q
1153 GTGGAGACC ATCTTCCTG GGCAGCCGG CCCTGGATG CCCGGCACC CCCCGGAGA CTGCCCCGG CTGCCCCAG
     R Y W   Q M R   P L F   L E L   L G N   H A Q   C P Y   G V L
1225 CGGTACTGG CAGATGCGG CCCCTGTTC CTGGAGCTG CTGGGCAAC CACGCCCAG TGCCCCTAC GGCGTGCTG
     L K T   H C P   L R A   A V T   P A A   G V C   A R E   K P Q
1297 CTGAAAACC CACTGCCCC CTGAGAGCC GCCGTGACC CCCGCTGCC GGCGTGTGC GCCAGAGAG AAGCCCCAG
     G S V   A A P   E E E   D T D   P R R   L V Q   L L R   Q H S
1369 GGCAGCGTG GCCGCTCCC GAGGAGGAG GACACCGAC CCCAGACGC CTGGTGCAG CTGCTGCGG CAGCACAGC
     S P W   Q V Y   G F V   R A C   L R R   L V P   P G L   W G S
1441 AGCCCTTGG CAGGTGTAC GGCTTCGTG CGGGCCTGC CTGAGAAGG CTGGTGCCC CCTGGCCTG TGGGGCAGC
     R H N   E R R   F L R   N T K   K F I   S L G   K H A   K L S
1513 AGACACAAC GAGCGGCGG TTCCTGCGG AACACCAAG AAGTTCATC AGCCTGGGG AAGCACGCC AAGCTGAGC
     L Q E   L T W   K M S   V R D   C A W   L R R   S P G   V G C
1585 CTGCAGGAA CTGACCTGG AAGATGAGC GTGCGGGAC TGCGCCTGG CTGCGGCGG AGCCCTGGC GTGGGCTGC
     V P A   A E H   R L R   E E I   L A K   F L H   W L M   S V Y
1657 GTGCCAGCC GCCGAGCAC CGGCTGCGG GAGGAGATC CTGGCCAAG TTCCTGCAC TGGCTGATG AGCGTGTAC
     V V E   L L R   S F F   Y V T   E T T   F Q K   N R L   F F Y
1729 GTGGTGGAA CTGCTGCGG TCCTTCTTC TACGTGACC GAAACCACC TTCCAGAAG AACCGGCTG TTCTTCTAC
     R K S   V W S   K L Q   S I G   I R Q   H L K   R V Q   L R E
1801 CGGAAGAGC GTGTGGAGC AAGCTGCAG AGCATCGGC ATCAGGCAG CACCTGAAG AGAGTGCAG CTGCGGGAG
     L S E   A E V   L L R   R Q H   R E A   R P A   L L T   S R L   R F I
1873 CTGAGCGAG GCCGAAGTG CTGCTGCGG AGACAGCAC CGGGAGGCC AGACCTGCC CTGCTGACC AGCCGGCTG CGGTTCATC
     P K P   D G L   R P I   V N M   D Y V   V G A   R T F   R R E
1945 CCCAAGCCC GACGGCCTG CGGCCCATC GTGAACATG GACTACGTG GTGGGCGCC AGAACCTTC CGGCGGGAG
```

FIG. 1B

```
            K   R   A       E   R   L       T   S   R       V   K   A       L   F   S       V   L   N       Y   E   R       A   R   R
2017  AAGCGGGCC GAGCGGCTG ACCAGCAGA GTGAAGGCC CTGTTCAGC GTGCTGAAC TACGAGCGG GCCAGGAGA
        P   G   L       L   G   A       S   V   L       G   L   D       D   I   H       R   A   W       R   T   F       V   L   R
2089  CCCGGCCTG CTGGGCGCC AGCGTGCTG GGCCTGGAC GACATCCAC CGGGCCTGG CGGACCTTC GTGCTGAGA
        V   R   A       Q   D   P       P   P   E       L   Y   F       V   K   V       A   I   T       G   A   Y       D   T   I
2161  GTGCGGGCC CAGGACCCC CCACCCGAG CTGTACTTC GTGAAAGTG GCCATCACC GGCGCCTAC GACACCATC
        P   Q   D       R   L   T       E   V   I       A   S   I       I   K   P       Q   N   T       Y   C   V       R   R   Y
2233  CCCCAGGAC CGGCTGACC GAAGTGATC GCCAGCATC ATCAAGCCC CAGAACACC TACTGCGTG CGGCGGTAC
        A   V   V       Q   K   A       A   H   G       H   V   R       K   A   F       K   S   H       V   S   T       L   T   D
2305  GCCGTGGTG CAGAAGGCC GCCCACGGC CACGTGCGG AAGGCCTTC AAGAGCCAC GTGAGCACC CTGACCGAC
        L   Q   P       Y   M   R       Q   F   V       A   H   L       Q   E   T       S   P   L       R   D   A       V   V   I
2377  CTGCAGCCC TACATGCGG CAGTTCGTG GCCCACCTG CAGGAGACC AGCCCCCTG CGGGATGCC GTGGTGATC
        E   Q   S       S   S   L       N   E   A       S   S   G       L   F   D       V   F   L       R   F   M       C   H   H
2449  GAGCAGAGC AGCAGCCTG AACGAGGCC AGCAGCGGC CTGTTCGAC GTGTTCCTG CGCTTCATG TGCCACCAC
        A   V   R       I   R   G       K   S   Y       V   Q   C       Q   G   I       P   Q   G       S   I   L       S   T   L
2521  GCCGTGCGG ATCCGGGGC AAGAGCTAC GTGCAGTGC CAGGGCATC CCTCAGGGC AGCATCCTG AGCACACTG
        L   C   S       L   C   Y       G   D   M       E   N   K       L   F   A       G   I   R       R   D   G       L   L   L
2593  CTGTGCTCT CTGTGCTAC GGCGACATG GAGAACAAG CTGTTCGCC GGCATCCGG CGGGACGGA CTGCTGCTG
        R   L   V       D   D   F       L   L   V       T   P   H       L   T   H       A   K   T       F   L   R       T   L   V
2665  CGGCTGGTG GACGACTTC CTGCTGGTG ACCCCTCAC CTGACCCAC GCCAAGACC TTCCTGCGG ACCCTGGTG
        R   G   V       P   E   Y       P   E   Y       V   N   L       R   K   T       V   V   N       F   P   V       E   D   E
2737  CGGGGCGTG CCCGAGTAC CCCGAGTAC GTGAACCTG CGCAAGACC GTGTTGAAC TTCCCCGTG GAGGACGAG
        A   L   G       T   A       M   P   A       H   G   L       F   P   W       C   G   L       L   L   D
2809  GCCCTGGGC GGCACAGTG TTCGTGCAG ATGCCCGCC CATGGCCTG TTCCCTTGG TGCGGGCTG CTGCTGGAC
        T   R   T       L   E   V       Q   S   D       Y   S   S       Y   A   R       T   S   I       R   A   S       L   T   F
2881  ACCCGGACC CTGGAAGTG CAGAGCGAC TACAGCAGC TACGCCAGC ACCAGCATC CGGGCCAGC CTGACATTC
        N   R   G       F   K   A       G   R   N       M   R   R       K   L   F       G   V   L       R   L   K       C   H   S
2953  AACCGGGGC TTCAAGGCC GGCAGAAAC ATGCGGCGG AAGCTGTTT GGCGTGCTG CGGCTGAAG TGCCACAGC
```

FIG.1C

```
              L   F   L       D   L   Q       V   N   S       L   Q   T       V   C   T       N   I   Y       K   I   L       L   L   Q
3025  CTGTTTCTG GACCTGCAG GTGAACAGC CTGCAGACC GTGTGCACC AACATCTAC AAGATCCTG CTGCTGCAG
              A   Y   R       F   H   A       C   V   L       Q   L   P       F   H   Q       Q   V   W       K   N   P       T   F   F
3097  GCCTACCGG TTCCACGCC TGCGTGCTG CAGCTGCCC TTCCATCAG CAGGTGTGG AAGAACCCC ACCTTCTTC
              L   R   V       I   S   D       T   A   S       L   C   Y       S   I   L       K   A   K       N   A   G       M   S   L
3169  CTGCGCGTG ATCTCTGAC ACCGCCAGC CTGTGCTAC AGCATTCTG AAGGCCAAG AACGCCGGC ATGAGCCTG
              G   A   K       G   A   A       G   P   L       P   S   E       A   V   Q       W   L   C       H   Q   A       F   L   L
3241  GGGGCCAAG GGCGCTGCC GGACCCCTG CCCAGCGAG GCCGTGCAG TGGCTGTGT CACCAGGCC TTTCTGCTG
              K   L   T       R   H   R       V   T   Y       P   L       G   S       L   R   T       A   Q   T       Q   L   S
3313  AAGCTGACC CGGCACCGC GTGACCTAC CCCCTGGGA AGCCTGAGA ACCCAGACC CAGCTGAGC
              R   K   L       P   G   T       T   L   T       A   L   E       A   A   A       N   P   A       L   P   S       D   F   K
3385  CGGAAGCTG CCTGGCACC ACCCTGACA GCCCTGGAG GCCGCTGCC AACCCCGCC CTGCCTAGC GACTTCAAG
              T   I   L       D   S   R       A   P   Q       S   I   T       E   L   C       S   E   Y       R   N   T       Q   I   Y
3457  ACCATCCTG GACTCTAGA GCCCCTCAG AGCATCACC GAGCTGTGC AGCGAGTAC CGGAACACC CAGATTTAC
              T   I   N       D   K   I       L   S   Y       T   E   S       M   A   G       K   R   E       M   V   I       T   F
3529  ACCATCAAC GACAAGATC CTGAGCTAC ACCGAGTCT ATGGCCGGC AAGAGAGAA ATGGTGATC ATCACCTTC
              K   S   G       A   T   F       Q   V   E       V   P   G       S   Q   H       I   D   S       Q   K   K       A   I   E
3601  AAGAGCGGC GCCACCTTT CAGGTGGAA GTGCCTGGC AGCCAGCAC ATCGACAGC CAGAAGAAG GCCATCGAG
              R   M   K       D   T   L       R   I   T       Y   L   T       E   T   K       I   D   K       L   C   V       W   N   N
3673  CGGATGAAG GACACCCTG CGGATCACC TACCTGACC GAGACCAAG ATCGACAAG CTGTGTGTG TGGAACAAC
              K   T   P       N   S   I       A   A   I       S   M   E       N (SEQ ID NO:2)
3745  AAGACCCCC AACAGCATC GCCGCCATC TCTATGGAG AAC (SEQ ID NO:1)

FIG. 1D
```

```
  M   D   A   M   K   R   G   L   C   C   V   L   L   L   C   G   A   V   F   V   S   P   S   E
1 ATGGATGCA ATGAAGAGG GGCCTGTGC TGCGTGCTG CTGCTGTGT GGGGCCGTG TTTGTGAGC CCTAGCGAG
  I   T   R   A   P   R   C   P   A   V   R   S   L   L   R   S   R   Y   R   E   V   W   P   L
73 ATCACCAGA GCCCCCAGA TGCCCTGCC GTGAGAAGC CTGCTGCGG AGCCGGTAC AGAGAAGTG TGGCCCCTG
  A   T   F   V   R   R   L   G   P   E   G   R   L   V   Q   P   G   D   P   K   I   Y   R
145 GCCACCTTT GTGAGGAGA CTGGGCCCT GAGGGCAGG AGACTGGTG CAGCCTGGC GACCCCAAA ATCTACAGG
  T   L   V   A   Q   C   L   V   C   M   H   W   G   S   Q   P   P   P   A   D   L   S   F   H
217 ACCCTGGTG GCCCAGTGT CTGGTGTGT ATGCACTGG GGCAGCCAG CCCCCTCCC GCCGACCTG AGCTTCCAC
  Q   V   S   L   K   E   L   V   A   R   V   Q   R   L   C   E   R   N   E   R   N   V
289 CAGGTGTCC AGCCTGAAG GAACTGGTG GCCAGAGTG CAGCGGCTG TGTGAGAGA CGGAACGAG AGAAACGTG
  L   A   F   G   F   E   L   L   N   E   A   R   G   G   P   P   M   A   F   T   S   S   V   R
361 CTGGCCTTC GGCTTCGAG CTGCTGAAC GAGGCCAGA GGCGGGCCT CCCATGGCC TTCACCAGC TCTGTGAGG
  S   Y   L   P   N   T   V   I   E   T   L   R   V   S   G   A   W   M   L   L   L   S   R   V
433 AGCTACCTG CCCAACACC GTGATCGAG ACCCTGAGA GTGAGCGGC GCCTGGATG CTGCTGCTG AGCAGAGTG
  G   D   D   L   L   V   Y   L   L   A   H   C   A   L   Y   L   V   P   P   S   C   A   Y
505 GGCGATGAC CTGCTGGTG TACCTGCTG GCCCACTGC GCCCTGTAT CTGGTGCCT CCCCCAGC TGCGCCTAC
  Q   V   C   G   S   P   L   Y   Q   I   C   A   T   T   D   I   W   P   S   V   S   A   S   Y
577 CAGGTGTGC GGATCCCCC CTGTACCAG ATTTGCGCC ACCACCGAC ATCTGGCCC AGCGTGTTT GCCAGCTAC
  R   P   T   R   P   V   G   R   N   F   T   N   L   R   F   L   Q   Q   I   K   S   S   S   R
649 AGACCCACC AGACCCGTG GGCCGGAAC TTCACCAAC CTGCGGTTC CTGCAGCAG ATCAAGAGC AGCAGCAGA
  Q   E   A   P   K   P   L   A   L   P   S   R   G   T   K   R   H   L   S   L   T   S   T   S
721 CAGGAGGCC CCCAAGCCC CTGGCCCTG CCCAGCAGA GGCACCAAG AGACACCTG AGCCTGACC AGCACCAGC
  V   P   S   A   K   K   A   R   C   Y   P   V   P   R   V   E   E   G   P   H   R   Q   V   L
793 GTGCCCAGC GCCAAGAAA GCCAGATGC TACCCCGTG CCCAGAGTG GAGGAGGGC CCTCACAGA CAGGTGCTG
  P   T   P   S   G   K   S   W   V   P   S   P   A   R   S   P   E   V   P   T   A   E   K   D
865 CCCACCCCC AGCGGCAAG AGCTGGGTG CCCAGCCCC GCCAGAAGC CCCGAAGTG CCCACCGCC GAGAAGGAC
  L   S   S   K   G   K   V   S   D   L   S   L   S   G   S   V   C   C   K   H   K   P   S   S
937 CTGTCTCTG AAGGGCAAA GTGAGCGAC CTGTCTCTG AGCGGCAGC GTGTGTTGC AAGCACAAG CCCAGCAGC
```

FIG.2A

```
       T  S  L     L  S  P     P  R  Q     N  A  F     Q  L  R     P  F  I     E  T  R     H  F  L
1009 ACCAGCCTG CTGAGCCCC CCAGACAG AACGCCTTC CAGCTGAGG CCTTTCATC GAGACCCGG CACTTCCTG
       Y  S  R     G  D  G     Q  E  R     L  N  P     S  F  L     L  S  N     L  Q  P     N  L  T
1081 TACAGCAGA GGCGATGGC CAGGAGAGA CTGAACCCC AGCTTCCTG CTGAGCAAC CTGCAGCCT AACCTGACC
       G  A  R     L  V     E  I  I     F  L  G     S  R  P     R  T  S     G  P  L     C  R  T
1153 GGGGCCAGA CGCCTGGTG GAGATCATC TTCCTGGGC AGCAGACCC AGAACCAGC GGCCCTCTG TGCAGAACC
       H  R  L     S  R  R     Y  W  Q     M  R  P     L  F  Q     Q  L  L     V  N  H     A  E  C
1225 CACCGGCTG AGCAGGCGG TACTGGAAG ATGAGACCC CTGTTCCAG CAGCTGCTG GTGAACCAC GCCGAGTGC
       Q  Y  V     R  L  L     R  S  H     C  R  F     R  T  A     N  Q  Q     V  T  D     A  L  N
1297 CAGTATGTG CGGCTGCTG AGGAGCCAC TGCAGATTC AGGACCGCC AACCAGCAG GTGACCGAC GCCCTGAAC
       T  S  P     P  H  L     L  R  L     H  S  S     P  W  Q     V  Y  G     F  L  R
1369 ACCAGCCCC CCTCACCTG CTGAGGCTG CACAGCAGC CCCTGGCAG GTGTACGGC TTCCTGAGA
       A  C  L     C  K  V     V  S  A     S  L  W     G  T  R     H  N  E     R  R  F     F  K  N
1441 GCCTGCCTG TGCAAAGTG GTGTCCGCC AGCCTGTGG GGCACCAGA CACAACGAG CGGCGGTTC TTCAAGAAT
       L  K  K     F  I  S     L  G  K     Y  G  K     L  S  L     Q  E  L     M  W  K     M  K  V
1513 CTGAAGAAG TTCATCAGC CTGGGCAAG TACGGCAAG CTGAGCCTG CAGGAACTG ATGTGGAAG ATGAAAGTG
       E  D  C     H  W  L     R  S  S     P  G  K     D  R  V     P  A  A     E  H  R     L  R  E
1585 GAGGACTGC CACTGGCTG AGAAGCAGC CCCGGCAAG GACAGAGTG CCTGCCGCC GAGCACAGA CTGAGGGAG
       R  I  L     A  T  F     L  F  W     L  M  D     T  Y  V     V  Q  L     L  R  S     F  F  Y
1657 AGAATCCTG GCCACATTC CTGTTCTGG CTGATGGAC ACCTACGTG GTGCAGCTG CTGCGGTCC TTCTTCTAC
       I  T  E     S  T  F     Q  K  N     R  L  F     F  Y  R     K  S  V     W  S  K     L  Q  S
1729 ATCACCGAG AGCACCTTC CAGAAGAAC CGGCTGTTC TTCTACCGG AAGTCTGTG TGGAGCAAG CTGCAGAGC
       I  G  V     R  Q  H     L  E  R     V  R  L     R  E  L     S  Q  E     E  V  R     H  H  Q
1801 ATCGGAGTG AGACAGCAC CTGGAGAGA GTGAGGCTG AGAGAGCTG AGCCAGGAG GAAGTGAGA CACCACCAG
       D  T  W     L  A  M     P  I  C     R  L  R     F  I  P     K  P  N     G  L  R     P  I  V
1873 GATACCTGG CTGGCCATG CCCATCTGC CGGCTGAGA TTCATCCCC AAGCCCAAC GGCCTGAGA CCCATCGTG
       N  M  S     Y  S  M     G  T  R     A  L  G     R  R  K     Q  A  Q     H  F  T     Q  R  L
1945 AACATGAGC TACAGCATG GGCACCAGA GCCCTGGGC AGAAGAAAG CAGGCCCAG CACTTCACC CAGCGGCTG
```

FIG.2B

```
           K   T   L    F   S   M    L   N   Y    E   R   T    K   H   P    H   L   M    G   S   S    V   L   G
2017 AAAACCCTG TTCTCCATG CTGAACTAC GAGCGGACC AAGCACCCA CACCTGATG GGCAGCAGC GTGCTGGGC
           M   N   D    I   Y   R    T   W   R    A   F   V    L   R   V    R   A   L    D   Q   T    P   R   M
2089 ATGAACGAC ATCTACCGG ACCTGGAGA GCCTTCGTG CTGAGAGTG CGGGCCCTG GACCAGACC CCTCGGATG
           Y   F   V    K   A   A    I   T   G    A   Y   D    A   I   P    Q   G   K    L   V   E    V   V   A
2161 TACTTCGTG AAGGCCGCC ATCACCGGC GCCTACGAC GCCATCCCC CAGGGCAAA CTGGTGGAA GTGGTGGCC
           N   M   I    R   H   S    E   S   T    Y   C   I    R   Q   Y    A   V   V    R   R   D    S   Q   G
2233 AACATGATC AGGCACAGC GAGTCCACC TACTGCATC AGGCAGTAC GCCGTGGTG AGAAGAGAC AGCCAGGGC
           Q   V   H    K   S   F    R   R   Q    V   T   T    L   S   D    L   Q   P    Y   M   G    Q   F   L
2305 CAGGTGCAC AAGAGCTTC CGGAGACAG GTGACCACC CTGAGCGAT CTGCAGCCT TACATGGGC CAGTTCCTG
           K   H   L    Q   D   S    D   A   S    A   L   R    N   S   V    I   E   Q    S   I   S    M   N
2377 AAGCACCTG CAGGATAGC GACGCCAGC GCCCTGAGA AATAGCGTG GTGATCGAG CAGAGCATC AGCATGAAC
           E   S   S    S   L   F    D   F   F    L   H   F    L   R   H    S   V   V    K   I   G    D   R
2449 GAGTCCAGC AGCCTGTTC GACTTCTTC CTGCACTTC CTCCTGAGG CACAGCGTG GTGAAGATC GGCGACAGA
           C   Y   T    Q   C   Q    G   I   P    Q   G   S    S   L   S    T   L   L    C   S   L    C   F   G
2521 TGCTACACC CAGTGTCAG GGCATCCCT CAGGGCTCT AGCCTGAGC ACCCTGCTG TGTAGCCTG TGCTTCGGC
           D   M   E    N   K   L    F   A   E    V   Q   R    D   G   L    L   R   F    V   D   D    F   L
2593 GACATGGAG AATAAGCTG TTCGCCGAA GTGCAGAGA GATGGCCTG CTGAGGCACA CTGGTGCAC CCCTGGCTG
           L   V   T    P   H   L    D   Q   A    K   T   F    L   S   T    L   V   H    G   V   P    E   Y   G
2665 CTGGTGACC CCACACCTG GACCAGGCC AAGACCTTC CTGAGCACA CTGGTGCAC GGCGTGCCC GAGTACGGC
           C   M   I    N   L   Q    K   T   V    V   N   F    P   V   E    P   G   T    L   G   G    A   A   P
2737 TGCTACACC AATCTGCAG AAAACCGTG GTGAACTTC CCTGTGGAG CCCGGGACC CTGGGCGGA GCCGCCCCT
           Y   Q   L    P   A   H    C   L   F    P   W   C    G   L   L    L   D   T    Q   T   L    E   V   F
2809 TACCAGCTG CCCGCCCAC TGCCTGTTC CCCTGGTGC GGACTGCTG CTGGATACC CAGACCCTG GAAGTGTTC
           C   D   Y    S   G   Y    A   Q   T    S   I   K    T   S   L    T   F   Q    S   V   F    K   A   G
2881 TGCGACTAC AGCGGCTAC GCCCAGACC AGCATCAAG ACCAGCCTG ACCTTCCAG AGCGTGTTC AAGGCCGGC
           K   T   M    R   N   K    L   L   S    V   L   R    L   K   C    H   G   L    F   L   D    L   Q   V
2953 AAGACCATG AGGAACAAG CTGCTGAGC GTGCTGAGA CTGAAGTGC CACGGCCTG TTCCTGGAT CTGCAGGTG
```

FIG. 2C

```
            N  S  L     Q  T  V     C  I  N     I  Y  K     I  F  L     L  Q  A     Y  R  F     H  A  C
3025  AACAGCCTG CAGACCGTG TGTATCAAC ATCTACAAG ATTTTCCTG CTGCAGGCC TACAGATTC CACGCCTGC
            V  I  Q     L  P  F     D  Q  R     V  R  K     N  L  T     F  F  L     G  I  I     S  S  Q
3097  GTGATCCAG CTGCCCTTC GACCAGAGA GTGCGGAAG AACCTGACC TTCTTCCTG GGGATCATC AGCAGCCAG
            A  S  C     Y  A  I     L  K  V     K  N  P     G  M  T     L  K  A     S  G  S     F  P  P
3169  GCCAGCTGC TGCTACGCC ATCCTGAAA GTGAAGAAC CCCGGCATG ACCCTGAAG GCCAGCGGC AGCTTCCCT
            P  E  A     A  H  W     L  C  Y     Q  A  F     L  L  K     L  A  A     H  S  V     I  Y  K
3241  CCCGAGGCC GCCCACTGG CTGTGCTAC CAGGCCTTT CTGCTGAAG CTGGCCGCC CACAGCGTG ATCTACAAG
            C  L  L     G  P  L     R  T  A     Q  K  L     L  C  R     K  L  P     E  A  T     M  T  I
3313  TGCCTGCTG GGCCCTCTG AGAACCGCC CAGAAGCTG CTGTGCCGG AAGCTGCCC GAGGCCACC ATGACCATT
            L  K  A     A  D  P     A  L  S     T  D  F     Q  T  I     L  D  S     R  A  P     Q  S
3385  CTGAAAGCC GCCGACCCG GCCCTGAGC ACCGACTTT CAGACCATC CTGGACAGC AGGGCCCCT CAGAGCACC
            I  T  E     L  C  S     E  Y  R     N  T  Q     I  Y  T     I  N  D     K  I  L     S  Y  T
3457  ATCACCGAG CTGTGCAGC GAGTACCGG AACACCCAG ATTTACACC ATCAACGAC AAGATCCTG AGCTACACC
            E  S  M     A  G  K     R  E  M     V  I  I     T  F  K     S  A  G     T  F  Q     V  E  V
3529  GAGTCTATG GCCGGGAAG CGGGAGATG GTGATCATC ACCTTCAAG AGCGGGGCC ACCTTTCAG GTGGAAGTG
            P  G  S     Q  H  I     D  S  Q     K  K  A     I  E  R     M  K  D     T  L  R     I  T  Y
3601  CCTGGCAGC CAGCACATC GACAGCCAG AAGAAGGCC ATCGAGCGG ATGAAGGAC ACCCTGCGG ATCACCTAC
            L  T  E     T  K  I     D  K  L     C  V  W     N  N  K     T  P  N     S  I  A     I  S
3673  CTGACCGAG ACCAAGATC GACAAGCTG TGTGTGTGG AACAACAAG ACCCCCAAC AGCATCGCC GCCATCTCT
            M  E  N (SEQ ID NO:4)
3745  ATGGAGAAC (SEQ ID NO:3)
```

FIG.2D

Wilcoxon test of medians one-sided p-value = 0.016    Test of Poisson rates one-sided p-value = 0.033

US 8,017,387 B2

TELOMERASE REVERSE TRANSCRIPTASE FUSION PROTEIN, NUCLEOTIDES ENCODING IT, AND USES THEREOF

CROSS-REFERENCE TO RELATED APPLICATIONS

This application claims the benefit of U.S. Provisional Application No. 60/851,183, filed Oct. 12, 2006, the contents of which are incorporated herein by reference in their entirety.

FIELD OF THE INVENTION

The present invention relates generally to the therapy of cancer. More specifically, the present invention relates to polynucleotides encoding fusion proteins wherein the fusion proteins comprise at least a portion of the tumor associated polypeptide telomerase reverse transcriptase (TERT). The present invention also provides recombinant vectors and hosts comprising said polynucleotides, purified fusion proteins and methods for eliciting or enhancing an immune response against the protein product of the TERT gene, using the compositions and molecules disclosed herein.

BACKGROUND OF THE INVENTION

Vaccination has become a standard procedure for the prevention of numerous infectious diseases. The application of vaccines to other diseases, such as cancer, is now an attractive possibility due to advances in molecular engineering and a better understanding of tumor immunology.

Cancer is one of the leading causes of mortality worldwide. Despite an abundance of cancer-related research, conventional therapies that combine surgery, radiation, and chemotherapy, often fail to effectively treat established cancers. Reliable methods of prevention also remain unavailable.

Cancer typically involves the malfunction of genes that contribute to the regulation of the cell cycle or cell proliferation, such as growth factors and their receptors, oncogenes, and tumor suppressor genes. The products of many of these genes are expressed on the surface of a wide variety of tumor cells and, hence, are designated tumor-associated antigens (TAAs). The introduction of genes encoding TAAs directly into a subject has been shown to generate a protective immune response against the TAA in many experimental models, making these molecules a target for vaccine therapy. However, because many of these gene products are also expressed in normal cells, albeit at lower levels, many immunological therapies targeting TAAs have proven ineffective due to self-tolerance.

Genes coding for several tumor-associated antigens (TAA) have been isolated, characterized and inserted in genetic vectors such as plasmid DNA and viral vectors. One tumor-associated antigen that has been implicated in the pathogenesis of cancer is telomerase (TERT).

Telomerase is a DNA polymerase that normally functions in maintaining telomere length at the ends of chromosomes. During normal cell growth, an RNA primer attaches to the 5' end of DNA and initiates replication. Upon removal of the RNA primer, a gap in length is introduced to the resulting daughter strand of DNA. Thus, replication of a linear strand of DNA with conventional polymerases leads to shortening of telomere length in each progressive round of replication. Such shortening of telomere length is responsible for cellular senescence or aging of normal human somatic cells.

Telomerase is a ribonucleoprotein comprising an RNA component and a catalytic protein component (telomerase reverse transcriptase). The catalytic component of human telomerase was described by Meyerson et al. (*Cell* 1197: 785-95 (1990) and Nakamura et al. (*Science* 277: 955-59 (1997)). The TERT enzyme uses its RNA component as a template for telomere DNA synthesis, thus allowing telomeres to maintain their length over successive generations of cell growth. Such maintenance of telomere length over numerous proliferative cycles allows a cell to escape normal senescence and become immortal, allowing a tumor to grow and metastasize over great lengths of time. Because telomerase confers replicative immortality to cells, telomerase activity has been detected in cancerous cell lines and a diverse range of tumor types (Kim et al. *Science* 266: 2011-15 (1994)). Conversely, telomerase is inactive or only transiently expressed at low levels in normal human tissues and normal somatic cell cultures. The combination of telomerase overexpression in most cancer types as well as low or absent expression in normal cells makes TERT a target for therapy and/or prophylaxis of diseases associated with aberrant cellular proliferation such as cancer.

The development of a telomerase-specific vaccine is now possible because the catalytic and RNA components of telomerase have been cloned and characterized (see, e.g., U.S. Pat. No. 6,166,178). However, the development and commercialization of many vaccines have been hindered by difficulties associated with obtaining high expression levels of the desired immunogen in successfully transformed host organisms. The development of efficacious DNA-based vaccines has also been hindered by an inability to generate an immune response of sufficient magnitude in treated individuals to lead to tumor regression in a clinical setting. Therefore, despite the identification of the wild-type nucleotide sequences encoding telomerase proteins described above, it would be highly desirable to develop a vaccine which is capable of eliciting an enhanced TERT-specific immune response relative to a wild-type full-length TERT cDNA, when delivered to a mammal. It would also be desirable to develop methods for treating or preventing TERT-associated cancers which utilize nucleic acid molecules or proteins that safely and effectively potentiate a TERT-specific immune response.

SUMMARY OF THE INVENTION

As stated above, expression of the tumor-associated antigen telomerase reverse transcriptase (TERT) gene is commonly associated with the development or presence of adenocarcinomas, including colorectal carcinomas. To this end, the present invention relates to compositions and methods to elicit or enhance immunity to the protein products expressed by the human TERT (hTERT) gene. Specifically, the present invention provides polynucleotides encoding fusion proteins wherein the fusion proteins comprise the hTERT protein, or variant thereof, fused to a substantial portion of the B subunit of *E. coli* heat labile enterotoxin (LTB). The present invention also provides recombinant vectors, including but not limited to, adenovirus and plasmid vectors, comprising said polynucleotides and host cells comprising said recombinant vectors. Also provided herein are purified fusion proteins encoded by invention polynucleotides. The hTERT-LTB fusion proteins and polynucleotides which encode said fusion proteins are useful as vaccines for the prevention and/or treatment of telomerase-associated cancer. Said vaccines are useful as a monotherapy or as part of a therapeutic regime, said regime comprising administration of a second vaccine such as a polynucleotide, cell-based, protein, or peptide-based vaccine, or comprising radiotherapy or chemotherapy.

In preferred embodiments of the present invention, the sequence of nucleotides encoding hTERT and/or the sequence of nucleotides encoding LTB comprises codons that have been optimized for high levels of expression in a human host cell. In other words, in certain embodiments of the invention, the codon usage pattern of the polynucleotide sequence resembles that of highly expressed mammalian and/or human genes.

Another aspect of this invention is an expression construct comprising nucleotides encoding hTERT-LTB. In preferred embodiments of this portion of the invention, the construct comprises a TPA leader sequence before the coding sequence for the TERT gene to ensure that the TERT-LTB fusion protein is secreted.

In additional preferred embodiments of the present invention, telomerase catalytic activity of the telomerase antigen is inactivated so that the encoded TERT fusion protein is safer than wild-type TERT for vaccine purposes. The enzymatic activity of the TERT fusion protein can be inactivated by addition of mutations/deletions to the TERT-encoding nucleotide sequence. In specific exemplary embodiments of the invention, nucleotides have been mutated in order to change specific amino acids D712A and V713I in the human TERT protein sequence and D702A and V703I in the mouse TERT protein sequence.

The present invention further provides adenoviral and plasmid vectors comprising a nucleotide sequence that encodes an hTERT-LTB fusion protein. This invention also describes the use of the adenovirus and plasmid vectors in immunogenic compositions and vaccines for the prevention and/or treatment of hTERT-associated cancer.

Also provided are adenovirus vectors comprising a sequence of nucleotides that encode a human TERT protein or TERT protein variant. Variants useful in this aspect of the invention comprise mutations that function to eliminate telomerase catalytic activity. In preferred embodiments of this portion of the invention, the adenovirus vector is an Ad6 vector. In other preferred embodiments the Ad vector is an Ad 5 vector.

The present invention further provides methods for preventing the development of a cancer in a patient or treating a patient with a telomerase-associated tumor by eliciting an immune response to the TERT protein by administering a vaccine or pharmaceutical composition comprising the TERT fusions or TERT fusion proteins provided by the invention. In preferred embodiments of the methods herein, the immune response is enhanced relative to the response elicited by a wild-type TERT.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to a nucleotide or gene sequence that is to be expressed from a vector, for example, the nucleotide or gene sequence encoding the hTERT(AI)-LTB fusion. In general, a cassette comprises a gene sequence that can be inserted into a vector, which in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences that can be provided by the vector include, but are not limited to, enhancers, transcription termination sequences, splice acceptor and donor sequences, introns, ribosome binding sequences, and poly(A) addition sequences.

The term "vector" refers to some means by which DNA fragments can be introduced into a host organism or host tissue. There are various types of vectors including plasmid, virus (including adenovirus), bacteriophages and cosmids.

The term "first generation," as used in reference to adenoviral vectors, describes adenoviral vectors that are replication-defective. First generation adenovirus vectors typically have a deleted or inactivated E1 gene region, and preferably have a deleted or inactivated E3 gene region.

The designation "pV1JnsA/TPA-mTERT(AI)-LTBopt" refers to a plasmid construct, disclosed herein, comprising the CMV immediate-early (1E) promoter with intron A, a full-length codon-optimized murine TERT gene fused to a codon-optimized LTB gene, and bovine growth hormone-derived polyadenylation and transcriptional termination sequences (see EXAMPLE 2). Additionally, a leader sequence encoding the human tissue plasminogen activator (TPA) signal sequence is present 5' to the nucleotide sequence encoding mTERT-LTB. The designation "AI" indicates that mutations were added to the TERT sequence to functionally eliminate telomerase catalytic activity. The designation "pV1JnsA/mTERT(AI)opt" refers to a construct essentially as described above, except the construct comprises a murine optimized TERT nucleotide sequence that was not fused to LTB or to TPA.

The designation "pV1JnsA/TPA-hTERT(AI)-LTBopt" refers to a plasmid construct, disclosed herein, comprising the CMV immediate-early (1E) promoter with intron A, a full-length codon-optimized human TERT gene fused to a codon-optimized LTB gene, and bovine growth hormone-derived polyadenylation and transcriptional termination sequences (see EXAMPLE 2). Additionally, a leader sequence encoding the human tissue plasminogen activator (TPA) signal sequence is present 5' to the nucleotide sequence encoding hTERT-LTB. The hTERT sequence in this construct comprises mutations to functionally eliminate telomerase catalytic activity.

The designations "Ad6/TPAmTERT(AI)-LTBopt" and "Ad6/hTERT(AI)" refer to two constructs, disclosed herein, which comprise an Ad6 adenoviral genome deleted of the E1 and E3 regions. In the "Ad6/TPAmTERT(AI)-LTBopt" construct, the E1 region is replaced by a codon-optimized murine TERT-LTB gene in an E1 parallel orientation under the control of a human CMV promoter without intron A, followed by a bovine growth hormone polyadenylation signal. The TERT-encoding sequence comprises mutations to eliminate telomerase catalytic activity. The construct further comprises sequences encoding the human tissue plasminogen activator (TPA) signal sequence 5' to the TERT(AI)-LTB encoding nucleotide sequence. The "Ad6/hTERT(AI)" construct is essentially as described above, except the E1 region of the Ad6 genome is replaced with a TERT cDNA sequence, said sequence comprising mutations to abolish enzymatic activity.

The abbreviation "LTB" refers generally to the B subunit of heat labile enterotoxin of *E. coli*, or substantial portion thereof, including subunits which are truncated on the C-terminal or N-terminal end but maintain adjuvant activity, as well as subunits that contain internal amino acid insertions, deletions, or substitutions but maintain adjuvant activity (Fingerut et al. *Vaccine* 23: 4685-4696 (2005)).

As used herein, a "fusion protein" refers to a protein having at least two heterologous polypeptides covalently linked in which one polypeptide comes from one protein sequence or domain and the other polypeptide comes from a second protein sequence or domain. The fusion proteins of the present invention comprise a TERT polypeptide or fragment or variant thereof, and a second polypeptide, which comprises a substantial portion of LTB. The TERT polypeptide, fragment or variant thereof may be a human TERT or TERT homolog from another species, e.g. mouse. The polypeptides that comprise the fusion protein are preferably linked N-terminus to C-terminus. The TERT polypeptide and the LTB polypeptide can be fused in any order. In some embodiments of this invention, the C-terminus of the TERT polypeptide is fused to the N-terminus of LTB, as exemplified in FIGS. 1 and 2. However, fusion proteins in which the LTB subunit is fused to the N-terminus of the TERT polypeptide are also contemplated.

The term "TERT fusion protein" or "TERT-LTB fusion protein" are used interchangeably herein as a general term which refers to a fusion as described above, which comprises a TERT polypeptide or fragment or variant thereof fused to an LTB polypeptide. The term "TERT-LTB fusion" refers to a nucleic acid sequence in which at least a portion of the TERT gene is fused to a substantial portion of LTB subunit of *E. coli* heat labile enterotoxin. The term "TERT-LTB fusion protein" refers to a polypeptide encoded by a TERT-LTB fusion as described. The terms "TERT-LTB fusion" and "TERT-LTB fusion protein" are also understood to refer to fragments thereof, homologs thereof, and functional equivalents thereof (collectively referred to as "variants"), such as those in which one or more amino acids is inserted, deleted or replaced by other amino acid(s). The TERT-LTB fusions of the present invention, upon administration to a mammal such as a human being, can stimulate an immune response by helper T cells or cytotoxic T cells, at least as well as a "wild-type" hTERT sequence. In preferred embodiments of the invention, the TERT-LTB fusion can enhance the immune response as compared to a wild-type hTERT.

The term "treatment" refers to both therapeutic treatment and prophylactic or preventative measures. Those in need of treatment include those already with the disorder as well as those prone to have the disorder or those in which the disorder is to be prevented. As used herein, "treatment" also includes reduction of the likelihood of obtaining the disorder, as well as the reduction of the severity of the disorder in those already afflicted.

A "disorder" is any condition that would benefit from treatment with the molecules of the present invention, including the nucleic acid molecules described herein and the fusion proteins that are encoded by said nucleic acid molecules. Encompassed by the term "disorder" are chronic and acute disorders or diseases including those pathological conditions which predispose the mammal to the disorder in question. The molecules of the present invention are intended for use as treatments for disorders or conditions characterized by aberrant cell proliferation, including, but not limited to, breast cancer, colorectal cancer, and lung cancer.

The term "effective amount" means sufficient vaccine composition is introduced to produce the adequate levels of the polypeptide, so that an immune response results. One skilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

"hTERT" refers to a human telomerase reverse transcriptase antigen or nucleotides encoding the human telomerase reverse transcriptase antigen. "hTERTopt" refers to a codon-optimized nucleotide sequence encoding human telomerase reverse transcriptase antigen.

"Substantially similar" means that a given nucleic acid or amino acid sequence shares at least 75%, preferably at least 85%, more preferably at least 90%, and even more preferably at least 95% identity with a reference sequence. In the present invention, the reference sequence can be relevant portions of the wild-type human TERT nucleotide or amino acid sequence, as set forth in SEQ ID NOs:11 and 12, respectively, or the nucleotide or amino acid sequence of LTB, as set forth in SEQ ID NOs:13 (opt sequence) and 14, as dictated by the context of the text. The reference sequence may also be, for example, a wild-type rhesus monkey or murine TERT sequence. Thus, a TERT protein sequence that is "substantially similar" to the wild-type human TERT protein or fragment thereof will share at least 75% identity with the relevant fragment of the wild-type human TERT, along the length of the fragment, preferably 85% identity, more preferably 90% identity and even more preferably 95% identity. Whether a given mTERT, hTERT, or LTB amino acid sequence or nucleotide sequence is "substantially similar" to a reference sequence can be determined for example, by comparing sequence information using sequence analysis software such as the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981).

A "substantial portion" of a gene, variant, fragment, or subunit thereof, means a portion of at least 50%, preferably 75%, more preferably 90%, and even more preferably 95% of a reference sequence.

A "gene" refers to a nucleic acid molecule whose nucleotide sequence codes for a polypeptide molecule. Genes may be uninterrupted sequences of nucleotides or they may include such intervening segments as introns, promoter regions, splicing sites and repetitive sequences. A gene can be either RNA or DNA. A preferred gene is one that encodes the invention peptide.

The term "nucleic acid" or "nucleic acid molecule" is intended for ribonucleic acid (RNA) or deoxyribonucleic acid (DNA), probes, oligonucleotides, fragment or portions thereof, and primers.

"Wild-type TERT" or "wild-type protein" or "wt protein" refers to a protein comprising a naturally occurring sequence of amino acids or variant thereof. The amino acid sequence of wild-type human TERT is set forth in SEQ ID NO:12. The amino acid sequence of the wild-type human TERT was previously described (U.S. Pat. Nos. 6,166,178; 6,261,836; 6,927,285; U.S. Patent Application 2003-0096344; Meyerson et al., *Cell* 90: 785-95 (1997); Nakamura et al., *Science* 277: 955-59 (1997)).

"Wild-type TERT gene" refers to a gene comprising a sequence of nucleotides that encodes a naturally occurring TERT protein, including proteins of human origin or proteins obtained from another organism, including, but not limited to, other mammals such as rat, mouse and rhesus monkey. The nucleotide sequence of the human TERT gene is available in the art (supra).

The designation "TERT(AI)" refers to a telomerase reverse transcriptase sequence that comprises mutations to eliminate or reduce telomerase catalytic activity.

The term "mammalian" refers to any mammal, including a human being.

The abbreviation "Ag" refers to an antigen.

The abbreviation "ORF" refers to the open reading frame of a gene.

BRIEF DESCRIPTION OF THE DRAWINGS

FIG. 1 shows the nucleotide (SEQ ID NO:1) and amino acid sequence (SEQ ID NO:2) of an exemplary TPA-hTERT (AI)-LTBopt fusion.

FIG. 2 shows the nucleotide (SEQ ID NO:3) and amino acid sequence (SEQ ID NO:4) of an exemplary TPA-mTERT (AI)-LTBopt fusion.

DETAILED DESCRIPTION OF THE INVENTION

Figure 3:
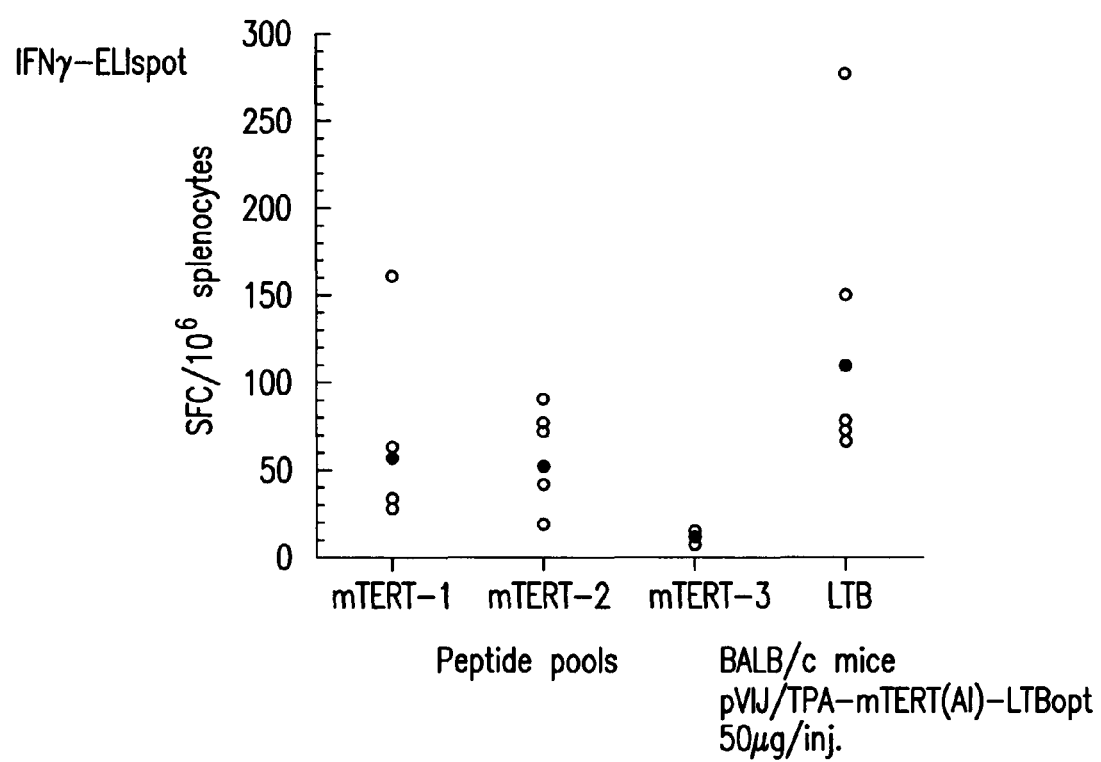
FIG. 3 shows results of an IFNγ ELIspot assay on BALB/c mice vaccinated with repeated injections of plasmid pV1J/TPA-mTERT(AI)-LTBopt. 5 mice of each group were used to monitor immune response directed against mTERT or LTB using peptide pools. Data plotted are from 6 individual mice (empty circle). Geometric mean values are indicated (filled circles). No T cell response to mTERT was detected in mock treated mice (not shown). See EXAMPLE 7.

Expression of the catalytic component of telomerase, known as telomerase reverse transcriptase (TERT) is commonly detected in a diverse range of tumor types. The combination of telomerase over-expression in most cancer types as well as low or absent expression in normal cells makes TERT a target for therapy and/or prophylaxis of diseases associated with aberrant cellular proliferation such as cancer. To this end, the present invention relates to compositions and methods to elicit or enhance immunity to the protein product expressed by the TERT tumor-associated antigen, wherein aberrant TERT expression is associated with the carcinoma or its development. Association of aberrant TERT expression with a carcinoma does not require that the TERT protein be expressed in tumor tissue at all time points of its development, as abnormal TERT expression may be present at tumor initiation and not be detectable late into tumor progression or vice-versa.

Accordingly, the present invention provides polynucleotides, vectors, host cells, and encoded proteins comprising a TERT sequence or variant thereof for use in vaccines and pharmaceutical compositions for the treatment and/or prevention of a cancer. The polynucleotides of the present invention comprise a nucleotide sequence encoding a TERT protein or variant thereof, fused to a nucleotide sequence encoding the B subunit of E. coli heat labile enterotoxin (LTB), which is able to effectively adjuvant an immune response to the associated TERT antigen.

In some embodiments of the invention, the nucleotide sequences disclosed herein further comprise a TPA leader sequence before the coding sequence for the TERT gene to ensure that the TERT-LTB fusion protein is secreted. In preferred embodiments of this aspect of the invention, the TPA-hTERT(AI)-LTB fusion encodes an amino acid sequence as set forth in SEQ ID NO:2. A preferred nucleotide sequence is set forth in SEQ ID NO:1. In further preferred embodiments, the TPA-mTERT(AI)-LTB fusion encodes an amino acid sequence as set forth in SEQ ID NO:4. A preferred nucleotide sequence is set forth in SEQ ID NO:3.

The TERT nucleotide sequences of the present invention can be of human origin or can be a TERT homolog from another species, e.g. mouse. The wild-type human TERT nucleotide sequence is set forth in SEQ ID NO:12 and has been reported previously (see, e.g., U.S. Pat. Nos. 6,166,178; 6,261,836; 6,927,285; U.S. Patent Application 2003-0096344; Meyerson et al., Cell 90: 785-95 (1997); Nakamura et al., Science 277: 955-59 (1997)). The TERT portion of the TERT fusion may be full-length, or any variant sufficient to elicit a TERT-specific T-cell immune response in a mammal. TERT variants of the present invention include, but are not limited to sequences that are C- or N-terminally truncated, sequences with conservative substitutions, and sequences with internal deletions or insertions. Preferred TERT variants of the present invention comprise mutations that functionally eliminate telomerase catalytic activity. Encoded TERT fusion proteins of the present invention are capable of inducing a cell-mediated immune response when introduced into a vaccine recipient or patient in need thereof.

As stated above, in preferred embodiments of the present invention, telomerase catalytic activity of the telomerase antigen is inactivated (herein designated "TERT(AI)") so that the encoded TERT fusion protein is safer than wild-type TERT for vaccine purposes. The enzymatic activity of the TERT fusion protein can be inactivated by addition of mutations/deletions to the TERT-encoding nucleotide sequence. Therefore, the present invention includes nucleic acid molecules that encode a TERT-LTB fusion protein, wherein the sequence of nucleotides encodes a variant hTERT protein, wherein said variant comprises one or more mutations relative to the wild-type hTERT amino acid sequence as set forth in SEQ ID NO: 12, and wherein said mutations function to eliminate telomerase catalytic activity of the encoded hTERT protein. In specific exemplary embodiments of the invention, nucleotides have been mutated in order to change specific amino acids D712A and V713I in the human TERT protein sequence (as set forth in SEQ ID NO:10) and D702A and V703I in the mouse TERT protein sequence. A nucleotide sequence encoding the mutated human TERT sequence set forth in SEQ ID NO:10 is disclosed in SEQ ID NO:9.

In preferred embodiments of the present invention, the TERT portion of the TERT-LTB fusion is human TERT or a variant thereof, such as hTERT(AI). In other preferred embodiments, the TERT portion is a murine TERT, or variant thereof, such as mTERT(AI). The TERT variants and TERT-encoding nucleotide sequence variants of the present invention comprise mutations that abolish telomerase enzymatic activity.

Accordingly, the present invention relates to synthetic polynucleotides comprising a sequence of nucleotides encoding a TERT-LTB fusion protein, said fusion protein comprising a TERT protein or a biologically inactive fragment or mutant form of a TERT protein fused to an LTB protein or variant thereof, which can effectively enhance the immune response to the TERT protein. Said mutant forms of the TERT protein include, but are not limited to: conservative amino acid substitutions, amino-terminal truncations, carboxy-terminal truncations, deletions, or additions. Any such TERT variant, fragment and/or mutant will encode either a protein or protein fragment which at least substantially mimics the immunological properties of the TERT protein as set forth in SEQ ID NO:12. Preferred TERT variants are catalytically inactive, for example, the TERT variant set forth in SEQ ID NO:10.

The synthetic polynucleotides of the present invention encode mRNA molecules that express a TERT(AI)-LTB fusion protein that is capable of stimulating or enhancing the immune response to the associated TERT protein, so as to be useful in the development of a therapeutic or prophylactic cancer vaccine. The LTB portion of the TERT-LTB fusions of the present invention has been shown to strongly potentiate the immunogenicity of co-delivered antigens (See, e.g. Simmons et al. Scand. J. Immunol. 53:218-26 (2001)).

Also contemplated for use in the present invention are nucleotide sequences encoding LTB variants or mutants including but not necessarily limited to: nucleotide substitutions, deletions, additions, amino-terminal truncations and carboxy-terminal truncations. In some cases, it may be advantageous to add specific point mutations to the nucleotide sequence encoding LTB to reduce or eliminate toxicity of the encoded protein. In preferred embodiments of the present invention the LTB sequence fused to the TERT sequence is truncated of its signal sequence.

The LTB portion, or variant thereof, of the TERT-LTB fusions of the present invention may be fused to the amino terminus or the carboxy terminus of the TERT sequence. Further, the LTB sequence and the TERT sequence can be fused N-terminus to N-terminus, C-terminus to C-terminus, C-terminus to N-terminus or N-terminus to N-terminus. In preferred embodiments of the present invention, the C-terminus of the TERT polypeptide is fused to the N-terminus of LTB.

The present invention relates to a synthetic nucleic acid molecule (polynucleotide) comprising a sequence of nucleotides which encodes mRNA that expresses a novel TERT-LTB fusion protein; for example, nucleotide sequences encoding the fusion proteins as set forth in SEQ ID NOs:6 and 8. A particularly preferred TERT fusion of the present invention is the hTERT(AI)-LTB fusion sequence set forth in SEQ ID NO:5. The nucleic acid molecules of the present invention are substantially free from other nucleic acids.

One of skill in the art will recognize that other nucleotide sequences are useful for vaccine purposes, such as nucleotide sequences that encode the hTERT(AI)-LTB protein sequence set forth in SEQ ID NO:6. The present invention also includes nucleotide sequences that encode inactive hTERT-LTB fusion protein that are substantially similar, to SEQ ID NO:6, but not exactly the same, especially due to amino acid differences at the junction of the TERT(AI) sequence and the LTB sequence that were created by the cloning strategy.

The present invention also relates to recombinant vectors and recombinant host cells, both prokaryotic and eukaryotic, which contain the nucleic acid molecules disclosed throughout this specification. The synthetic DNA molecules, associated vectors, and hosts of the present invention are useful for the development of a cancer vaccine.

Exemplary nucleic acid molecules of the present invention comprise a nucleotide sequence selected from the group consisting of: SEQ ID NOs:5 and 7, as shown in FIGS. 1-2, which encode exemplary hTERT-LTB and mTERT-LTB fusion proteins of the present invention.

The present invention also includes biologically active fragments or mutants of SEQ ID NOs: 5 and 7, which encode mRNA expressing exemplary TERT-LTB fusion proteins. Any such biologically active fragment and/or mutant will encode either a protein or protein fragment which at least substantially mimics the immunological properties of the hTERT protein, including but not limited to the hTERT protein as set forth in SEQ ID NO:12. Such polynucleotides include but are not necessarily limited to: nucleotide substitutions, deletions, additions, amino-terminal truncations and carboxy-terminal truncations. Preferred mutated nucleotide sequences of the present invention encode mRNA molecules that express an enzymatically inactive TERT-LTB fusion protein in a eukaryotic cell, which is capable of eliciting a prophylactic or therapeutic immune response in a patient in need thereof so as to be useful in cancer vaccine development.

Also included within the scope of this invention are mutations in the DNA sequence that do not substantially alter the ultimate physical properties of the expressed protein. For example, substitution of valine for leucine, arginine for lysine, or asparagine for glutamine may not cause a change in the desired functionality of the polypeptide, such as the ability to elicit an immune response.

As stated above, the present invention further relates to recombinant vectors that comprise the nucleic acid molecules disclosed throughout this specification. These vectors may be comprised of DNA or RNA. For most cloning purposes, DNA vectors are preferred. Typical vectors include plasmids, modified viruses, baculovirus, bacteriophage, cosmids, yeast artificial chromosomes, and other forms of episomal or integrated DNA that can encode a TERT-LTB fusion protein. It is well within the purview of the skilled artisan to determine an appropriate vector for a particular gene transfer or other use.

Also provided by the present invention are purified TERT-LTB fusion proteins encoded by the nucleic acids disclosed throughout this specification, especially TERT(AI)-LTB fusion proteins. In exemplary embodiments of this aspect of the invention, the TERT-LTB fusion protein comprises a sequence of amino acids selected from the group consisting of: SEQ ID NOs: 6 and 8.

Included in the present invention are DNA sequences that hybridize to the complement of SEQ ID NOs: 5 and 7 under stringent conditions. By way of example, and not limitation, a procedure using conditions of high stringency is as follows. Prehybridization of filters containing DNA is carried out for about 2 hours to overnight at about 65° C. in buffer composed of 6× SSC, 5×Denhardt's solution, and 100 μg/ml denatured salmon sperm DNA. Filters are hybridized for about 12 to 48 hrs at 65° C. in prehybridization mixture containing 100 μg/ml denatured salmon sperm DNA and 5-20×10$^6$ cpm of $^{32}$P-labeled probe. Washing of filters is done at 37° C. for about 1 hour in a solution containing 2× SSC, 0.1% SDS. This is followed by a wash in 0.1× SSC, 0.1% SDS at 50° C. for 45 minutes before autoradiography. Other procedures using conditions of high stringency would include either a hybridization step carried out in 5× SSC, 5×Denhardt's solution, 50% formamide at about 42° C. for about 12 to 48 hours or a washing step carried out in 0.2× SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

An expression vector containing a TERT-LTB fusion protein-encoding nucleic acid molecule may be used for high-level expression of TERT-LTB fusion protein in a recombinant host cell. Expression vectors may include, but are not limited to, cloning vectors, modified cloning vectors, specifically designed plasmids or viruses. Also, a variety of bacterial expression vectors may be used to express recombinant TERT-LTB fusion sequences in bacterial cells if desired. In addition, a variety of fungal cell expression vectors may be used to express recombinant TERT-LTB fusion sequences in fungal cells. Further, a variety of insect cell expression vectors may be used to express recombinant protein in insect cells.

The present invention also relates to host cells transformed or transfected with vectors comprising the nucleic acid molecules of the present invention. Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. Such recombinant host cells can be cultured under suitable conditions to produce a TERT-LTB fusion protein or a biologically equivalent form. In a preferred embodiment of the present invention, the host cell is human. As defined herein, the term "host cell" is not intended to include a host cell in the body of a transgenic human being, human fetus, or human embryo.

As noted above, an expression vector containing DNA encoding a TERT-LTB fusion protein may be used for expression of TERT fusion protein in a recombinant host cell. Therefore, another aspect of this invention is a process for expressing a TERT-LTB fusion protein in a recombinant host cell, comprising: (a) introducing a vector comprising a nucleic acid comprising a sequence of nucleotides that encodes a TERT-LTB fusion protein into a suitable human host cell, wherein the TERT-LTB fusion protein comprises a TERT protein or inactive variant thereof, fused to a substantial portion of the LTB protein, and wherein the fusion protein is capable of producing an immune response in a mammal; and, (b) culturing the host cell under conditions which allow expression of said TERT-LTB fusion protein.

In preferred embodiments of the process for expressing a TERT-LTB fusion protein described above, the LTB sequence is deleted of its signal sequence.

Following expression of a TERT-LTB fusion in a host cell, TERT-LTB fusion protein may be recovered to provide purified TERT-LT fusion protein. Several protein purification procedures are available and suitable for use. Recombinant protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant TERT-LTB fusion protein can be separated from other cellular proteins by use of an immunoaffinity column made with monoclonal or polyclonal antibodies specific for a TERT protein, or polypeptide fragments of a TERT protein.

The nucleic acid molecules comprising TERT-LTB fusions and the encoded fusion proteins of this invention were designed to enhance the TERT-specific immune response, relative to full-length wild-type cDNA encoding TERT, for use in vaccine development. To further enhance the immunogenic properties of the TERT-LTB fusion sequences of the present invention, in some embodiments described herein, the polynucleotides encoding TERT-LTB fusion proteins comprise optimized codons for further high level expression in a host cell, as described below. In these embodiments, at least a portion of the codons of the TERT-LTB fusions are designed so as to use the codons preferred by the projected host cell, which in preferred embodiments is a human cell. The optimized TERT-LTB fusions may be used for the development of recombinant adenovirus or plasmid-based DNA vaccines, which provide effective immunoprophylaxis against TERT-associated cancer through cell-mediated immunity. The synthetic molecules may be used as an immunogenic composition. This invention provides codon-optimized TERT-LTB fusion polynucleotides which, when directly introduced into a vertebrate in vivo, including mammals such as primates and humans, induce the expression of encoded proteins within the animal.

As stated above, in some embodiments of the present invention, the synthetic molecules comprise a sequence of nucleotides, wherein some of the nucleotides have been altered so as to use the codons preferred by a human cell, thus allowing for high-level fusion protein expression in a human host cell. The synthetic molecules may be used as a source of a TERT-LTB fusion protein, which may be used in a cancer vaccine to provide effective immunoprophylaxis against TERT-associated carcinomas through cell-mediated immunity. The nucleic acid molecules disclosed herein may also serve as the basis for a DNA-based cancer vaccine.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are evident, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant DNA techniques. Thus, one aspect of this invention is a TERT-LTB fusion gene that is codon-optimized for expression in a human cell. In a preferred embodiment of this invention, it has been found that the use of alternative codons encoding the same protein sequence may remove the constraints on expression of exogenous TERT-LTB fusion protein in human cells.

In accordance with some embodiments of the present invention, the nucleic acid molecules which encode the TERT-LTB fusion proteins are converted to a polynucleotide sequence having an identical translated sequence but with alternative codon usage as described by Lathe, "Synthetic Oligonucleotide Probes Deduced from Amino Acid Sequence Data: Theoretical and Practical Considerations" *J Molec. Biol.* 183:1-12 (1985), which is hereby incorporated by reference. The methodology generally consists of identifying codons in the wild-type sequence that are not commonly associated with highly expressed human genes and replacing them with optimal codons for high expression in human cells. The new gene sequence is then inspected for undesired sequences generated by these codon replacements (e.g., "ATTTA" sequences, inadvertent creation of intron splice recognition sites, unwanted restriction enzyme sites, etc.). Undesirable sequences are eliminated by substitution of the existing codons with different codons coding for the same amino acid. The synthetic gene segments are then tested for improved expression.

It is understood that this procedure will not necessarily result in a polynucleotide sequence in which all of the codons are optimal codons according to the codon usage of highly expressed human and/or mammalian cells. However, it is preferred that, in embodiments of the invention wherein codon-optimized polynucleotide variants of TERT and/or LTB are contemplated, a substantial portion of the resulting codons resemble the codon usage of highly expressed human and/or mammalian genes.

The methods described above were used to create synthetic gene sequences which encode TERT-LTB fusion proteins, resulting in a gene comprising codons optimized for high level expression in human cells. While the above procedure provides a summary of a representative methodology for designing codon-optimized genes for use in cancer vaccines, it is understood by one skilled in the art that similar vaccine efficacy or increased expression of genes may be achieved by minor variations in the procedure or by minor variations in the sequence.

One of skill in the art will also recognize that additional nucleic acid molecules may be constructed that provide for high levels of TERT-LTB fusion expression in human cells, wherein only a portion of the codons of the DNA molecules are codon-optimized. For example, in some embodiments of the present invention, codons comprising the TERT portion of the TERT-LTB fusion are optimized for high-level expression in human cells, and codons comprising the LTB portion of the TERT-LTB fusion are substantially similar to the wild-type LTB. In other embodiments of the present invention, codons comprising the LTB portion of the TERT-LTB fusion are optimized for high-level expression in human cells, and codons comprising the TERT portion of the TERT-LTB fusion are substantially similar to a wild-type TERT gene. In still other embodiments of the present invention, both the TERT and LTB portions of the TERT-LTB fusion are codon-optimized for high-level expression in human cells, for example, the hTERT-LTBopt sequence as set forth in SEQ ID NO:5. TERT-LTB fusions in which only a subset of codons are optimized within the TERT and/or the LTB portion of the TERT-LTB fusion are also contemplated by this invention.

The nucleic acids of the present invention may be assembled into an expression cassette which comprises sequences designed to provide for efficient expression of the protein in a human cell. The cassette preferably contains TERT-LTB fusion protein-encoding gene, with related transcriptional and translations control sequences operatively linked to it, such as a promoter, and termination sequences. In a preferred embodiment, the promoter is the cytomegalovirus promoter with intron A sequence (CMV), although those skilled in the art will recognize that any of a number of other known promoters such as a strong immunoglobulin or other eukaryotic gene promoter may be used. A preferred transcriptional terminator is the bovine growth hormone terminator, although other known transcriptional terminators may also be used. The combination of CMV-BGH terminator is particularly preferred.

In accordance with this invention, the TERT-LTB fusion expression cassette is inserted into a vector. The vector is preferably an adenoviral or plasmid vector, although linear DNA linked to a promoter, or other vectors, such as adeno-associated virus or a modified vaccinia virus, retroviral or lentiviral vector may also be used.

In preferred embodiment of the invention, the vector is an adenovirus vector (used interchangeably herein with "aden-ovector"). Adenovectors can be based on different adenovirus serotypes such as those found in humans or animals. Examples of animal adenoviruses include bovine, porcine, chimp, murine, canine, and avian (CELO). Preferred adenovectors are based on human serotypes, more preferably Group B, C, or D serotypes. Examples of human adenovirus Group B, C, D, or E serotypes include types 2 ("Ad2"), 4 ("Ad4"), 5 ("Ad5"), 6 ("Ad6"), 24 ("Ad24"), 26 ("Ad26"), 34 ("Ad34") and 35 ("Ad35"). In particularly preferred embodiments of the present invention, the expression vector is an adenovirus type 6 (Ad6) vector.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In addition, first generation vectors may have a non-functional or deleted E3 gene region (Danthinne et al. *Gene Therapy* 7:1707-1714 (2000); F. L. Graham, *Immunology Today* 21(9): 426-428 (2000)). Adenovectors do not need to have their E1 and E3 regions completely removed. Rather, a sufficient amount the E1 region is removed to render the vector replication incompetent in the absence of the E1 proteins being supplied in trans; and the E1 deletion or the combination of the E1 and E3 deletions are sufficiently large enough to accommodate a gene expression cassette.

In some embodiments, the expression cassette is inserted in the position where the adenoviral E1 gene is normally located. In addition, these vectors optionally have a non-functional or deleted E3 region. It is preferred that the adenovirus genome used be deleted of both the E1 and E3 regions ($\Delta E1\Delta E3$). The adenoviruses can be multiplied in known cell lines which express the viral E1 gene, such as 293 cells, or PERC.6 cells, or in cell lines derived from 293 or PERC.6 cell which are transiently or stably transformed to express an extra protein. For examples, when using constructs that have a controlled gene expression, such as a tetracycline regulatable promoter system, the cell line may express components involved in the regulatory system. One example of such a cell line is T-Rex-293; others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising a TERT-LTB fusion protein-encoding nucleotide sequence. In preferred embodiments, there is a restriction site flanking the adenoviral portion of the plasmid so that the adenoviral vector can easily be removed. The shuttle plasmid may be replicated in prokaryotic cells or eukaryotic cells.

In a preferred embodiment of the invention, the expression cassette is inserted into an Ad6 ($\Delta E1\Delta E3$) adenovirus plasmid (See Emini et al., US20040247615, which is hereby incorporated by reference). This vector comprises an Ad6 adenoviral genome deleted of the E1 and E3 regions. In other preferred embodiments of the invention, the expression cassette is inserted into the pMRKAd5-HV0 adenovirus plasmid (See Emini et al., US20030044421, which is hereby incorporated by reference). This plasmid comprises an Ad5 adenoviral genome deleted of the E1 and E3 regions. The design of the pMRKAd5-HV0 plasmid was improved over prior adenovectors by extending the 5' cis-acting packaging region further into the E1 gene to incorporate elements found to be important in optimizing viral packaging, resulting in enhanced virus amplification. Advantageously, these enhanced adenoviral vectors are capable of maintaining genetic stability following high passage propagation.

Standard techniques of molecular biology for preparing and purifying DNA constructs enable the preparation of the adenoviruses, shuttle plasmids, and DNA immunogens of this invention.

It has been determined in accordance with the present invention that genetic vaccination with plasmid DNA coding for TPA-mTERT(AI)-LTBopt can break immune tolerance in BALB/c and B6 mice (See EXAMPLE 7). It has also been shown herein that immunization with plasmid TPA-mTERT (AI)-LTBopt can elicit a cytotoxic immune response in BALB/c mice (See EXAMPLE 8). It has further been demonstrated that this construct is able to induce a stronger CD8+ immune response than mTERT(AI) alone (see EXAMPLE 9), and is able to control tumor growth (EXAMPLE 11). Thus, the data described herein demonstrate that fusion of the TERT coding sequence to the LTB cDNA results in an increase in the TERT-specific immune response.

It has also been shown in accordance with the present invention that hTERT(AI)-LTBopt can induce an HLA-A2 restricted CD8+ immune response (see EXAMPLE 12) and that this immune response can be amplified by boosting with Ad6-hTERT(AI).

Therefore, the vectors described above may be used in immunogenic compositions and vaccines for preventing the development of tumors associated with aberrant TERT expression and/or for treating existing cancers. The vectors of the present invention allow for vaccine development and commercialization by eliminating difficulties with obtaining high expression levels of exogenous TERT in successfully transformed host organisms and by providing a TERT-LTB fusion protein which can elicit an enhanced immune response when administered to a mammal such as a human being.

To this end, one aspect of the instant invention is a method of preventing or treating TERT-associated cancer comprising administering to a mammal a vaccine vector comprising a polynucleotide comprising a sequence of nucleotides that encodes a TERT-LTB fusion protein, wherein the TERT-LTB fusion protein comprises an inactive TERT protein or variant thereof, fused to a substantial portion of LTB and wherein the fusion protein is capable of producing an immune response in a mammal.

In accordance with the method described above, the vaccine vector may be administered for the treatment or prevention of a cancer in any mammal, including but not limited to: lung cancer, breast cancer, and colorectal cancer. In a preferred embodiment of the invention, the mammal is a human.

Further, one of skill in the art may choose any type of vector for use in the treatment and prevention method described. Preferably, the vector is an adenovirus vector or a plasmid vector. In a preferred embodiment of the invention, the vector is an adenoviral vector comprising an adenoviral genome with a deletion in the adenovirus E1 region, and an insert in the adenovirus E1 region, wherein the insert comprises an expression cassette comprising: (a) a sequence of nucleotides that encodes a TERT-LTB fusion protein, wherein the TERT-LTB fusion protein comprises an inactive TERT protein or variant thereof, fused to a substantial portion of LTB and wherein the fusion protein is capable of producing an immune response in a mammal; and (b) a promoter operably linked to the polynucleotide.

The instant invention further relates to an adenovirus vaccine vector comprising an adenoviral genome with a deletion in the E1 region, and an insert in the E1 region, wherein the insert comprises an expression cassette comprising: (a) a sequence of nucleotides that encodes a TERT fusion protein, wherein the TERT fusion protein comprises an inactive TERT protein or variant thereof, fused to a substantial portion of LTB and wherein the fusion protein is capable of producing an immune response in a mammal; and (b) a promoter operably linked to the polynucleotide.

In a preferred embodiment of this aspect of the invention, the adenovirus vector is an Ad 6 vector.

In another preferred embodiment of the invention, the adenovirus vector is an Ad 5 vector.

In yet another preferred embodiment, the adenovirus vector is an Ad 24 vector.

Also contemplated for use in the present invention is an adenovirus vaccine vector comprising an adenovirus genome that naturally infects a species other than human, including, but not limited to, chimpanzee adenoviral vectors. A preferred embodiment of this aspect of the invention is a chimp Ad 3 vaccine vector.

In another aspect, the invention relates to a vaccine plasmid comprising a plasmid portion and an expression cassette portion, the expression cassette portion comprising: (a) a sequence of nucleotides that encodes a TERT fusion protein, wherein the TERT fusion protein comprises an inactive TERT protein or variant thereof, fused to a substantial portion of LTB and wherein the fusion protein is capable of producing an immune response in a mammal; and (b) a promoter operably linked to the polynucleotide. An example of a suitable plasmid would be the mammalian expression plasmid V1Jns as described (J. Shiver et. al. in *DNA Vaccines*, M. Liu et al. eds., N.Y. Acad. Sci., N.Y., 772:198-208 (1996), which is herein incorporated by reference).

In some embodiments of this invention, the recombinant adenovirus and plasmid-based polynucleotide vaccines disclosed herein are used in various prime/boost combinations in order to induce an enhanced immune response. In this case, the two vectors are administered in a "prime and boost" regimen. For example the first type of vector is administered one or more times, then after a predetermined amount of time, for example, 2 weeks, 1 month, 2 months, six months, or other appropriate interval, a second type of vector is administered one or more times. Preferably the vectors carry expression cassettes encoding the same polynucleotide or combination of polynucleotides.

In the embodiment where a plasmid DNA is also used, it is preferred that the vector contain one or more promoters recognized by mammalian or insect cells. In a preferred embodiment, the plasmid would contain a strong promoter such as, but not limited to, the CMV promoter. One of skill in the art will recognize that any of a number of other known promoters may be chosen for purposes of driving expression of the TERT-LTB nucleotide sequences of the present invention. Additional examples of promoters include naturally occurring promoters such as the EF1 alpha promoter, Rous sarcoma virus promoter, and SV40 early/late promoters and the p-actin promoter; and artificial promoters such as a synthetic muscle specific promoter and a chimeric muscle-specific/CMV promoter (Li et al., *Nat. Biotechnol.* 17:241-245 (1999); Hagstrom et al., *Blood* 95:2536-2542 (2000)). The synthetic TERT-LTB fusion gene or other gene to be expressed would be linked to such a promoter.

As stated above, an adenoviral vector vaccine and a plasmid vaccine may be administered to a vertebrate as part of a single therapeutic regime to induce an immune response. To this end, the present invention relates to a method of protecting a mammal from a TERT-associated cancer comprising: (a) introducing into the mammal a first vector comprising: i) a sequence of nucleotides that encodes a TERT fusion protein, wherein the TERT fusion protein comprises an inactive TERT protein or variant thereof, fused to a substantial portion of LTB and wherein the fusion protein is capable of producing an immune response in a mammal; and ii) a promoter operably linked to the polynucleotide; (b) allowing a predetermined amount of time to pass; and (c) introducing into the mammal a second vector comprising: i) a sequence of nucleotides that encodes a TERT fusion protein, wherein the TERT fusion protein comprises an inactive TERT protein or variant thereof, fused to a substantial portion of LTB and wherein the fusion protein is capable of producing an immune response in a mammal; and ii) a promoter operably linked to the polynucleotide.

In one embodiment of the method of protection described above, the first vector is a plasmid and the second vector is an adenovirus vector. In an alternative embodiment, the first vector is an adenovirus vector and the second vector is a plasmid. In some embodiments of the present invention, the first vector is administered to the patient more than one time before the second vector is administered.

In the method described above, the first type of vector may be administered more than once, with each administration of the vector separated by a predetermined amount of time. Such a series of administration of the first type of vector may be followed by administration of a second type of vector one or more times, after a predetermined amount of time has passed. Similar to treatment with the first type of vector, the second type of vector may also be given one time or more than once, following predetermined intervals of time.

The instant invention further relates to a method of treating a patient suffering from a TERT-associated cancer comprising: (a) introducing into the mammal a first vector comprising: i) a sequence of nucleotides that encodes a TERT fusion protein, wherein the TERT fusion protein comprises a TERT (AI) protein or variant thereof, fused to a substantial portion of LTB and wherein the fusion protein is capable of producing an immune response in a mammal; and ii) a promoter operably linked to the polynucleotide; (b) allowing a predetermined amount of time to pass; and (c) introducing into the patient a second vector comprising: i) a sequence of nucleotides that encodes a TERT fusion protein, wherein the TERT fusion protein comprises a TERT(AI) protein or variant thereof, fused to a substantial portion of LTB and wherein the fusion protein is capable of producing an immune response in a mammal; and ii) a promoter operably linked to the polynucleotide.

In one embodiment of the method of treatment described above, the first vector is a plasmid and the second vector is an adenovirus vector. In an alternative embodiment, the first vector is an adenovirus vector and the second vector is a plasmid. In further preferred embodiments of the method described above, the first vector is administered to the patient more than one time before the second vector is administered to the patient.

In preferred embodiments of the methods described above, the vectors comprise a sequence of nucleotides that encode a TERT(AI)-LTB fusion protein, wherein the TERT fusion protein comprises an inactive TERT protein, fused to a substantial portion of LTB.

The amount of expressible DNA or transcribed RNA to be introduced into a vaccine recipient will depend partially on the strength of the promoters used and on the immunogenicity of the expressed gene product. In general, an immunologically or prophylactically effective dose of about 1 ng to 100 mg, and preferably about 10 μg to 300 μg of a plasmid vaccine vector is administered directly into muscle tissue. An effective dose for recombinant adenovirus is approximately $10^6$-$10^{12}$ particles and preferably about $10^7$-$10^{11}$ particles. Sub-cutaneous injection, intradermal introduction, impression though the skin, and other modes of administration such as intraperitoneal, intravenous, intramuscular or inhalation delivery are also contemplated.

In preferred embodiments of the present invention, the vaccine vectors are introduced to the recipient through intramuscular injection.

The vaccine vectors of this invention may be naked, i.e., unassociated with any proteins, or other agents which impact on the recipient's immune system. In this case, it is desirable for the vaccine vectors to be in a physiologically acceptable solution, such as, but not limited to, sterile saline or sterile buffered saline. Alternatively, it may be advantageous to administer an agent which assists in the cellular uptake of DNA, such as, but not limited to calcium ion. These agents are generally referred to as transfection facilitating reagents and pharmaceutically acceptable carriers. Those of skill in the art will be able to determine the particular reagent or pharmaceutically acceptable carrier as well as the appropriate time and mode of administration.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Construction of TERT Fusion Proteins

To determine if fusion of the telomerase reverse transcriptase (TERT) antigen to the LTB subunit of *E. coli* heat labile enterotoxin (Fingerut et al. *Vaccine* 23(38): 4685-96 (2005); Rigano et al. *Plant Cell Rep.* 22(7): 502-8 (2004)) could enhance the immunogenicity of TERT alone, vectors were constructed encoding the full-length telomerase reverse transcriptase, with modifications. First, the DNA sequence was codon-optimized to incorporate codon preferred by human host cells. Additionally, to ensure that the encoded antigen was safe for vaccine use, mutations were introduced to the TERT nucleotide sequence to inactivate telomerase catalytic activity of the encoded protein. Specifically, the mutations D712A and V713I were added to the human TERT sequence and the mutations D702A and V703I were added to the mouse TERT sequence (Arai et al. Two independent regions of human telomerase reverse transcriptase are important for its oligomerization and telomerase activity. *J. Biol. Chem.* 277 (10): 8538-44 (2002)).

TERT fusions were engineered by joining the C-terminal end of the modified TERT nucleotide sequences, described above, to a nucleotide sequence encoding a modified LTB (nt 64 to 375) in which the signal peptide coding sequence had been removed. Additionally, a leader sequence encoding the human tissue plasminogen activator (TPA) signal sequence was added 5' to the TERT-encoding nucleotide sequence to ensure the secretion of the TERT protein (Haddad et al. Comparative study of DNA-based immunization vectors: effect of secretion signals on the antibody responses in mice. *FEMS*

*Immunol. Med. Microbiol.* 18(3): 193-202 (1997)). The entire sequence was codon-optimized to incorporate codons preferred by human host cells using computer algorithms. The synthetic codon optimized gene was assembled by synthetic oligonucleotides. In the final construct, two amino acids were added (S and R) between the TERT sequence and the LTB sequence due to the cloning strategy.

The nucleotide sequences encoding the TERT-fusions were cloned into the vector pV1JnsA under the control of the human cytomegalovirus (CMV)/intron A promoter plus the bovine growth hormone (BGH) polyadenylation signal. Plasmid pV1J/TPA-hTERT-LTB opt carries the codon-optimized, inactivated, cDNA of human TERT fused to the coding sequences of the TPA signal sequence on the N-terminal end and LTB on the C-terminal end. Similarly, plasmid pV1J/TPA-mTERT-LTBopt carries the codon-optimized, inactivated, cDNA of mouse TERT fused to TPA and LTB.

EXAMPLE 2

Plasmid and Adenovirus Constructs pV1JnsA/TPA-mTERT (AI)-LTBopt: Plasmid 041046pucKana containing TPA-mTERT(AI)-LTB sequence was obtained from GENEART (Geneart GmbH, Regensburg, Germany). The plasmid was digested with BglII and SalI and the resulting fragment was cloned into the BglII/SalI site in the plasmid pV1JnsA (Montgomery et al., *DNA Cell Biol.*, 12(9):777-83 (1993)).

pV1JnsA/mTERT(AI)opt: pV1JnsA/TPA-mTERT(AI)-LTB was digested XbaI to remove LTB coding sequence (present between two XbaI sites) the resulting construct pV1JnsA/TPA-mTERT(AI) had 3 aa (S;R;N) after the last mTERT aa and before the stop codon. Removal of the TPA coding sequence was performed on pV1JnsA/TPA-mTERT (AI) by BamHI and EcoRV digestion. The TPA coding sequence was replaced by a PCR product obtained amplifying mTERT sequence with the sense primer (5'-G A T C T G A T G A T A T C G C C A C C A T G A C C A G A G C C C C C A G A T G-3; SEQ ID NO: 15) and anti-sense primer (5'-A G G G G G G A T C C G C A C A C C T G G T A G G C G C A G C T G G G-3'; SEQ ID NO:16) and cloned back into the BamHI and EcoRV digested vector.

pV1JnsA/TPA-hTERT(AI)-LTBopt: The synthetic fragment corresponding to TPA-hTERT(AI)-LTB obtained by GENEART was cloned into pV1JnsA using BglII/SalI restriction sites.

Ad6-TPAmTERT(AI)-LTBopt: Plasmid 041046pucKana containing TPA-mTERT(AI)-LTBopt sequence was obtained from GENEART. The plasmid was digested with BglII and SalI and the fragment cloned BglII/SalI into the plasmid pNEBAd6-CMVpA shuttle vector. The plasmid pNEBAd6-CMVpA-TPA-mTERT(AI)-LTB digested with EcoRI/HindIII was recombined to ClaI-linearized plasmid pMRK Ad6 ΔE1 ΔE3. The plasmid was cut with PacI to release the Ad ITRs and transfected in Perc-6 cells. Ad6 vector amplification was carried out by serial passages and purified trough standard CsCL gradient purification.

Ad6-hTERT(AI): Plasmid pCRsript containing wild type sequence of hTERT (hTERT wild type sequence was rescued by reverse transcription of mRNA of human tumor cells) was digested BglII/XbaI filled with Klenow enzyme and cloned in pV1JnsA digested with EcoRV and BglII. pV1JnsA-hTERT was mutagenized by using an oligonucleotide (5'-C T G T A C T T T G T C A A G G T G G C T A T C A C G G G C G C G T A C G-3'; SEQ ID NO:17) and the Stratagene quikchange multi site-directed mutagenesis kit (Stratagene, LA Jolla, Calif.; Cat: 200513) to obtain pV1JnsA-hTERT(AI). The plasmid was digested with BglII and SalI and the fragment cloned BglII/SalI into the plasmid pNEBAd6-CMVpA shuttle vector. The plasmid pNEBAd6-CMVpA-hTERT(AI) was digested PacI/PmeI and recombined to ClaI-linearized plasmid pMRK Ad6 ΔE1 ΔE3. The plasmid was cut with PacI to release the Ad ITRs and transfected in Perc-6 cells. Ad6 vector amplification was carried out by serial passages and purified trough standard CsCL gradient purification.

EXAMPLE 3

IFN-γ ELISPOT Assay

Mouse splenocytes secreting IFN-γ in an antigen-specific manner were detected using a standard enzyme-linked immunospot (ELISPOT) assay (Miyahira et al. *J Immunol Methods* 181(1): 45-54 (1995)). Ninety-six wells MAIP plates (Millipore Corp., Billerica, Mass.) were coated with 100 µl/well of purified rat anti-mouse IFN-γ (IgG1, clone R4-6A2, Pharmingen) diluted to 2.5 µg/ml in sterile PBS. After washing with PBS, blocking of plates was carried out with 200 µl/well of R10 medium for 2 hrs at 37° C.

Splenocytes were obtained by removing the spleen from the euthanized mice in a sterile manner, followed by spleen disruption through grating on a metal grid. Red blood cells were removed by osmotic lysis by adding 1 ml of 0.1× PBS to the cell pellet and vortexing for approximately 15s. One ml of 2× PBS was then added and the volume was brought to 4 ml with 1× PBS. Cells were pelleted by centrifugation at 1200 rpm for 10 min at RT, and the pellet was resuspended in 1 ml R10 medium. Viable cells were counted using Türks staining.

Splenocytes were plated at $5 \times 10^5$ and $2.5 \times 10^5$ cells/well in duplicate and incubated for 20 h at 37° C. with 1 µg/ml suspension of each peptide. Concanavalin A (ConA) was used as positive internal control for each mouse at 5 µg/ml. After washing with PBS, 0.05% Tween 20, plates were incubated O/N at 4° C. with 50 µl/well of biotin-conjugated rat anti-mouse IFNγ (RatIgG1, clone XMG 1.2, PharMingen) diluted to 1:2500 in assay buffer. After extensive washing, plates were developed by adding 50 µl/well NBT/B-CIP (Pierce) until development of spots was clearly visible. The reaction was stopped by washing plates thoroughly with distilled water. Plates were air dried and spots were then counted using an automated ELISPOT reader.

A similar protocol was performed to monitor immune responses in Rhesus monkeys. Briefly, peripheral blood mononuclear cells (PBMCs) were isolated from 8-10 ml of blood collected in EDTA-containing Vacutainer tubes (Becton Dickinson, Franklin Lakes, N.J.). Lymphocytes were isolated using density gradient centrifugation in Accuspin columns (Sigma, St. Louis, Mo.). After red blood cells were lysed with ACK lysis buffer, the cell pellet was washed with PBS and R10. Finally, cells were re-suspended in 0.5 ml R10 medium. The lymphocytes were counted using a Coulter counter and the volume adjusted to $1 \times 10^7$ cells/ml.

EXAMPLE 4

Intracellular Cytokine Staining

One to two millions mouse splenocytes or PBMC obtained by retroorbital bleeding in EDTA were resuspended in 1 ml RPMI 10% FCS were incubated with pool of peptides (5-6 µg/ml final concentration of each peptide) and brefeldin A (1 µg/ml; BD Pharmingen cat #555028/2300kk) at 37° C. and 5% $CO_2$ for 12-16 hours. Cells were then washed with FACS buffer (PBS1% FBS, 0.01% $NaN_3$) and incubated with purified anti-mouse CD16/CD32 Fc block (BD Pharmingen cat #553142) for 15 min at 4° C. Cells were then washed and stained with surface antibodies: CD4-PE conjugated anti-mouse (BD Pharmingen, cat.# 553049), PercP CD8 conjugated anti mouse (BD Pharmingen cat# 553036) and APC-conjugated anti-mouse CD3e (BD Pharmingen cat# 553066) for 30 minutes at room temperature in the dark. After the washing cells were fixed and permeabilized with Cytofix- Cytoperm Solution (BD Pharmingen cat #555028/2300kk) for 20 min at 4° C. in the dark. After washing with PermWash Solution (BD Pharmingen cat #555028/2300kk) cells were incubated with the IFNγ-FITC antibodies (BD Pharmingen). Cells were then washed, fixed with formaldehyde 1% in PBS and analyzed on a FACS-Calibur flow cytometer, using CellQuest software (Becton Dickinson, San Jose, Calif.).

EXAMPLE 5

Cytotoxic T Lymphocyte (CTL) Assay

Splenocytes were obtained by removing the spleen from the euthanized mice in a sterile manner, followed by spleen disruption through grating on a metal grid. Red blood cells were removed by osmotic lysis by adding 1 ml of 0.1× PBS to the cell pellet and vortexing for approximately 15s. Spleen cells at $2 \times 10^6$ cells/ml in R10 were plated in a 24 well cell culture plate (2 ml of cells/well) in presence of the immunogenic peptide at the final concentration of 10 µg/ml. Plates were incubated at 37° C., 95% humidity, 5% $CO_2$ for 6 days. At day 3 of culture, recombinant human IL-2 at a final concentration of 10 U/ml was added.

Target cells growing at exponential phase were harvested and brought to $1 \times 10^6$ cells/ml/tube in the presence of the immunogenic peptide at 10 µg/ml final concentration. Cells were labeled with 50-100 µCi $^{51}$Cr/tube at 37° for 2 hours. Target cells were washed three times with 10 ml medium by centrifuging at 250 g, room temperature for 5 min, and brought at $1 \times 10^5$ cells/ml.

CTL assay was performed by plating Effector/Target cells with E/T ratio at 100:1, 50:1, 25:1 and 12.5:1. After 4 hours of incubation, plates were centrifuged at 1200 rpm for 5 min and the supernatant was harvested (30 µl/well). Plates were dried overnight and counted using a Beta-plate counter.

EXAMPLE 6

Immunization

Female C57BL/6 mice (H-2b) were purchased from Charles River (Lecco, Italy). HLA-A2.1 mice (HHD) were kindly provided by F. Lemmonier (Institute Pasteur, Paris, France). BALB/c mice (H-2d) were purchased from Charles River (Lecco, Italy). Mice were immunized at 8 weeks of age. Fifty micrograms of plasmid DNA were electroinjected in a 50 µl volume in mice quadriceps as previously described (Rizzuto et al. *Proc. Natl. Acad. Sci. U.S.A.* 96(11): 6417-22 (1999)). Electroporation (EP) was performed as previously described (Zucchelli et al. *J. Virol.* 74(24): 11598-607 (2000); Rizzuto et al., supra). Briefly, electrical shock consisted of 10 trains with 1000 square bipolar pulses (90V/cm, 75 mA, 200 µs/phase). Ad injections were carried out in mice quadriceps in 50 µl volume. Cell mediated immune response was analyzed at the indicated time.

Rhesus monkeys were vaccinated 5 times by DNA-EP (5 mg/injection) every two weeks. The electrical conditions applied for DNA delivery in rhesus quadriceps consisted of 2 trains of 100 square bipolar pulses (50 V/cm, 100 mA 200 µs/phase). After four additional weeks, monkeys were boosted with Ad (10E11 vp) two times, with a two week interval between the doses. Ad injections were performed intramuscularly in the rhesus quadriceps in 0.5 ml volume of PBS.

EXAMPLE 7

Genetic Vaccination with Plasmid DNA Coding for TPA-mTERT(AI)-LTB Breaks Immune Tolerance To determine if vaccination of mice with TPA-mTERT (AI)-LTB could break immune tolerance, groups of 20 BALB/c mice were immunized with 5 weekly injections of plasmid pV1J/TPA-mTERT(AI)-LTB followed by electroporation, as described in EXAMPLE 6. Eleven days after the last injection, splenocytes were obtained from individual mice, which were used to analyze the cell-mediated immune response by IFN-γ ELISPOT assay and by intracellular cytokine staining (ICS).

Antigen-specific IFNγ secretion from stimulated splenocytes was measured using three pools of 15mer mTERT peptides overlapping by 11 aa and encompassing the entire mTERT protein. The mTERT-1 pool was composed of 94 individual peptides covering the mTERT region from aa 1 to 388. The mTERT-2 pool was composed of 106 individual peptides covering the mTERT region from aa 377 to 811. The mTERT-3 pool was composed of 78 individual peptides covering the mTERT region from aa 801 to 1122. As a negative control, cytokine production was also measured upon stimulation of the splenocytes with DMSO at the same concentration utilized to solubilize the TERT peptides. The immune response induced against the LTB adjuvant was also detected by using a pool of 24 individual 15-mer peptides overlapping by 11 aa and covering the entire LTB sequence. ELIspot results indicate that vaccination of mice with TPA-mTERT (AI)-LTBopt elicited a cell mediated immune response (CMI) against the N-terminal and central regions of the TERT protein, contained within the TERT-1 and TERT-2 peptide pools (FIG. 3). CMI against LTB was also detected by ELIspot (FIG. 3).

Figure 4:
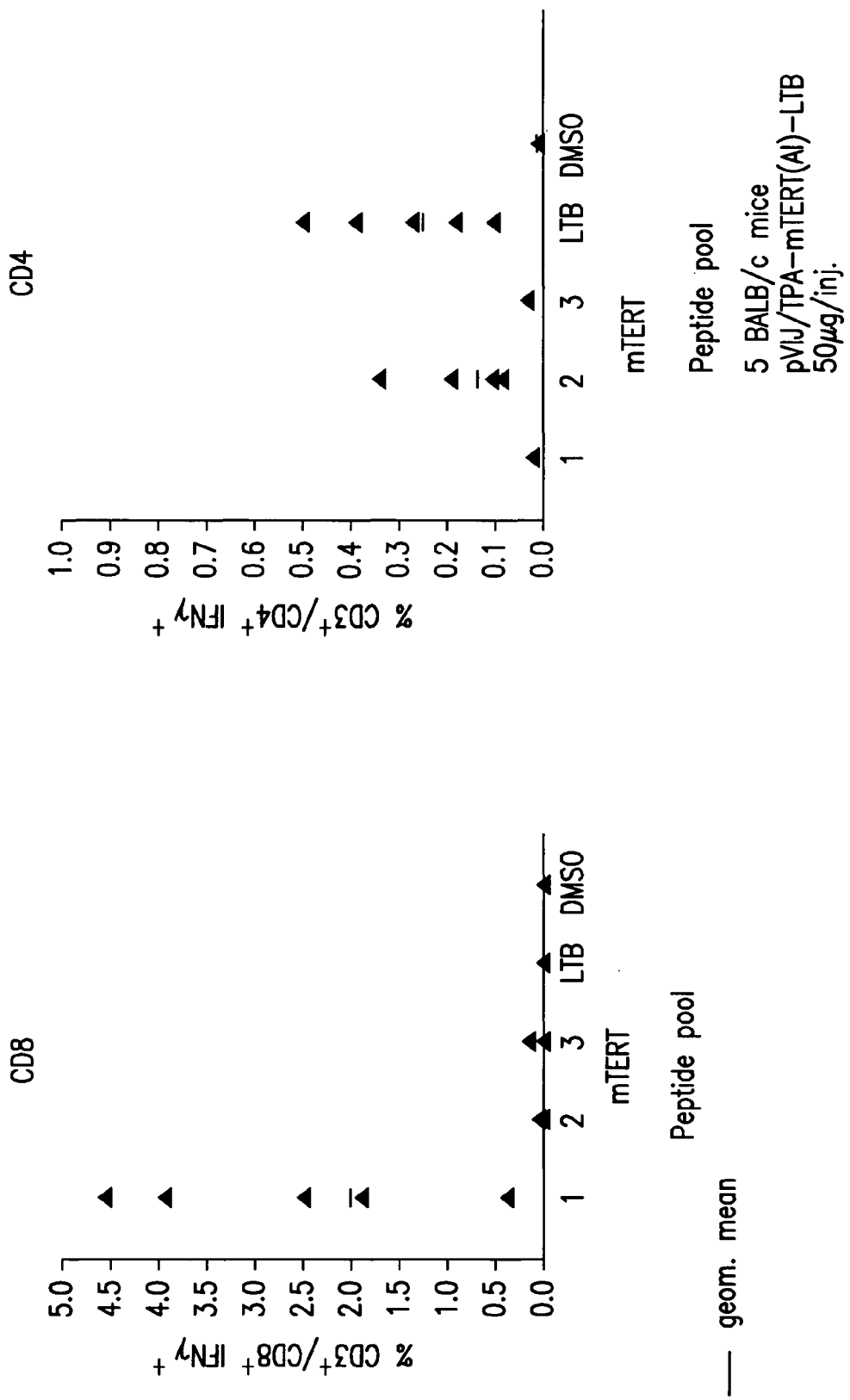
FIG. 4 shows results from IFNγ intracellular staining on splenocytes from vaccinated BALB/c mice. CD4+ and CD8+ T cell response to mouse TERT was measured using pools of overlapping peptides that cover the entire protein. Immune response to LTB was also monitored. Data plotted are from 6 individual mice (filled triangles). Geometric mean values are indicated (straight line). No T cell response to TERT was detected in mock treated mice (not shown). See EXAMPLE 7.

To better characterize the T cell response elicited by the plasmid pV1J/TPA-mTERT(AI)-LTBopt and to identify the CD8+ and CD4+ T cell subset responsible for IFN-γ production, IFN-γ intracellular staining was carried out on vaccinated mice splenocytes and analyzed by FACS. Data obtained by ICS demonstrate that genetic immunization of BALB/c mice vaccinated with TPA-mTERT(AI)-LTBopt elicited a significant CD8$^+$T cell response against the N-terminal region of the TERT protein (contained within mTERT-1 peptide pool, see FIG. 4). The CD4$^+$ T cell response was mapped in the central region of TERT (mTERT-2 peptide pool). In contrast, no CMI could be detected in these mice against the C-terminal region of the protein (mTERT-3 peptide pool). A CD4$^+$ T cell response against LTB was also detected (FIG. 4).

To further map the CD8+T-cell response, a midi pool of mTERT 15 mer peptides was used. Each midi pool contained ten 15 mers, which were each individually contained in a separate midi-pool. Therefore, a positive reaction of 2 midi pools would unequivocally identify one individual 15 mer as being immunogenic. Because CD8+ epitopes are always 9aa long, any CD8+ peptide is contained in two adjacent 11 mer peptides. Results demonstrated that the CD8+ T-cell immune response was localized to the TERT region included in the following 15 mer mTERT peptides: mTERT-41 (TERTaa161; LVPPSCAYQVCGSPL (SEQ ID NO:18) and mTERT-42 (TERTaa165; SCAYQVCGSPLYQIC; SEQ ID NO:19). By overlapping the two 15 mer peptides (mTERT41 and mTERT-42), three possible reactive nonamers were synthesized and tested in ICS. Finally, the immunodominant CD8$^+$ epitope in BALB/c mice was identified in the following sequence (mTERTaa167; AYQVCGSPL; SEQ ID NO:20). These results demonstrate that vaccination of BALB/c mice with pV1J/TPA-mTERT-LTB could break immune tolerance to the mTERT antigen.

Figure 6A:
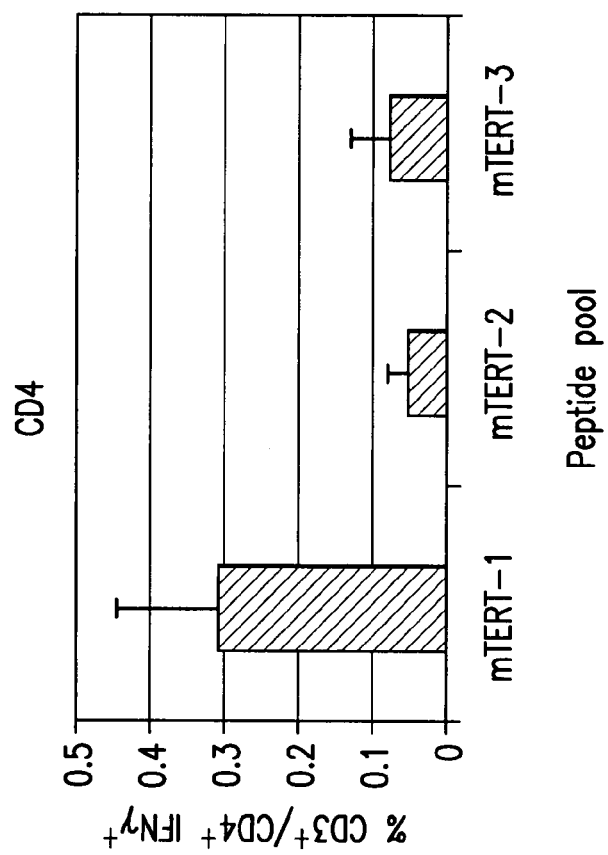
FIG. 6 shows the induction of an immune response to mouse TERT. C57BL/6 mice were immunized with 5 weekly injections of plasmid pV1J/TPA-mTERT(AI)-LTBopt. Immune response was assessed on mouse splenocytes by IFNγ ELIspot assay using mouse TERT peptide pools. Antigen specific CD4+ and CD8+T cell responses are shown as geometric mean values obtained from 6 immunized mice, standard deviation is also indicated. See EXAMPLE 7.
Figure 6B:
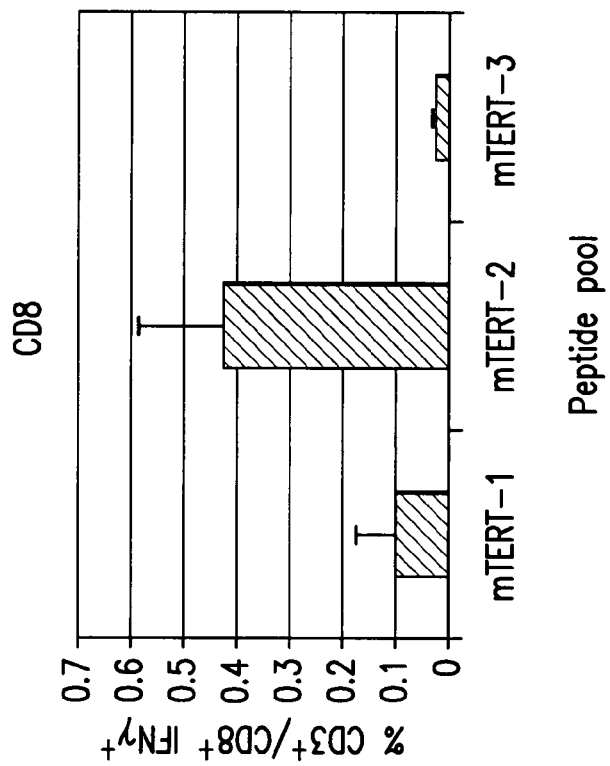

To confirm data obtained in BALB/c mice, C57BL/6 (B6) mice were also immunized with 5 weekly injections of plasmid pV1J/TPA-mTERT(AI)-LTBopt. IFN-γ intracellular staining was carried out on vaccinated mice splenocytes and analyzed by FACS. Similar to results obtained with BALB/c mice, tolerance against mTERT was broken in all B6 mice. Additionally, both CD4$^+$ and CD8$^+$T cells producing IFNγ were detected by ICS upon stimulation with TERT peptides (see FIG. 6).

The CD8+ immune response elicited by DNA vaccination in C57BL/6 mice was primarily biased towards the central region of the TERT protein (peptide pool mTERT-2). A weaker CD8+ immune response was also detectable in the mTERT peptide pool-1. The CD8+ immune response was mapped in B6 mice using midi pools as described above. Two CD8+ epitopes were identified in B6. The first immunogenic sequence was mapped to the aa sequence mTERT198 (VGRNFTNL; SEQ ID NO:21) and the second CD8+ epitope was mapped to the sequence mTERT486 (SLGKYGKL; SEQ ID NO:22) Additionally, the CD4+ immune response was localized to the N-terminal region of TERT (peptide pool mTERT-1). No immune response was detected against the C-terminal region of mTERT.

Similar to the results obtained with BALB/c mice described above, immunization and analysis of the subsequent immune response of B6 mice confirm that TPA-mTERT(AI)-LTBopt immunization can break immune tolerance to the mTERT antigen. Therefore, taken together, results obtained with BALB/c and B6 mice indicate that the TPA-mTERT(AI)-LTBopt fusion is a potent immunogen in the self context independently from the mice strain used.

EXAMPLE 8

Cytolytic Activity of TERT-Specific CD8+T Cells

A cytotoxic T-lymphocyte (CTL) assay was used to detect the cytolytic activity of TERT-specific CD8+T cells elicited by immunization of BALB/c mice with pV1J/TPA-mTERT(AI)-LTBopt. Mice were immunized with 5 weekly injections of plasmid pV1J/TPA-mTERT(AI)-LTBopt followed by electroporation. Mice splenocytes obtained from 2 individual mice were collected 10 days after the last immunization. These splenocytes were stimulated for one week with the immunogenic peptide mTERTaa167 (AYQVCGSPL; SEQ ID NO:20) to obtain in vitro activated T cells. The BALB/c syngenic tumor cell line 4T1 (Aslakson et al. Cancer Res. 52(6): 1399-405 (1992)) was used as a target. 4T1 cells were loaded with the immunoreactive peptide and labeled with $Cr^{51}$ to be used as target for the CTL assay. The activated T cells were co-incubated with the target 4T1 cells at different effectors/target ratio. Activated T cells obtained both from mouse# 1 and mouse #2 showed cytolytic activity on target cells when loaded with the immunogenic peptide mTERTaa167 (AYQVCGSPL; SEQ ID NO:20). The two mice showed different degrees of cytotoxic activity ranging from 80% (mouse #1) to 25% (mouse #2) at effectors/target ratio of 50/1.

Figure 5:
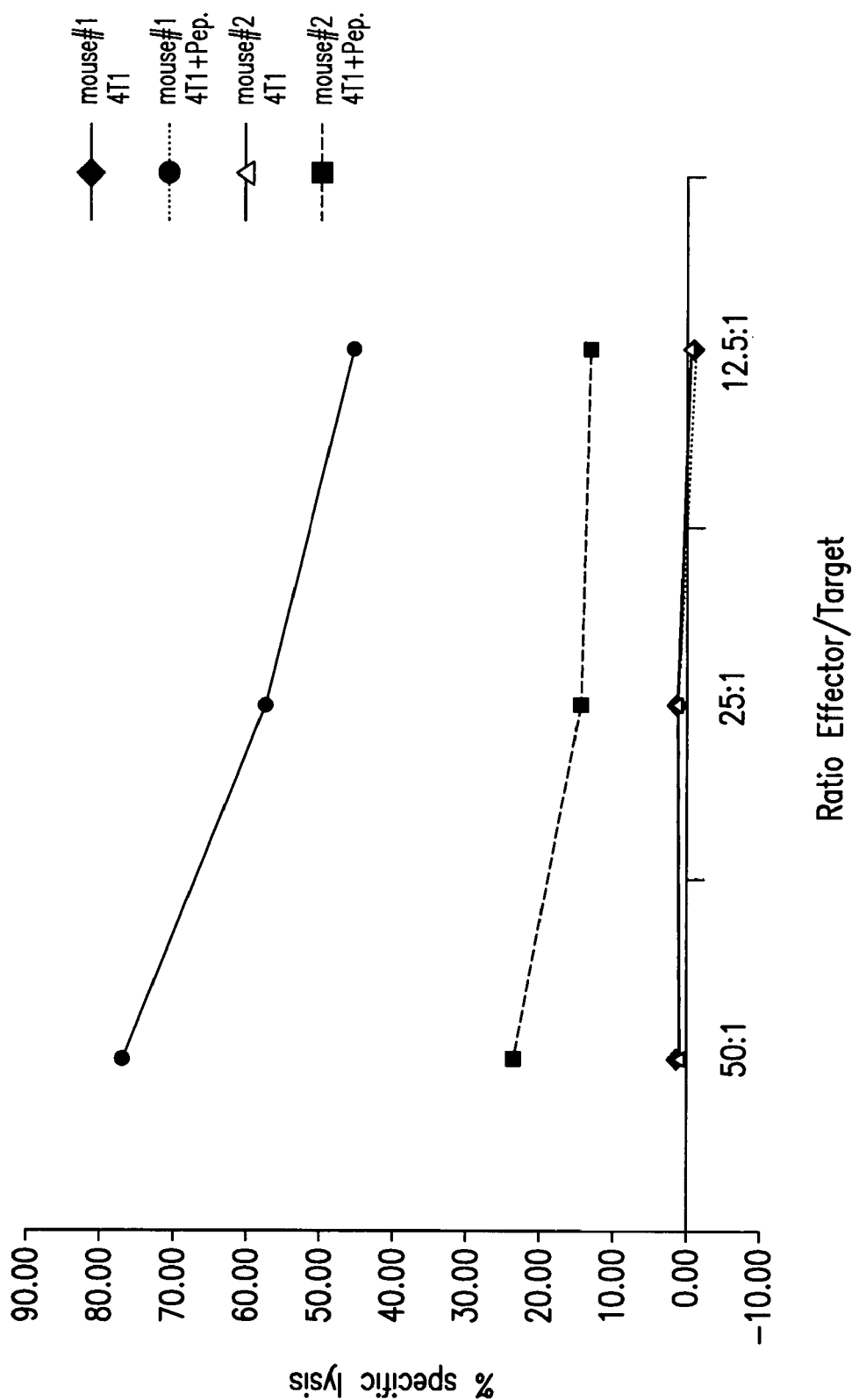
FIG. 5 shows the results of $^{51}$Cr Release CTL killing by effector T cells of 4T1 target cells pulsed with CD8+T cells specific peptide mTERTaa167 (AYQVCGSPL; SEQ ID NO:20). Effector cells were prepared from splenocytes of two immunized BALB/c mice and were re-stimulated in vitro with the specific peptide. Results are expressed as percentage of specific killing at different Effectors/Target ratio. See EXAMPLE 8.

Results indicate that a cytotoxic immune response was induced upon DNA immunization with TPA-mTERT(AI)-LTBopt as self antigen in BALB/c mice (FIG. 5).

EXAMPLE 9

Comparative Immunogenicity of TPA-mTERT(AI)-LTBopt Construct

To compare the immunogenicity of the secreted mTERT(AI) protein fused to LTB encoded by pV1J/TPA-mTERT(AI)-LTBopt, to a non-secreted version of mTERT(AI) without fusion to LTB, a plasmid pV1J derivative carrying mTERT(AI) was constructed, as described in EXAMPLE 2.

Groups of 6 BALB/c mice were immunized with 5 weekly injections of plasmids pV1J/TPA-mTERT(AI)-LTBopt or pV1J/mTERT(AI)opt. The immune response was monitored by IFNγ intracellular staining using the mTERTaa167 CD8+ immunodominant epitope sequence previously identified for BALB/c mice (AYQVCGSPL (SEQ ID NO:20).

Figure 7:
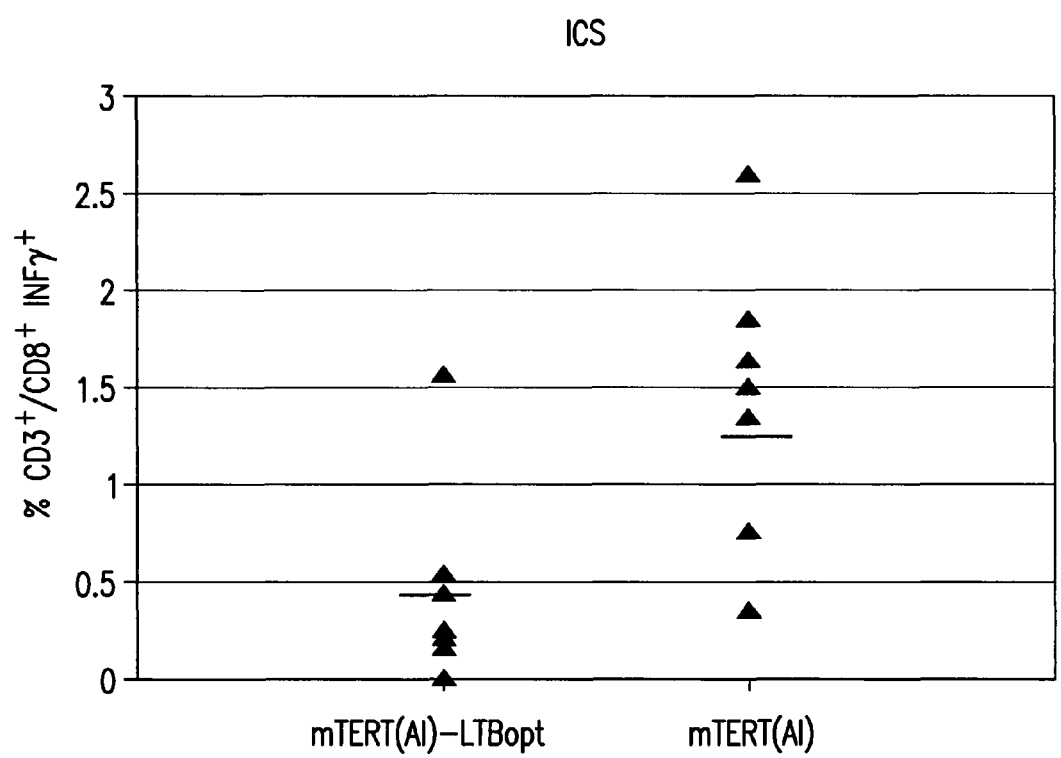
FIG. 7 shows the induction of an mTERT specific immune response in BALB/c mice. Mice were immunized with 5 weekly injections of the constructs pV1J-mTERT(AI)opt or pV1J-TPAmTERT(AI)-LTBopt. Immune response was determined by IFNγ intracellular staining on PBMC using the CD8+ epitope corresponding to the peptide sequence mTERTaa167 (AYQVCGSPL; SEQ ID NO:20). Data plotted are from 8 individual mice (filled triangles). Geometric mean values are indicated (straight lines).

Results indicate that TPA-mTERT(AI)-LTBopt is a better construct for the induction of a CD8+ immune response against murine telomerase than mTERT(AI) (FIG. 7). The difference observed in CD8+T cell response induced in the group immunized by TPA-mTERT-LTB(AI)opt is statistically different from that obtained using the mTERT(AI)opt in the context of DNA immunization (p=0.04 student t test).

EXAMPLE 10

Comparison of Immunization Regimens

The anti-mTERT cell-mediated immune response elicited by immunization of BALB/c mice with DNA TPA-mTERT(AI)-LTBopt plus electrical stimulation alone was compared to the immune response induced by a diversified prime/boost immunization regimen using DNA TPA-mTERT(AI)-LTBopt plus electrical stimulation as prime and Ad6 TPA-mTERT(AI)-LTBopt as final booster of the immune response.

Figure 8:
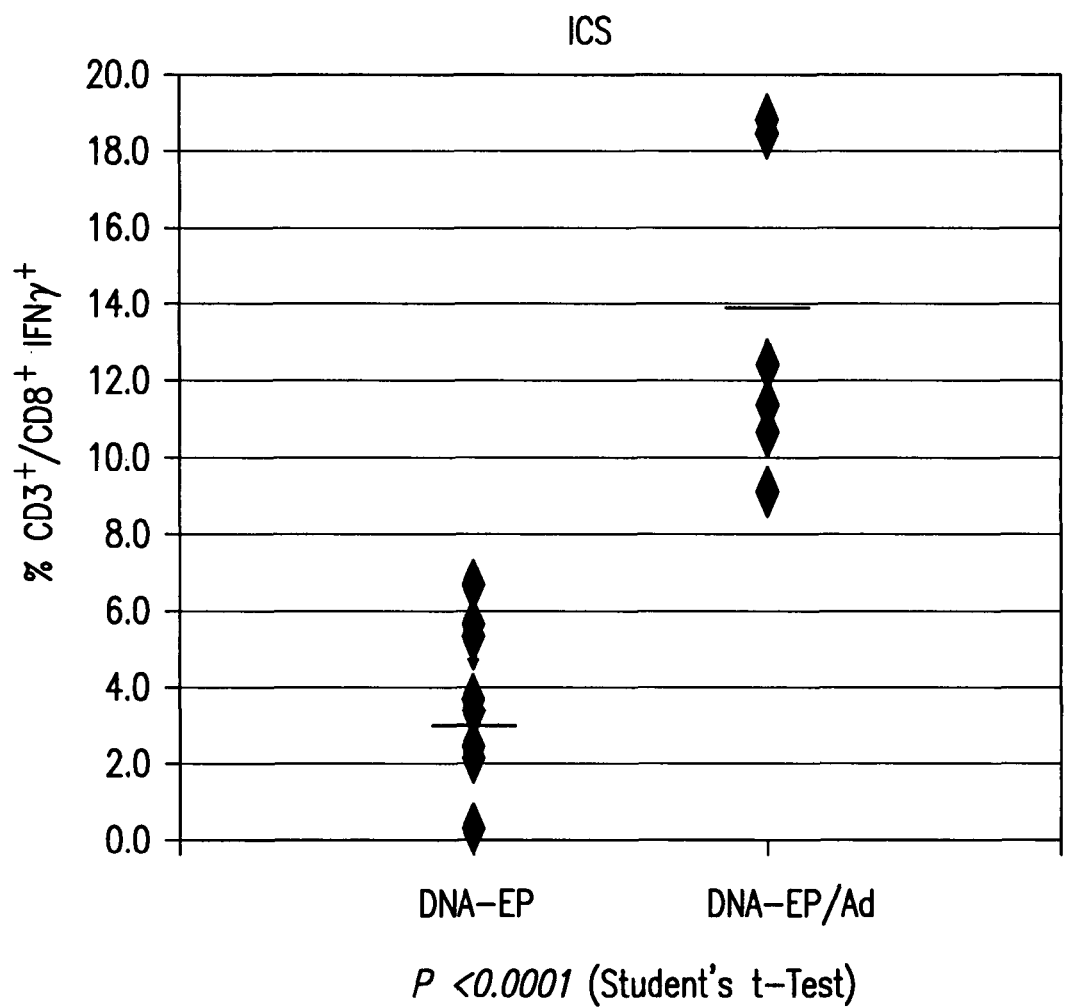
FIG. 8 shows the TERT specific immune response is enhanced upon injection of adenovirus vectors expressing mTERT(AI)-LTBopt. Groups of 10 BALB/c mice were subjected to 5 weekly injections of pV1J/TPA-mTERT(AI)-LTBopt (50 µg/inj.). Two weeks after the last injection of plasmid DNA, mice were either boosted with one additional injection of plasmid DNA (DNA-EP) or with $10^{10}$ vp of Ad6/TPA-mTERT(AI)-LTBopt (Ad). Immune responses to TERT were monitored by IFNγ ICS on PBMC. Data plotted are from 10 individual mice (filled diamonds). Geometric mean values of each group are also shown (straight lines). See EXAMPLE 10.

Groups of 10 mice were immunized with 5 weekly injections of plasmid pV1J/TPA-mTERT(AI)-LTBopt. One week later, a booster injection was given consisting of either one additional injection of 50 μg of DNA plus electroporation (EP) or with $11^{10}$ vp of the Ad6/TPA-mTERT (AI)-LTBopt. IFNγ intracellular staining was performed on mouse PBMCs to assess the resulting cell-mediated immune response. A peptide encompassing a CD8+T cell specific epitope mTERT 167 (AYQVCGSPL; SEQ ID NO:20) which was previously mapped to the N-terminal region of TERT, was used as antigen. Results indicate that the amplitude of the immune response elicited by the DNA-EP/Ad combination was 4.6 fold greater than that which was observed in mice that had received only a DNA-EP regimen (see FIG. 8).

EXAMPLE 11

Vaccination with TPA-mTERT-LTB Controls Tumor Growth

To determine if the mTERT-specific immune response could generate an anti-tumor effect, BALB/c mice were treated with the chemical carcinogen dimethyl hydrazine by intraperitoneal (i.p.) injection prior to vaccination. Treatment of mice with this carcinogen leads to progressive tumor development in the colon characterized by aberrant crypt formation, adenoma, and finally carcinoma. Chemical treatment of these mice did not render them immunocompromized, as immunization with TPA-mTERT(AI)-LTBopt elicited an immune response comparable to that previously found in non-treated mice (data not shown).

Figure 9:
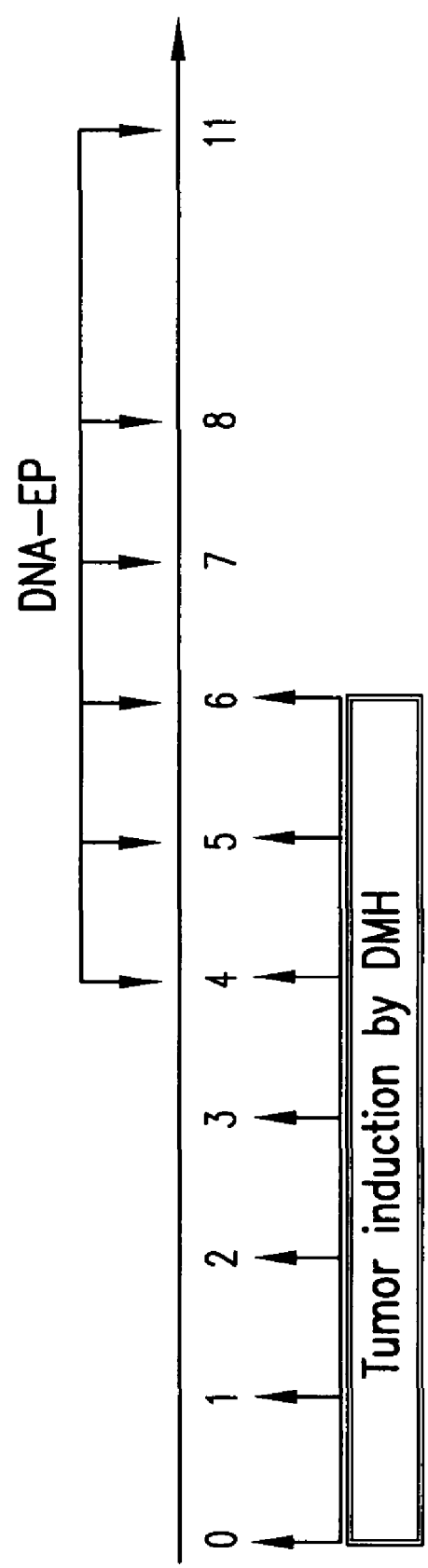
FIG. 9 depicts the protocol utilized to analyze DMH-induced carcinogenesis and vaccination in BALB/c mice. DMH was administered i.p. on a weekly basis. Vaccination with pV1J/TPA-mTERT(AI)-LTBopt was carried out at the indicated time points. Analysis of intestinal lesions was carried out at week 12. See EXAMPLE 11.

To assess the impact of genetic immunization on early stages of DMH induced carcinogenesis, BALB/c mice were treated with DMH and immunized by DNA followed by electroporation (DNA-EP) with pV1J/TPA-mTERT(AI)-LTBopt according to the schedule described in FIG. 9.

Figure 10:
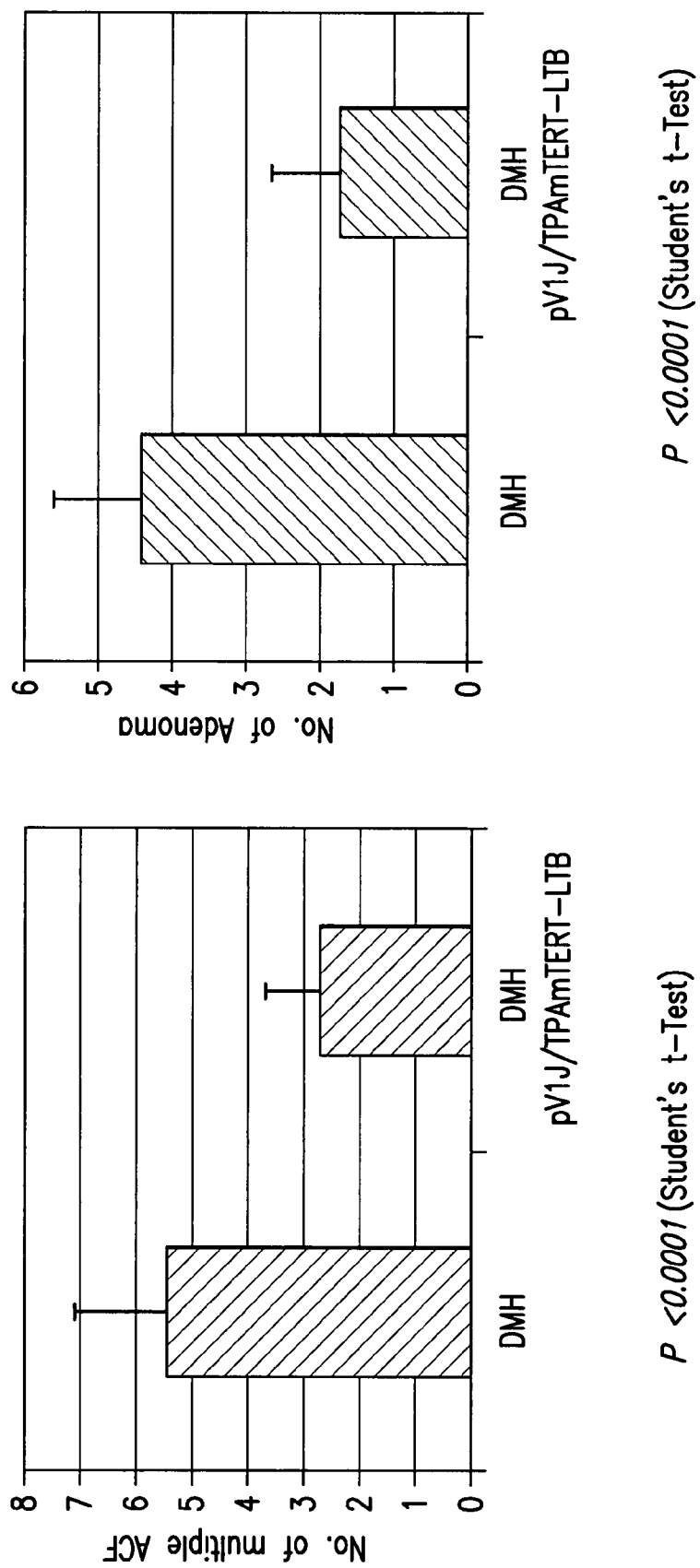
FIG. 10 shows the anti-tumor effect of pV1J/TPA-mTERT (AI)-LTBopt on DMH-induced carcinogenesis. BALB/c mice were treated with DMH and DNA-EP as indicated in FIG. 9. Analysis of ACF and adenoma formation in the colon was carried out at week 12 from the beginning of the treatment. The number of ACF and adenoma in vaccinated mice was compared to that detected in non vaccinated controls. See EXAMPLE 11.

Twenty mice were euthanized 12 weeks after the beginning of DMH treatment to count the number of ACF (aberrant crypt foci) and the number of adenoma which had formed. A significant reduction of both the number of ACF and the number of adenoma present was observed in vaccinated mice compared to non-vaccinated mice (FIG. 10).

Figure 11:
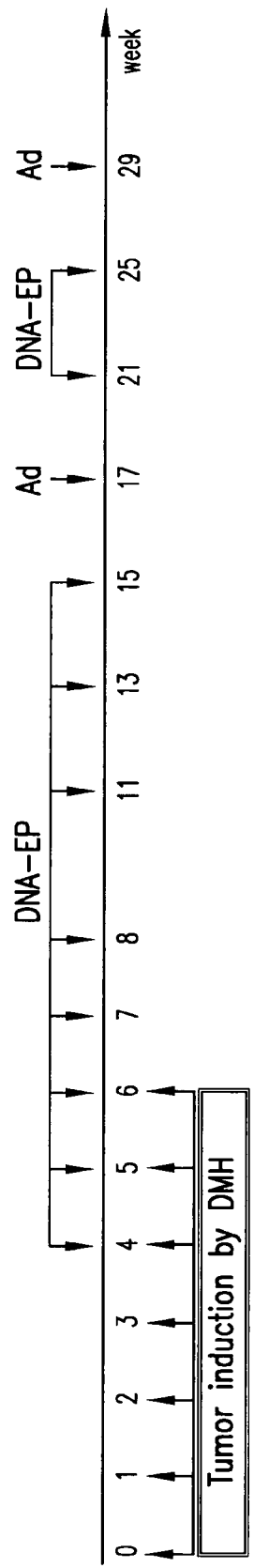
FIG. 11 depicts the protocol utilized to analyze DMH-induced carcinogenesis and vaccination in BALB/c mice. DMH was administered i.p. on a weekly basis. Vaccination with pV1J/TPA-mTERT-LTB DNA and Ad were carried out at the indicated time points. Analysis of the intestinal lesions was carried out at week 30. See EXAMPLE 11.

The efficacy of mTERT vaccination on a later stage of tumor development was also monitored. To enhance and sustain the immune response to mTERT, mice were subjected to repeated DNA-EP TPA-mTERT(AI)-LTBopt and Ad6TPA-mTERT(AI)-LTBopt (FIG. 11). The immune response elicited in these mice was comparable to that detected in BALB/c mice vaccinated with the same DNA/Ad regimen and not treated with DMH.

Figure 12:
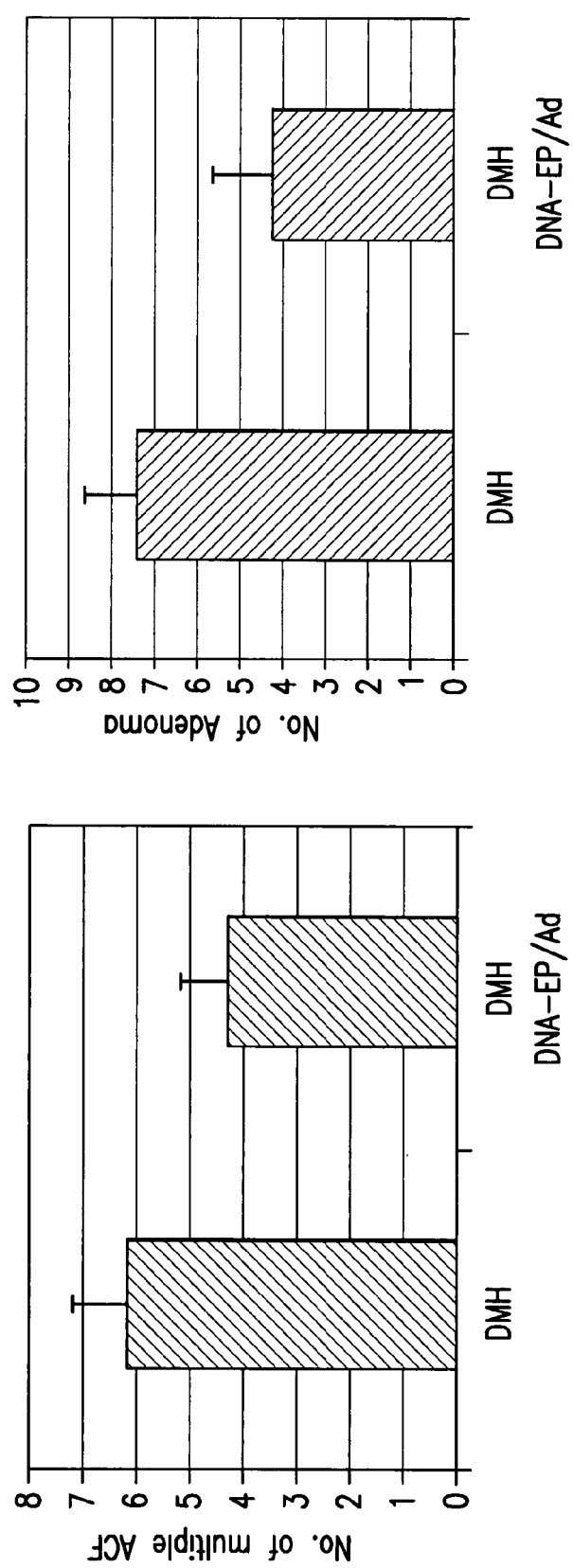
FIG. 12 demonstrates the anti-tumor effect of pV1J/TPA-mTERT(AI)-LTBopt DNA prime/Ad boost on the number of tumor lesions. BALB/c mice were treated DMH and DNA-EP as indicated in FIG. 9. Analysis of ACF and adenoma formation in the colon was carried out at week 30 from the beginning of the treatment. The number of ACF and adenoma in vaccinated mice was compared to that detected in non vaccinated controls. See EXAMPLE 11.

Twenty mice were euthanized 30 weeks after the beginning of DMH treatment to count the number of ACF (aberrant crypt foci) and of adenoma formed. Like results seen with early stage tumor development, a significant reduction in the number of ACF and adenomas was observed in vaccinated mice compared to non-vaccinated mice (FIG. 12).

Figure 13:
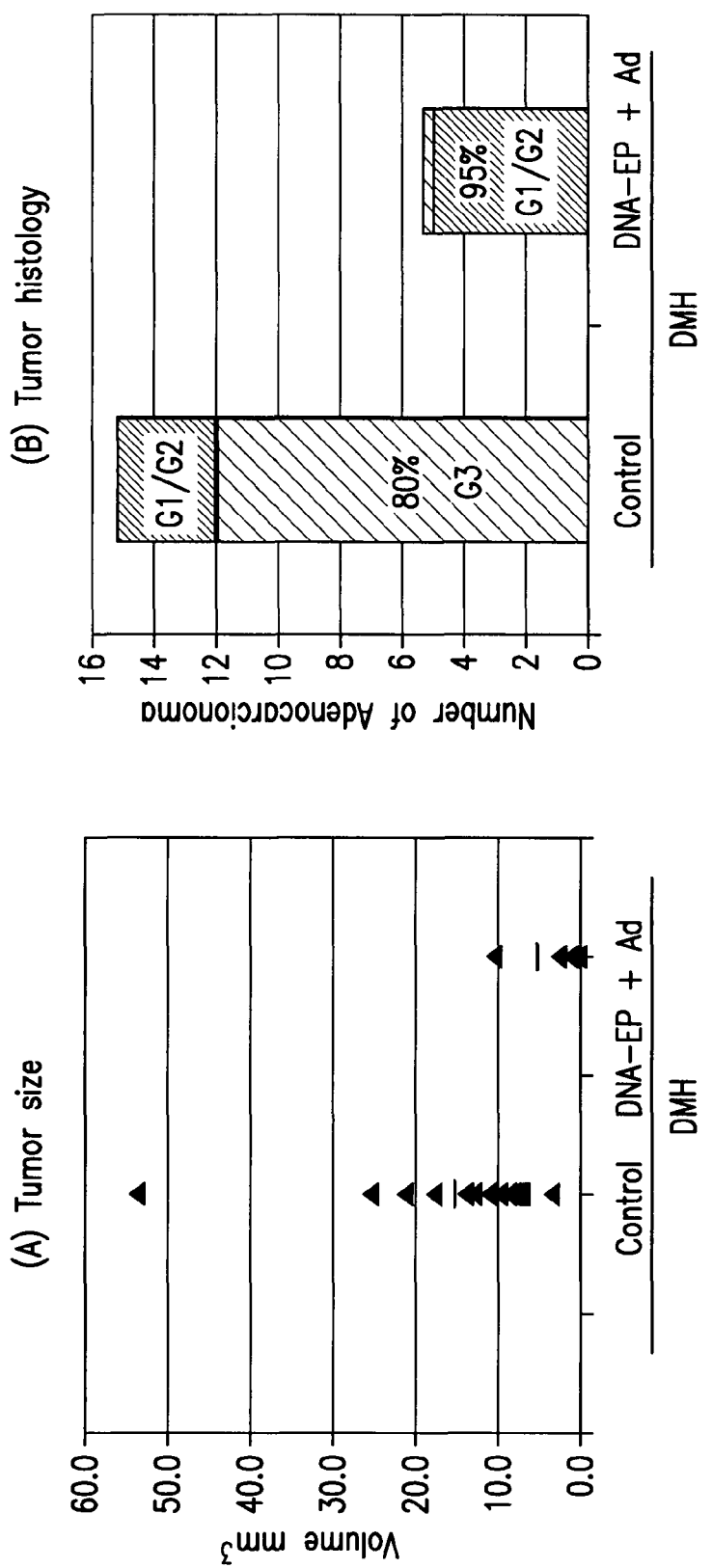
FIG. 13 demonstrates the anti-tumor effect of pV1J/TPA-mTERT-LTB(AI)opt DNA prime/Ad boost on the volume and differentiation stage of tumor lesions. BALB/c mice were treated DMH and DNA-EP as indicated. The volume (Panel A) and histological differentiation stage (Panel B) of colon adenomas present in vaccinated and control mice were analyzed 30 weeks from the beginning of the treatment. Tumors were classified as follows: G1: well-differentiated adenocarcinoma; G2: moderately-differentiated adenocarcinoma; G3: poorly-differentiated adenocarcinoma). See EXAMPLE 11.

Finally, tumors found in vaccinated mice were smaller in volume compared to those found in non-vaccinated mice (FIG. 13A). Moreover, histological analysis showed that the tumors present in vaccinated mice were at a less advanced stage compared to tumors in non-vaccinated animals (FIG. 13B).

EXAMPLE 12

Characterization of pV1JTPA-hTERT(AI)-LTBopt

The immunogenic potential of pV1J/TPA-hTERT(AI)-LTBopt was evaluated in a non-self context since mice transgenic for hTERT are not available. C57BL/6 mice transgenic for the human HLA-A2 (HHD transgenic mice) were utilized so that TERT immunogenic peptides would be presented in the context of human HLA class I. HHD transgenic mice were vaccinated by DNA-EP with 2 biweekly injections of 50 µg of plasmid pV1J/TPA-hTERT(AI)-LTBopt. The induced immune response was evaluated by ICS on mice PBMC. The hTERT immunogenic peptide corresponding to the hTERT 865 epitope RLVDDFLLV (SEQ ID NO:23) was used as antigen. This epitope sequence was previously described as a strong binder for HLA-A2 and inducer of CTL activity in T cells in vitro priming experiments (Dupont et al. *Cancer Research* 65(12): 5417-27 (2005)).

Figure 14:
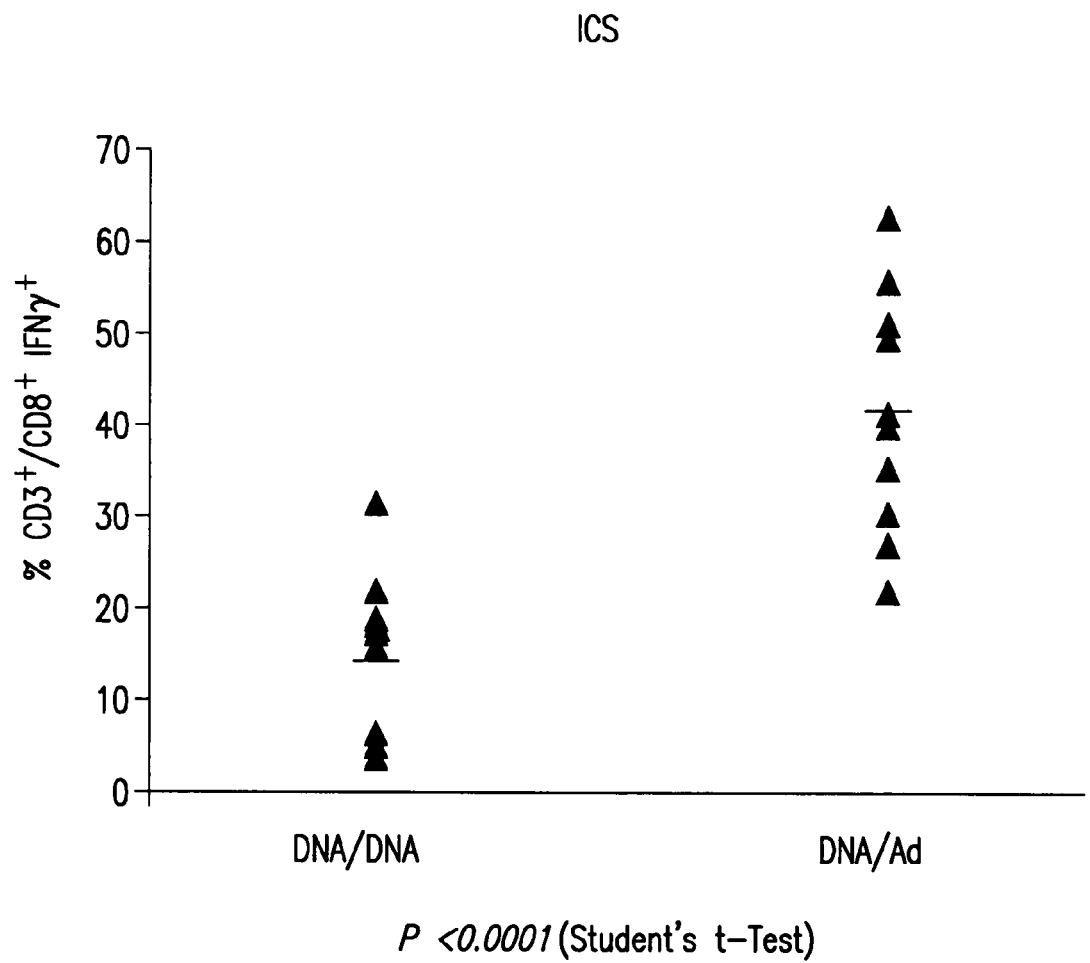
FIG. 14 shows the induction of an immune response to human TERT. HHD transgenic mice were immunized with two biweekly injections (DNA-DNA) of plasmid pV1J/TPA-hTERT(AI)-LTBopt or by one injection of plasmid pV1J/TPA-hTERT(AI)-LTBopt followed, after two weeks by one injection of Ad6hTERT(AI) $10^{10}$ pp (DNA/Ad). The immune response was assessed on mouse PBMC by IFNγ ICS assay. Mice PBMC were incubated with the CD8 immunodominant peptide for HLA-A2 allele hTERT865 (SEQ ID NO:22). Data plotted are from 10 individual mice (filled triangles). Geometric mean values are indicated (straight line). See EXAMPLEs 12 and 13.

Results obtained from 10 mice showed that on average, 12% of CD8+ cells produced IFN-γ when stimulated with the immunogenic hTERT 865 peptide (FIG. 14). Results indicate that the pV1JTPA-hTERT(AI)-LTBopt vaccine candidate is immunogenic and induced a HLA-A2 restricted CD8 immune response.

EXAMPLE 13

Characterization of Immune Response in Vaccinated Mice after Ad6-hTERT(AI) Boost An Ad6 hTERT(AI) construct was assembled as described in EXAMPLE 2. This construct comprises wild-type codons, with the exception of two mutations that were added to abrogate telomerase catalytic activity. An Ad6 hTERT-LTB fusion construct was also made, but could not be rescued, so further testing was performed only with Ad6hTERT(AI).

The Ad6 hTERT(AI) construct was tested for its boosting capability on the immune response induced by DNA-EP in HHD transgenic mice. Groups of 10 mice were vaccinated by DNA-EP with 1 injection of 50 µg of plasmid pV1J/TPA-hTERT(AI)-LTBopt and boosted either with a second DNA injection or with Ad6 hTERT 1010 pp two weeks after the first DNA injection. The induced immune response was measured by using the immunodominant peptide for HLA-A2 allele hTERT865 previously identified. Reactive CD8+ T cells producing IFN-γ were detected with high frequencies. As shown in FIG. 14, the amplitude of immune response elicited by the DNA-EP/Ad combination was 3 fold greater than what observed in mice that had received only a DNA-EP regimen.

The results demonstrated that hTERT specific immune response primed by injection of pV1J/TPA-hTERT(AI)-LTBopt DNA was amplified by boosting it with Ad6-hTERT (AI).

EXAMPLE 14

Characterization of CTL Activity Induced by Immunization with hTERT

Figure 15:
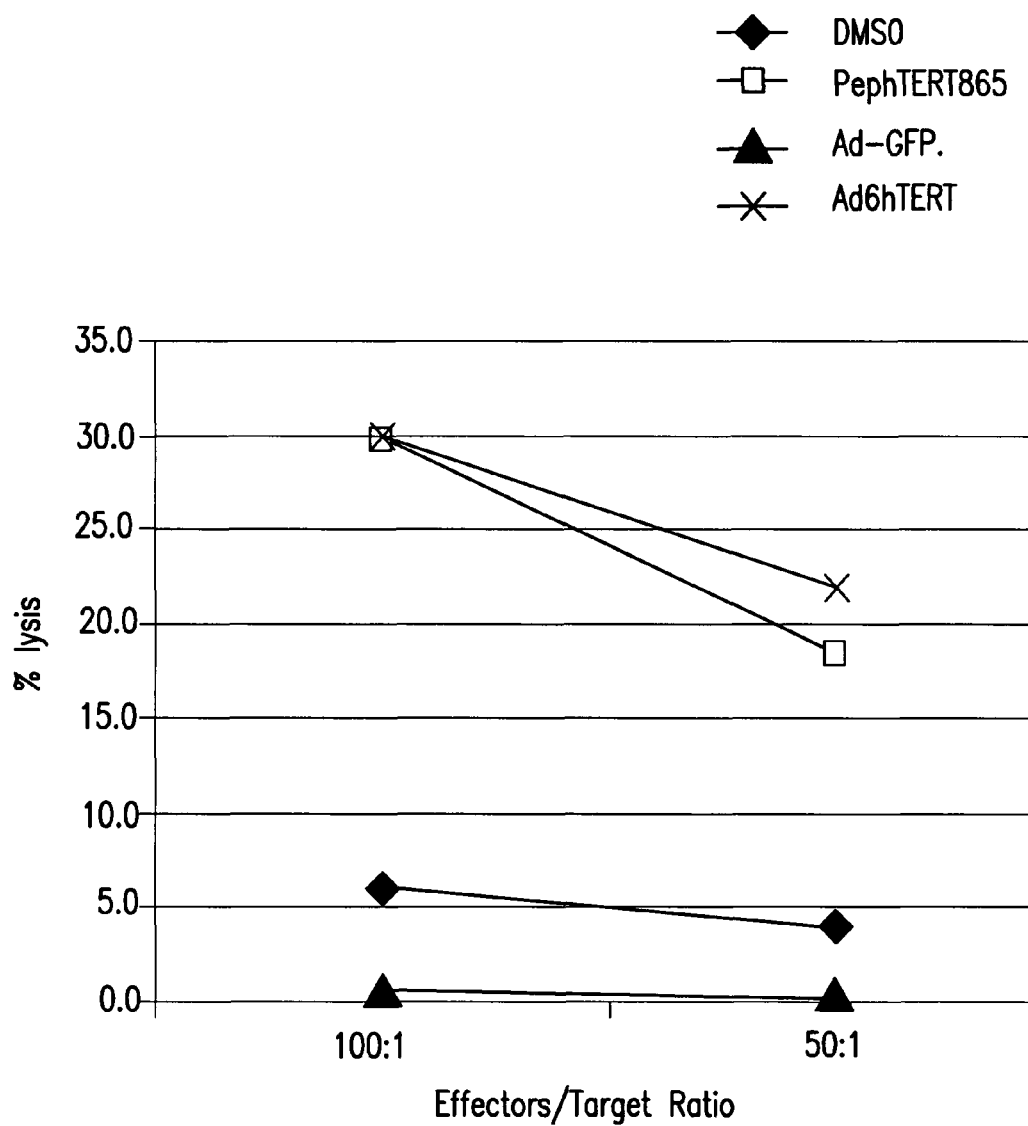
FIG. 15 shows the results of a CTL assay on Cr$^{51}$ labeled target HeLa-HHD cells. CD8+T cells obtained from one immunized mouse were tested in a CTL assay against HeLa-HHD cells, either exogenously loaded with the hTERT865 peptide or w/o peptide but in presence of the DMSO used for the peptide dilution. HeLa-HHD cells were also infected with an Ad vector coding for hTERT or an Ad coding for GFP as control. See EXAMPLE 14.

The CD8+T cell response to hTERT elicited in vaccinated mice was further characterized by testing the cytotoxic activity (CTL) of activated T cells against tumor target cells. Splenocytes from immunized mice were stimulated in culture for 6 days in the presence of the hTERT865 peptide (SEQ ID NO:23; see EXAMPLE 12) and IL-2. Thereafter, activated CD8+T cells were tested against target cells for their lytic activity in a $Cr^{51}$ release assay. HeLa cells stably transfected to express the chimeric MHC class 1 molecule present on HHD mice (HeLa-HHD) were used as target cells. HeLa-HHD target cells were either loaded exogenously with the immunogenic peptide hTERT865 or infected 24 hours before with an Ad6 vector coding for hTERT, in order to endogenously over-express the TERT antigen. As a control, target cells were infected with an Ad6 vector coding for GFP. The results indicate that CD8+T cells induced by the vaccination described were able to kill target cell over-expressing the hTERT antigen (FIG. 15).

EXAMPLE 15

Characterization of Immunogenicity of Human-TERT Vaccine in Rhesus Monkeys

The immunogenicity of the genetic vaccination platform based on DNA prime, Ad boost, with hTERT was evaluated in rhesus monkeys. Because the homology of human TERT and rhesus TERT sequence is 96%, tolerance was expected to play a major role in determining vaccination efficacy.

The vaccination protocol consisted of five injections of DNA-EP (pV1J/TPA-hTERT-LTB, 5 mg/injection), given every two weeks. Four weeks after the last DNA-EP treatment, monkeys were boosted with an Ad vector expressing hTERT (Ad6-hTERT, $10^{11}$ vp)2 times with a two week interval. Data on body weight and clinical signs were collected every week. Negative effects on animal body weight or occurrence of clinical signs were not observed.

The induced immune response was monitored by IFN-γ ELISPOT assay of PBMC using hTERT peptide pools and a peptide pool covering the LTB sequence. Specifically, antigen-specific IFNγ secretion from stimulated cells was measured using three pools of 15 mer hTERT peptides overlapping by 11 aa and encompassing the entire hTERT protein. The hTERT-1 pool was composed of 94 individual peptides covering the hTERT region from aa 1 to 387. The hTERT-2 pool was composed of 94 individual peptides covering the hTERT region from aa 377 to 763. The hTERT-3 pool was composed of 92 individual peptides covering the hTERT region from aa 753 to 1032. As a negative control, cytokine production was also measured upon stimulation of the splenocytes with DMSO at the same concentration used to solubilize the TERT peptides. Immune responses were scored positive if the signal obtained was at least four times higher than the background reactivity (DMSO).

Figure 16A:
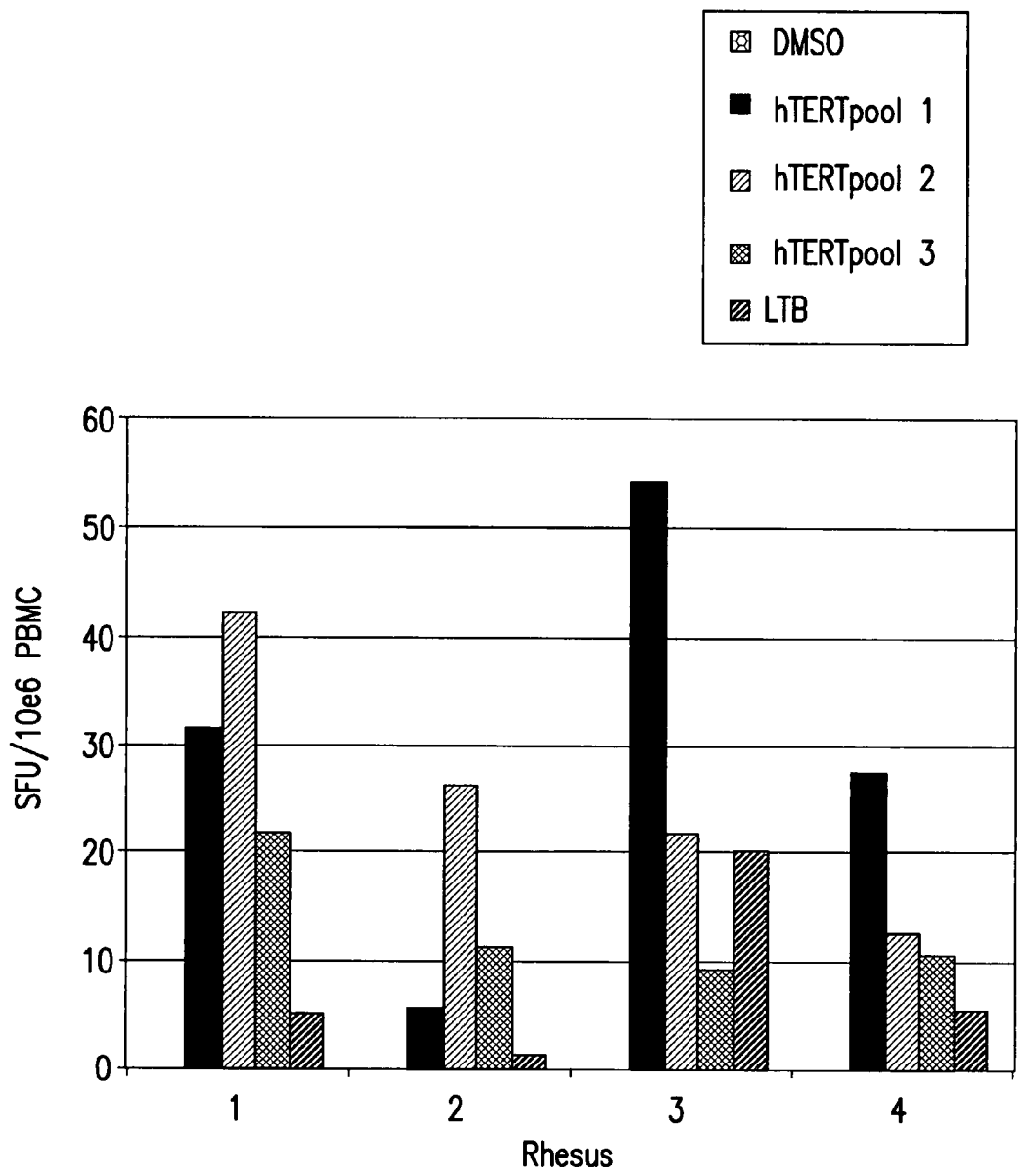
FIG. 16 shows the induction of a cell-mediated immune response to hTERT in rhesus monkeys immunized by DNA-EP. ELIspot analysis was performed on PBMC from hTERT-immunized rhesus monkeys (pV1J/TPA-hTERT(AI)-LTB; DNA-EP/DNA-EP). The assay was performed in duplicate and the average value from the replicates is shown. Analysis performed after the second DNA-EP is shown (Panel A). Analysis performed after the fifth DNA-EP is also shown (Panel B). See EXAMPLE 15.
Figure 16B:
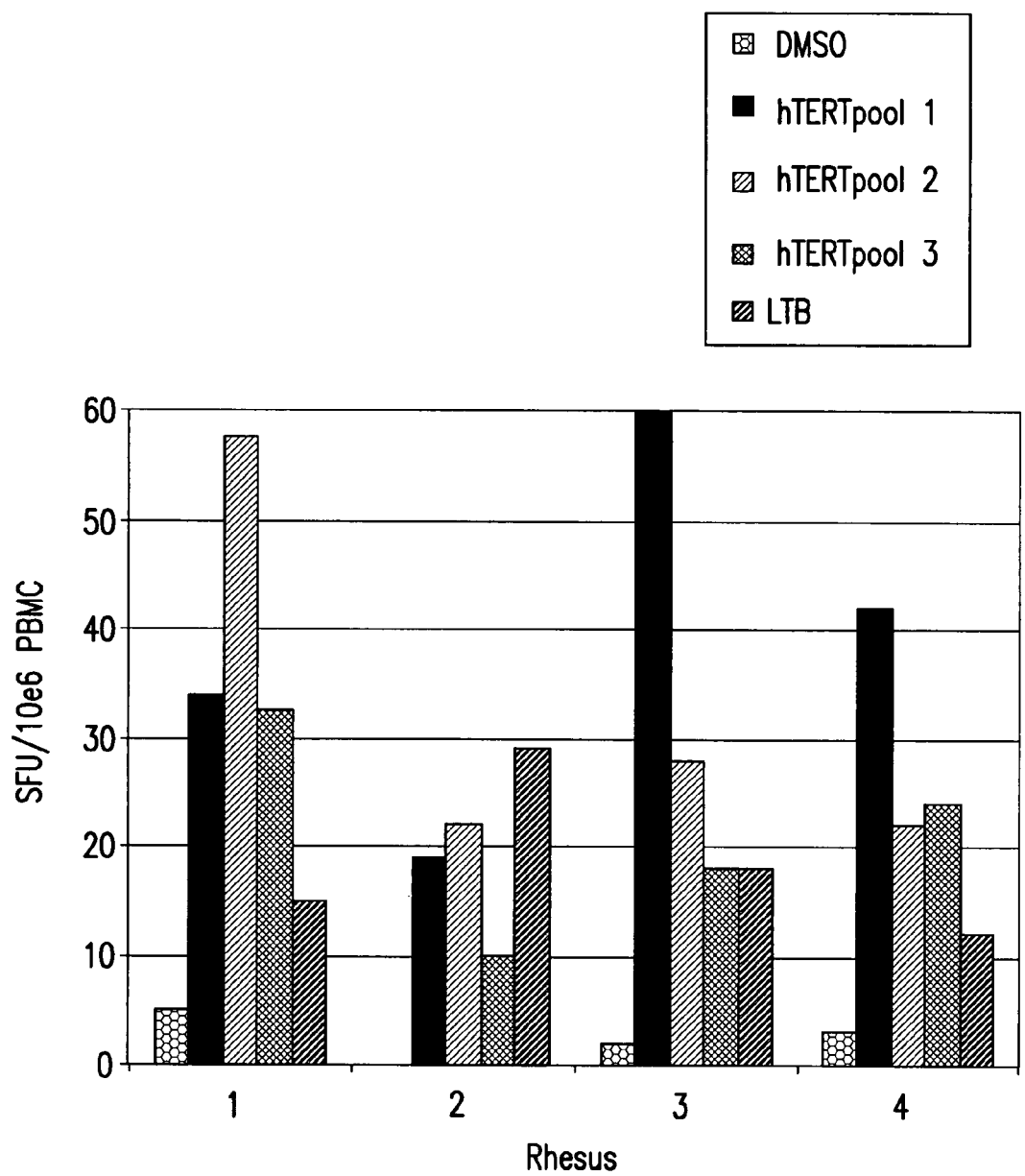
Figure 17:
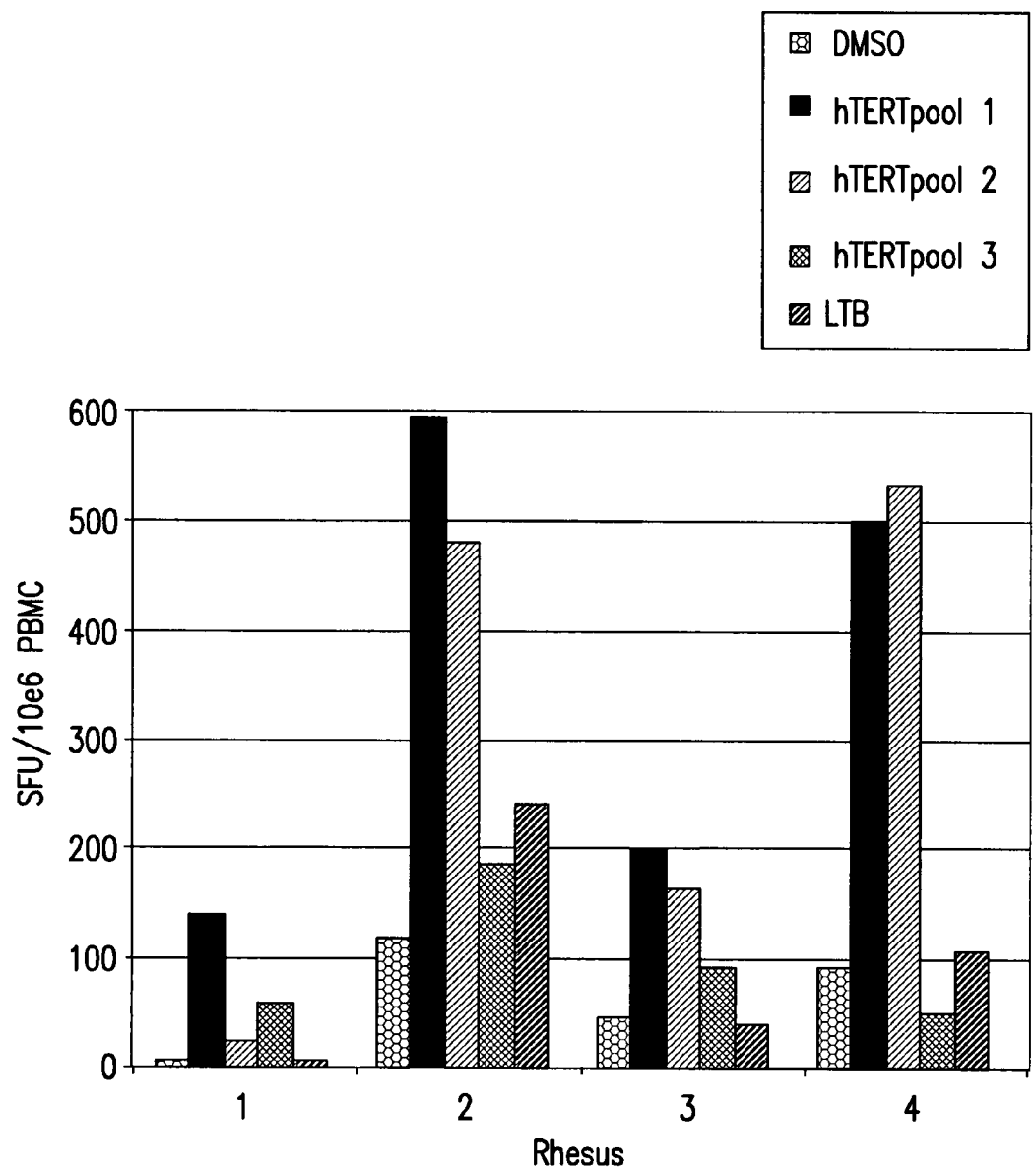
FIG. 17 shows that the cell-mediated immune response to hTERT was amplified in rhesus monkeys that were vaccinated with DNA-EP and boosted with adenovirus expressing hTERT, compared to the CMI elicited in monkeys vaccinated by DNA-EP alone. ELIspot was performed on PBMC from hTERT-immunized rhesus monkeys at the end of the immunization program, which included five DNA-EP (pV1J/TPA-hTERT(AI)-LTB) injections followed by two Ad (Ad6-hTERT(AI)) injections. The assay was performed in duplicate and the average value from the replicates is shown. See EXAMPLE 15.

ELIspot analysis of the induced CMI indicated that there was a detectable immune response after the first 2 DNA-EP treatments in four out of four vaccinated monkeys (FIG. 16A). A slight increase of the response was observed after the fifth DNA-EP (FIG. 16B). The immune response was also measured at the end of the complete immunization protocol, after the two Ad boosts. Results indicate that the Ad boosts induced a consistent increase in the amplitude of CMI (FIG. 17). Therefore, the power of a heterologous prime/boost modality was further confirmed by this experiment.

What is claimed is:

1. An isolated nucleic acid molecule comprising a sequence of nucleotides that encodes a human telomerase reverse transcriptase (hTERT) fusion protein, wherein the hTERT fusion protein comprises a hTERT protein fused to an Escherichia coli heat-labile enterotoxin B-subunit (LTB) peptide, wherein the sequence of nucleotides comprises the sequence of SEQ ID NO:5 or SEQ ID NO:1, and wherein the fusion protein is capable of producing an immune response.

2. A recombinant vector comprising the nucleic acid molecule of claim 1.

3. The recombinant vector of claim 2, wherein the vector is a plasmid vector or an adenovirus vector.

4. A host cell comprising the recombinant vector of claim 3.

5. The vector of claim 3, wherein the recombinant vector is an adenoviral vector that is selected from the group consisting of: an adenovirus type 5 (Ad5)vector, and an adenovirus type 5 (Ad6) vector.

* * * * *

SEQUENCE LISTING

<160> NUMBER OF SEQ ID NOS: 23

<210> SEQ ID NO 1
<211> LENGTH: 3783
<212> TYPE: DNA
<213> ORGANISM: Artificial Sequence
<220> FEATURE:
<223> OTHER INFORMATION: TPA-hTERT(AI)-LTBopt

<400> SEQUENCE: 1

| | | | | | |
|---|---|---|---|---|---|
| atggatgcaa | tgaagagggg | cctgtgctgc | gtgctgctgc | tgtgtggcgc | cgtgtttgtg | 60 |
| agccctagcg | agatccccag | agcccccaga | tgcagagccg | tgcggagcct | gctgcggagc | 120 |
| cactaccggg | aagtgctgcc | cctggccacc | ttcgtgcggc | ggctgggccc | cagggctgg | 180 |
| cggctggtgc | agcggggcga | ccctgccgcc | ttccgggccc | tggtggctca | gtgcctggtg | 240 |
| tgcgtgccct | gggacgccag | accccccca | gccgcccta | gcttccggca | ggtgagctgc | 300 |
| ctgaaggaac | tggtggccag | agtgctgcag | cggctgtgcg | agagaggcgc | caagaacgtg | 360 |
| ctggccttcg | gcttcgccct | gctggacggc | gccagaggcg | ccctcccga | ggccttcacc | 420 |
| acaagcgtgc | ggagctacct | gcccaacacc | gtgaccgacg | ccctgcgggg | cagcggcgcc | 480 |
| tggggcctgc | tgctgagaag | agtgggcgac | gacgtgctgg | tgcacctgct | ggcccggtgc | 540 |
| gccctgttcg | tgctggtggc | cccagctgc | gcctaccagg | tgtgcggccc | acccctgtac | 600 |
| cagctgggag | ccgccaccca | ggccaggccc | cacccacg | ccagcggccc | cagacggaga | 660 |
| ctgggctgcg | agcgggcctg | gaaccacagc | gtgagagagg | ccggcgtgcc | cctgggcctg | 720 |
| ccagcccctg | cgccagaag | aagaggcggc | agcgccagcc | ggagcctgcc | cctgcccaag | 780 |
| cggcccagaa | gaggcgctgc | ccccgagccc | gagcggaccc | ccgtgggcca | gggcagctgg | 840 |
| gcccaccccg | gcagaaccag | aggccccagc | gaccggggct | tctgcgtggt | gagccccgcc | 900 |
| agacccgccg | aggaggccac | aagcctggag | ggcgccctga | cggcacccg | gcacagccac | 960 |
| cccagcgtgg | gccggcagca | ccacgccgga | ccccccagca | ccagcagacc | cccagaccc | 1020 |
| tgggacaccc | cctgccccc | tgtgtacgcc | gagaccaagc | acttcctgta | cagcagcggc | 1080 |
| gacaaggagc | agctgcggcc | cagcttcctg | ctgagcagcc | tgagacccag | cctgaccggc | 1140 |
| gccaggagac | tggtggagac | catcttcctg | ggcagccggc | cctggatgcc | cggcaccccc | 1200 |
| cggagactgc | cccggctgcc | ccagcggtac | tggcagatgc | ggcccctgtt | cctggagctg | 1260 |
| ctgggcaacc | acgcccagtg | ccctacggc | gtgctgctga | aaacccactg | cccctgaga | 1320 |
| gccgccgtga | ccccgctgc | cggcgtgtgc | gccagagaga | agccccaggg | cagcgtggcc | 1380 |
| gctcccgagg | aggaggacac | cgaccccaga | cgcctggtgc | agctgctgcg | gcagcacagc | 1440 |
| agcccttggc | aggtgtacgg | cttcgtgcgg | gcctgcctga | aaggctggt | gccccctggc | 1500 |
| ctgtggggca | gcagacacaa | cgagcggcgg | ttcctgcgga | acaccaagaa | gttcatcagc | 1560 |
| ctggggaagc | acgccaagct | gagcctgcag | gaactgacct | ggaagatgag | cgtgcgggac | 1620 |
| tgcgcctggc | tgcggcggag | ccctggccgtg | gctgcgtgc | cagccgccga | gcaccggctg | 1680 |
| cgggaggaga | tcctggccaa | gttcctgcac | tggctgatga | gcgtgtacgt | ggtggaactg | 1740 |
| ctgcggtcct | tcttctacgt | gaccgaaacc | accttccaga | gaaccggct | gttcttctac | 1800 |
| cggaagagcg | tgtggagcaa | gctgcagagc | atcggcatca | ggcagcacct | gaagagagtg | 1860 |
| cagctgcggg | agctgagcga | ggccgaagtg | agacagcacc | gggaggccag | acctgccctg | 1920 |
| ctgaccagcc | ggctgcggtt | catccccaag | cccgacggcc | tgcggcccat | cgtgaacatg | 1980 |

```
gactacgtgg tgggcgccag aaccttccgg cgggagaagc gggccgagcg gctgaccagc    2040
agagtgaagg ccctgttcag cgtgctgaac tacgagcggg ccaggagacc cggcctgctg    2100
ggcgccagcg tgctgggcct ggacgacatc accgggcct ggcggacctt cgtgctgaga     2160
gtgcgggccc aggaccccc acccgagctg tacttcgtga agtggccat caccggcgcc      2220 tacgacacca tccccagga ccggctgacc gaagtgatcg ccagcatcat caagccccag     2280
aacacctact gcgtgcggcg gtacgccgtg gtgcagaagg ccgcccacgg ccacgtgcgg    2340
aaggccttca gagccacgt gagcaccctg accgacctgc agccctacat gcggcagttc    2400
gtggcccacc tgcaggagac cagccccctg cgggatgccg tggtgatcga gcagagcagc    2460
agcctgaacg aggccagcag cggcctgttc gacgtgttcc tgcgcttcat gtgccaccac   2520
gccgtgcgga tccggggcaa gagctacgtg cagtgccagg gcatccctca gggcagcatc    2580
ctgagcacac tgctgtgctc tctgtgctac ggcgacatgg agaacaagct gttcgccggc    2640
atccggcggg acggactgct gctgcgcctg gtggacgact cctgctggt gacccctcac     2700 ctgacccacg ccaagacctt cctgcggacc ctggtgcggg cgtgcccga gtacggctgt    2760 gtggtgaacc tgcgcaagac cgtggtgaac ttccccgtgg aggacgaggc cctgggcggc   2820
acagccttcg tgcagatgcc cgcccatggc ctgttccctt ggtgcgggct gctgctggac   2880
acccggaccc tggaagtgca gagcgactac agcagctacg cccggaccag catccgggcc   2940
agcctgacat tcaaccgcgg cttcaaggcc ggcagaaaca tgcggcggaa gctgtttggc   3000
gtgctgcggc tgaagtgcca cagcctgttt ctggacctgc aggtgaacag cctgcagacc   3060
gtgtgcacca acatctacaa gatcctgctg ctgcaggcct accggttcca cgcctgcgtg    3120
ctgcagctgc ccttccatca gcaggtgtgg aagaacccca ccttcttcct gcgcgtgatc    3180
tctgacaccg ccagcctgtg ctacagcatt ctgaaggcca gaacgccgg catgagcctg     3240 ggcgccaagg cgctgccgg acccctgccc agcgaggccg tgcagtggct gtgtcaccag    3300 gccttttctgc tgaagctgac ccggcaccgc gtgacctacg tgcccctgct gggaagcctg   3360
cggaccgccc agacccagct gagccggaag ctgcctggca ccaccctgac agccctggag   3420
gccgctgcca ccccgccct gcctagcgac ttcaagacca tcctggactc tagagccct    3480 cagagcatca ccgagctgtg cagcgagtac cggaacaccc agatttacac catcaacgac   3540
aagatcctga gctacaccga gtctatggcc ggcaagcggg agatggtgat catcaccttc   3600
aagagcggcg ccacctttca ggtggaagtg cctggcagcc agcacatcga cagccagaag   3660
aaggccatcg agcggatgaa ggacaccctg cggatcacct acctgaccga gaccaagatc   3720
gacaagctgt gtgtgtggaa caacaagacc cccaacagca tcgccgccat ctctatggag   3780
aac                                                                3783
```

<210> SEQ ID NO 2
<211> LENGTH: 1267
<212> TYPE: PRT
<213> ORGANISM: Artificial Sequence
<220> FEATURE:
<223> OTHER INFORMATION: -hTERT(AI)-LTBopt

<400> SEQUENCE: 2

Met Asp Ala Met Lys Arg Gly Leu Cys Cys Val Leu Leu Cys Gly
 1               5                  10                  15

Ala Val Phe Val Ser Pro Ser Glu Ile Pro Arg Ala Pro Arg Cys Arg
                20                  25                  30

Ala Val Arg Ser Leu Leu Arg Ser His Tyr Arg Glu Val Leu Pro Leu
            35                  40                  45

```
Ala Thr Phe Val Arg Arg Leu Gly Pro Gln Gly Trp Arg Leu Val Gln
        50                  55                  60

Arg Gly Asp Pro Ala Ala Phe Arg Ala Leu Val Ala Gln Cys Leu Val
 65                  70                  75                  80

Cys Val Pro Trp Asp Ala Arg Pro Pro Ala Pro Ser Phe Arg
                    85                  90                  95

Gln Val Ser Cys Leu Lys Glu Leu Val Ala Arg Val Leu Gln Arg Leu
            100                 105                 110

Cys Glu Arg Gly Ala Lys Asn Val Leu Ala Phe Gly Phe Ala Leu Leu
                115                 120                 125

Asp Gly Ala Arg Gly Gly Pro Pro Glu Ala Phe Thr Thr Ser Val Arg
        130                 135                 140

Ser Tyr Leu Pro Asn Thr Val Thr Asp Ala Leu Arg Gly Ser Gly Ala
145                 150                 155                 160

Trp Gly Leu Leu Leu Arg Arg Val Gly Asp Asp Val Leu Val His Leu
                165                 170                 175

Leu Ala Arg Cys Ala Leu Phe Val Leu Val Ala Pro Ser Cys Ala Tyr
                180                 185                 190

Gln Val Cys Gly Pro Pro Leu Tyr Gln Leu Gly Ala Ala Thr Gln Ala
            195                 200                 205

Arg Pro Pro Pro His Ala Ser Gly Pro Arg Arg Leu Gly Cys Glu
210                 215                 220

Arg Ala Trp Asn His Ser Val Arg Glu Ala Gly Val Pro Leu Gly Leu
225                 230                 235                 240

Pro Ala Pro Gly Ala Arg Arg Arg Gly Ser Ala Ser Arg Ser Leu
                245                 250                 255

Pro Leu Pro Lys Arg Pro Arg Arg Gly Ala Ala Pro Glu Pro Glu Arg
                260                 265                 270

Thr Pro Val Gly Gln Gly Ser Trp Ala His Pro Gly Arg Thr Arg Gly
            275                 280                 285

Pro Ser Asp Arg Gly Phe Cys Val Val Ser Pro Ala Arg Pro Ala Glu
        290                 295                 300

Glu Ala Thr Ser Leu Glu Gly Ala Leu Ser Gly Thr Arg His Ser His
305                 310                 315                 320

Pro Ser Val Gly Arg Gln His His Ala Gly Pro Pro Ser Thr Ser Arg
            325                 330                 335

Pro Pro Arg Pro Trp Asp Thr Pro Cys Pro Val Tyr Ala Glu Thr
                340                 345                 350

Lys His Phe Leu Tyr Ser Ser Gly Asp Lys Glu Gln Leu Arg Pro Ser
        355                 360                 365

Phe Leu Leu Ser Ser Leu Arg Pro Ser Leu Thr Gly Ala Arg Arg Leu
370                 375                 380

Val Glu Thr Ile Phe Leu Gly Ser Arg Pro Trp Met Pro Gly Thr Pro
385                 390                 395                 400

Arg Arg Leu Pro Arg Leu Pro Gln Arg Tyr Trp Gln Met Arg Pro Leu
                405                 410                 415

Phe Leu Glu Leu Leu Gly Asn His Ala Gln Cys Pro Tyr Gly Val Leu
                420                 425                 430

Leu Lys Thr His Cys Pro Leu Arg Ala Ala Val Thr Pro Ala Ala Gly
                435                 440                 445

Val Cys Ala Arg Glu Lys Pro Gln Gly Ser Val Ala Ala Pro Glu Glu
450                 455                 460

Glu Asp Thr Asp Pro Arg Arg Leu Val Gln Leu Leu Arg Gln His Ser
```

-continued

```
            465                 470                 475                 480
        Ser Pro Trp Gln Val Tyr Gly Phe Val Arg Ala Cys Leu Arg Arg Leu
                        485                 490                 495

Val Pro Pro Gly Leu Trp Gly Ser Arg His Asn Glu Arg Arg Phe Leu
                        500                 505                 510

Arg Asn Thr Lys Lys Phe Ile Ser Leu Gly Lys His Ala Lys Leu Ser
                        515                 520                 525

Leu Gln Glu Leu Thr Trp Lys Met Ser Val Arg Asp Cys Ala Trp Leu
                        530                 535                 540

Arg Arg Ser Pro Gly Val Gly Cys Val Pro Ala Ala Glu His Arg Leu
        545                 550                 555                 560

Arg Glu Glu Ile Leu Ala Lys Phe Leu His Trp Leu Met Ser Val Tyr
                        565                 570                 575

Val Val Glu Leu Leu Arg Ser Phe Phe Tyr Val Thr Glu Thr Thr Phe
                        580                 585                 590

Gln Lys Asn Arg Leu Phe Phe Tyr Arg Lys Ser Val Trp Ser Lys Leu
                        595                 600                 605

Gln Ser Ile Gly Ile Arg Gln His Leu Lys Arg Val Gln Leu Arg Glu
                        610                 615                 620

Leu Ser Glu Ala Glu Val Arg Gln His Arg Glu Ala Arg Pro Ala Leu
        625                 630                 635                 640

Leu Thr Ser Arg Leu Arg Phe Ile Pro Lys Pro Asp Gly Leu Arg Pro
                        645                 650                 655

Ile Val Asn Met Asp Tyr Val Val Gly Ala Arg Thr Phe Arg Arg Glu
                        660                 665                 670

Lys Arg Ala Glu Arg Leu Thr Ser Arg Val Lys Ala Leu Phe Ser Val
                        675                 680                 685

Leu Asn Tyr Glu Arg Ala Arg Arg Pro Gly Leu Leu Gly Ala Ser Val
                        690                 695                 700

Leu Gly Leu Asp Asp Ile His Arg Ala Trp Arg Thr Phe Val Leu Arg
        705                 710                 715                 720

Val Arg Ala Gln Asp Pro Pro Glu Leu Tyr Phe Val Lys Val Ala
                        725                 730                 735

Ile Thr Gly Ala Tyr Asp Thr Ile Pro Gln Asp Arg Leu Thr Glu Val
                        740                 745                 750

Ile Ala Ser Ile Ile Lys Pro Gln Asn Thr Tyr Cys Val Arg Arg Tyr
                        755                 760                 765

Ala Val Val Gln Lys Ala Ala His Gly His Val Arg Lys Ala Phe Lys
                        770                 775                 780

Ser His Val Ser Thr Leu Thr Asp Leu Gln Pro Tyr Met Arg Gln Phe
        785                 790                 795                 800

Val Ala His Leu Gln Glu Thr Ser Pro Leu Arg Asp Ala Val Val Ile
                        805                 810                 815

Glu Gln Ser Ser Ser Leu Asn Glu Ala Ser Ser Gly Leu Phe Asp Val
                        820                 825                 830

Phe Leu Arg Phe Met Cys His His Ala Val Arg Ile Arg Gly Lys Ser
                        835                 840                 845

Tyr Val Gln Cys Gln Gly Ile Pro Gln Gly Ser Ile Leu Ser Thr Leu
                        850                 855                 860

Leu Cys Ser Leu Cys Tyr Gly Asp Met Glu Asn Lys Leu Phe Ala Gly
        865                 870                 875                 880

Ile Arg Arg Asp Gly Leu Leu Leu Arg Leu Val Asp Asp Phe Leu Leu
                        885                 890                 895
```

```
Val Thr Pro His Leu Thr His Ala Lys Thr Phe Leu Arg Thr Leu Val
            900                 905                 910

Arg Gly Val Pro Glu Tyr Gly Cys Val Val Asn Leu Arg Lys Thr Val
            915                 920                 925

Val Asn Phe Pro Val Glu Asp Glu Ala Leu Gly Gly Thr Ala Phe Val
            930                 935                 940

Gln Met Pro Ala His Gly Leu Phe Pro Trp Cys Gly Leu Leu Leu Asp
945                 950                 955                 960

Thr Arg Thr Leu Glu Val Gln Ser Asp Tyr Ser Ser Tyr Ala Arg Thr
                965                 970                 975

Ser Ile Arg Ala Ser Leu Thr Phe Asn Arg Gly Phe Lys Ala Gly Arg
            980                 985                 990

Asn Met Arg Arg Lys Leu Phe Gly Val Leu Arg Leu Lys Cys His Ser
            995                 1000                1005

Leu Phe Leu Asp Leu Gln Val Asn Ser Leu Gln Thr Val Cys Thr Asn
            1010                1015                1020

Ile Tyr Lys Ile Leu Leu Leu Gln Ala Tyr Arg Phe His Ala Cys Val
1025                1030                1035                1040

Leu Gln Leu Pro Phe His Gln Gln Val Trp Lys Asn Pro Thr Phe Phe
                1045                1050                1055

Leu Arg Val Ile Ser Asp Thr Ala Ser Leu Cys Tyr Ser Ile Leu Lys
            1060                1065                1070

Ala Lys Asn Ala Gly Met Ser Leu Gly Ala Lys Gly Ala Ala Gly Pro
            1075                1080                1085

Leu Pro Ser Glu Ala Val Gln Trp Leu Cys His Gln Ala Phe Leu Leu
            1090                1095                1100

Lys Leu Thr Arg His Arg Val Thr Tyr Val Pro Leu Leu Gly Ser Leu
1105                1110                1115                1120

Arg Thr Ala Gln Thr Gln Leu Ser Arg Lys Leu Pro Gly Thr Thr Leu
                1125                1130                1135

Thr Ala Leu Glu Ala Ala Ala Asn Pro Ala Leu Pro Ser Asp Phe Lys
            1140                1145                1150

Thr Ile Leu Asp Ser Arg Ala Pro Gln Ser Ile Thr Glu Leu Cys Ser
            1155                1160                1165

Glu Tyr Arg Asn Thr Gln Ile Tyr Thr Ile Asn Asp Lys Ile Leu Ser
1170                1175                1180

Tyr Thr Glu Ser Met Ala Gly Lys Arg Glu Met Val Ile Ile Thr Phe
1185                1190                1195                1200

Lys Ser Gly Ala Thr Phe Gln Val Glu Val Pro Gly Ser Gln His Ile
                1205                1210                1215

Asp Ser Gln Lys Lys Ala Ile Glu Arg Met Lys Asp Thr Leu Arg Ile
            1220                1225                1230

Thr Tyr Leu Thr Glu Thr Lys Ile Asp Lys Leu Cys Val Trp Asn Asn
            1235                1240                1245

Lys Thr Pro Asn Ser Ile Ala Ala Ile Ser Met Glu Asn Ser Glu Gln
            1250                1255                1260

Ile Asp Asn
1265

<210> SEQ ID NO 3
<211> LENGTH: 3753
<212> TYPE: DNA
<213> ORGANISM: Artificial Sequence
<220> FEATURE:
<223> OTHER INFORMATION: TPA-mTERT(AI)-LTBopt
```

-continued

```
<400> SEQUENCE: 3
atggatgcaa tgaagagggg cctgtgctgc gtgctgctgc tgtgtggcgc cgtgtttgtg      60
agccctagcg agatcaccag agcccccaga tgccctgccg tgagaagcct gctgcggagc     120
cggtacagag aagtgtggcc cctggccacc tttgtgagga gactgggccc tgagggcagg     180
agactggtgc agcctggcga ccccaaaatc tacaggaccc tggtggccca gtgtctggtg     240
tgtatgcact ggggcagcca gccccctccc gccgacctga gcttccacca ggtgtccagc     300
ctgaaggaac tggtggccag agtggtgcag agactgtgcg agcggaacga gagaaacgtg     360
ctggccttcg gcttcgagct gctgaacgag gccagaggcg ccctcccat ggccttcacc      420 agctctgtga ggagctacct gcccaacacc gtgatcgaga ccctgagagt gagcggcgcc     480
tggatgctgc tgctgagcag agtgggcgat gacctgctgg tgtacctgct ggcccactgc     540
gccctgtatc tgctggtgcc ccccagctgc gcctaccagg tgtgcggatc cccctgtac     600 cagatttgcg ccaccaccga catctggccc agcgtgtctg ccagctacag acccaccaga     660
cctgtgggcc ggaacttcac caacctgcgg ttcctgcagc agatcaagag cagcagcaga     720
caggaggccc ccaagcccct ggccctgccc agcagaggca ccaagagaca cctgagcctg     780
accagcacca gcgtgcccag cgccaagaaa gccagatgct accccgtgcc tagagtggag     840
gagggccctc acagacaggt gctgccacca ccagcggca agagctgggt gcccagcccc      900
gccagaagcc ccgaagtgcc caccgccgag aaggacctga gcagcaaggg caaagtgagc     960
gacctgtctc tgagcggcag cgtgtgttgc aagcacaagc ccagcagcac cagcctgctg    1020
agccccccca gacagaacgc cttccagctg aggcctttca tcgagacccg cgacttcctg    1080
tacagcagag cgatggcca ggagagactg aaccccagct cctgctgag caacctgcag      1140 cctaacctga ccggcgccag acgctggtg gagatcatct tcctgggcag cagacccaga     1200
accagcggcc ctctgtgcag aacccaccgg ctgagcaggc ggtactggca gatgagaccc    1260
ctgttccagc agctgctggt gaaccacgcc gagtgccagt atgtgcggct gctgaggagc    1320
cactgcagat tcaggaccgc caaccagcag gtgaccgacg ccctgaacac cagcccccct    1380
cacctgatgg atctgctgag gctgcacagc agccctggc aggtgtacgg cttcctgaga     1440
gcctgcctgt gcaaagtggt gtccgccagc ctgtggggca ccagacacaa cgagcggcgg    1500
ttcttcaaga atctgaagaa gttcatcagc ctgggcaagt acggcaagct gagcctgcag    1560
gaactgatgt ggaagatgaa agtggaggac tgccactggc tgagaagcag ccccggcaag    1620
gacagagtgc ctgccgccga gcacagactg agggagagaa tcctggccac attcctgttc    1680
tggctgatgg acacctacgt ggtgcagctg ctgcggtcct tcttctacat caccgagagc    1740
accttccaga gaaccggct gttcttctac cggaagtctg tgtggagcaa gctgcagagc    1800
atcggagtga cagcacct ggagagagtg aggctgagag agctgagcca ggaggaagtg      1860
agacaccacc aggatacctg gctggccatg cccatctgcc ggctgagatt catccccaag    1920
cccaacggcc tgagacccat cgtgaacatg agctacagca tgggcacaag agccctgggc    1980
agaagaaagc aggcccagca cttcacccag cggctgaaaa ccctgttctc catgctgaac    2040
tacgagcgga ccaagcaccc acacctgatg gcagcagcg tgctgggcat gaacgacatc     2100
taccggacct ggagagcctt cgtgctgaga gtgcgggccc tggaccagac ccctcggatg    2160
tacttcgtga aggccgccat caccggcgcc tacgacgcca tccccaggg caaactggtg     2220 gaagtggtgg ccaacatgat caggcacagc gagtccacct actgcatcag gcagtacgcc    2280
gtggtgagaa gagacagcca gggccaggtg cacaagagct ccggagaca ggtgaccacc     2340
```

```
ctgagcgatc tgcagcctta catgggccag ttcctgaagc acctgcagga tagcgacgcc    2400
agcgccctga gaaatagcgt ggtgatcgag cagagcatca gcatgaacga gtccagcagc    2460
agcctgttcg acttcttcct gcacttcctg aggcacagcg tggtgaagat cggcgacaga    2520
tgctacaccc agtgtcaggg catccctcag ggctctagcc tgagcaccct gctgtgtagc    2580
ctgtgcttcg gcgacatgga gaataagctg ttcgccgaag tgcagagaga tggcctgctg    2640
ctgcgcttcg tggacgattt cctgctggtg accccacacc tggaccaggc caagaccttc    2700
ctgagcacac tggtgcacgg cgtgcccgag tacggctgca tgatcaatct gcagaaaacc    2760
gtggtgaact ccctgtgtga gcccggcacc ctgggcggag ccgcccctta ccagctgccc    2820
gcccactgcc tgttccctg gtgcggactg ctgctggata cccagaccct ggaagtgttc    2880
tgcgactaca cggctacgc ccagaccagc atcaagacca gcctgacctt ccagagcgtg    2940
ttcaaggccg gcaagaccat gaggaacaag ctgctgagcg tgctgagact gaagtgccac    3000
ggcctgttcc tggatctgca ggtgaacagc ctgcagaccg tgtgtatcaa catctacaag    3060
attttcctgc tgcaggccta cagattccac gcctgcgtga tccagctgcc cttcgaccag    3120
agagtgcgga gaaacctgac cttcttcctg gggatcatca gcagccaggc cagctgctgc    3180
tacgccatcc tgaaagtgaa gaaccccggc atgaccctga aggccagcgg cagcttccct    3240
cccgaggccg cccactggct gtgctaccag gcctttctgc tgaagctggc cgcccacagc    3300
gtgatctaca gtgcctgct gggccctctg agaaccgccc agaagctgct gtgccggaag    3360
ctgcccgagg ccaccatgac cattctgaaa gccgccgccg acccccgcct gagcaccgac    3420
ttccagacca tcctggactc tagagccccct cagagcatca ccgagctgtg cagcgagtac    3480
cggaacaccc agatttacac catcaacgac aagatcctga gctacaccga gtctatggcc    3540
ggcaagcggg agatggtgat catcaccttc aagagcggcg ccacctttca ggtggaagtg    3600
cctggcagcc agcacatcga cagcagaag aaggccatcg agcggatgaa ggacacctg    3660
cggatcaccct acctgaccga gaccaagatc gacaagctgt gtgtgtggaa caacaagacc    3720
cccaacagca tcgccgccat ctctatggag aac                                 3753
```

<210> SEQ ID NO 4
<211> LENGTH: 1251
<212> TYPE: PRT
<213> ORGANISM: Artificial Sequence
<220> FEATURE:
<223> OTHER INFORMATION: TPA-mTERT(AI)-LTBopt

<400> SEQUENCE: 4

```
Met Asp Ala Met Lys Arg Gly Leu Cys Cys Val Leu Leu Cys Gly
  1               5                  10                  15

Ala Val Phe Val Ser Pro Ser Glu Ile Thr Arg Ala Pro Arg Cys Pro
                 20                  25                  30

Ala Val Arg Ser Leu Leu Arg Ser Arg Tyr Arg Glu Val Trp Pro Leu
             35                  40                  45

Ala Thr Phe Val Arg Arg Leu Gly Pro Glu Gly Arg Leu Val Gln
         50                  55                  60

Pro Gly Asp Pro Lys Ile Tyr Arg Thr Leu Val Ala Gln Cys Leu Val
 65                  70                  75                  80

Cys Met His Trp Gly Ser Gln Pro Pro Ala Asp Leu Ser Phe His
                 85                  90                  95

Gln Val Ser Ser Leu Lys Glu Leu Val Ala Arg Val Val Gln Arg Leu
            100                 105                 110

Cys Glu Arg Asn Glu Arg Asn Val Leu Ala Phe Gly Phe Glu Leu Leu
```

```
            115                 120                 125
Asn Glu Ala Arg Gly Gly Pro Pro Met Ala Phe Thr Ser Ser Val Arg
            130                 135                 140
Ser Tyr Leu Pro Asn Thr Val Ile Glu Thr Leu Arg Val Ser Gly Ala
145                 150                 155                 160
Trp Met Leu Leu Leu Ser Arg Val Gly Asp Asp Leu Leu Val Tyr Leu
                165                 170                 175
Leu Ala His Cys Ala Leu Tyr Leu Val Pro Pro Ser Cys Ala Tyr
                180                 185                 190
Gln Val Cys Gly Ser Pro Leu Tyr Gln Ile Cys Ala Thr Thr Asp Ile
                195                 200                 205
Trp Pro Ser Val Ser Ala Ser Tyr Arg Pro Thr Arg Pro Val Gly Arg
210                 215                 220
Asn Phe Thr Asn Leu Arg Phe Leu Gln Gln Ile Lys Ser Ser Ser Arg
225                 230                 235                 240
Gln Glu Ala Pro Lys Pro Leu Ala Leu Pro Ser Arg Gly Thr Lys Arg
                245                 250                 255
His Leu Ser Leu Thr Ser Thr Ser Val Pro Ser Ala Lys Lys Ala Arg
                260                 265                 270
Cys Tyr Pro Val Pro Arg Val Glu Glu Gly Pro His Arg Gln Val Leu
                275                 280                 285
Pro Thr Pro Ser Gly Lys Ser Trp Val Pro Ser Pro Ala Arg Ser Pro
290                 295                 300
Glu Val Pro Thr Ala Glu Lys Asp Leu Ser Ser Lys Gly Lys Val Ser
305                 310                 315                 320
Asp Leu Ser Leu Ser Gly Ser Val Cys Cys Lys His Lys Pro Ser Ser
                325                 330                 335
Thr Ser Leu Leu Ser Pro Pro Arg Gln Asn Ala Phe Gln Leu Arg Pro
                340                 345                 350
Phe Ile Glu Thr Arg His Phe Leu Tyr Ser Arg Gly Asp Gly Gln Glu
                355                 360                 365
Arg Leu Asn Pro Ser Phe Leu Leu Ser Asn Leu Gln Pro Asn Leu Thr
370                 375                 380
Gly Ala Arg Arg Leu Val Glu Ile Ile Phe Leu Gly Ser Arg Pro Arg
385                 390                 395                 400
Thr Ser Gly Pro Leu Cys Arg Thr His Arg Leu Ser Arg Arg Tyr Trp
                405                 410                 415
Gln Met Arg Pro Leu Phe Gln Gln Leu Leu Val Asn His Ala Glu Cys
                420                 425                 430
Gln Tyr Val Arg Leu Leu Arg Ser His Cys Arg Phe Arg Thr Ala Asn
                435                 440                 445
Gln Gln Val Thr Asp Ala Leu Asn Thr Ser Pro Pro His Leu Met Asp
                450                 455                 460
Leu Leu Arg Leu His Ser Ser Pro Trp Gln Val Tyr Gly Phe Leu Arg
465                 470                 475                 480
Ala Cys Leu Cys Lys Val Val Ser Ala Ser Leu Trp Gly Thr Arg His
                485                 490                 495
Asn Glu Arg Arg Phe Phe Lys Asn Leu Lys Lys Phe Ile Ser Leu Gly
                500                 505                 510
Lys Tyr Gly Lys Leu Ser Leu Gln Glu Leu Met Trp Lys Met Lys Val
                515                 520                 525
Glu Asp Cys His Trp Leu Arg Ser Ser Pro Gly Lys Asp Arg Val Pro
530                 535                 540
```

-continued

```
Ala Ala Glu His Arg Leu Arg Glu Arg Ile Leu Ala Thr Phe Leu Phe
545                 550                 555                 560

Trp Leu Met Asp Thr Tyr Val Val Gln Leu Leu Arg Ser Phe Phe Tyr
            565                 570                 575

Ile Thr Glu Ser Thr Phe Gln Lys Asn Arg Leu Phe Phe Tyr Arg Lys
            580                 585                 590

Ser Val Trp Ser Lys Leu Gln Ser Ile Gly Val Arg Gln His Leu Glu
        595                 600                 605

Arg Val Arg Leu Arg Glu Leu Ser Gln Glu Glu Val Arg His His Gln
610                 615                 620

Asp Thr Trp Leu Ala Met Pro Ile Cys Arg Leu Arg Phe Ile Pro Lys
625                 630                 635                 640

Pro Asn Gly Leu Arg Pro Ile Val Asn Met Ser Tyr Ser Met Gly Thr
                645                 650                 655

Arg Ala Leu Gly Arg Arg Lys Gln Ala Gln His Phe Thr Gln Arg Leu
            660                 665                 670

Lys Thr Leu Phe Ser Met Leu Asn Tyr Glu Arg Thr Lys His Pro His
        675                 680                 685

Leu Met Gly Ser Ser Val Leu Gly Met Asn Asp Ile Tyr Arg Thr Trp
690                 695                 700

Arg Ala Phe Val Leu Arg Val Arg Ala Leu Asp Gln Thr Pro Arg Met
705                 710                 715                 720

Tyr Phe Val Lys Ala Ala Ile Thr Gly Ala Tyr Asp Ala Ile Pro Gln
                725                 730                 735

Gly Lys Leu Val Glu Val Val Ala Asn Met Ile Arg His Ser Glu Ser
            740                 745                 750

Thr Tyr Cys Ile Arg Gln Tyr Ala Val Val Arg Arg Asp Ser Gln Gly
        755                 760                 765

Gln Val His Lys Ser Phe Arg Arg Gln Val Thr Thr Leu Ser Asp Leu
770                 775                 780

Gln Pro Tyr Met Gly Gln Phe Leu Lys His Leu Gln Asp Ser Asp Ala
785                 790                 795                 800

Ser Ala Leu Arg Asn Ser Val Val Ile Glu Gln Ser Ile Ser Met Asn
                805                 810                 815

Glu Ser Ser Ser Ser Leu Phe Asp Phe Phe Leu His Phe Leu Arg His
            820                 825                 830

Ser Val Val Lys Ile Gly Asp Arg Cys Tyr Thr Gln Cys Gln Gly Ile
        835                 840                 845

Pro Gln Gly Ser Ser Leu Ser Thr Leu Leu Cys Ser Leu Cys Phe Gly
850                 855                 860

Asp Met Glu Asn Lys Leu Phe Ala Glu Val Gln Arg Asp Gly Leu Leu
865                 870                 875                 880

Leu Arg Phe Val Asp Asp Phe Leu Leu Val Thr Pro His Leu Asp Gln
                885                 890                 895

Ala Lys Thr Phe Leu Ser Thr Leu Val His Gly Val Pro Glu Tyr Gly
            900                 905                 910

Cys Met Ile Asn Leu Gln Lys Thr Val Val Asn Phe Pro Val Glu Pro
        915                 920                 925

Gly Thr Leu Gly Gly Ala Ala Pro Tyr Gln Leu Pro Ala His Cys Leu
930                 935                 940

Phe Pro Trp Cys Gly Leu Leu Leu Asp Thr Gln Thr Leu Glu Val Phe
945                 950                 955                 960

Cys Asp Tyr Ser Gly Tyr Ala Gln Thr Ser Ile Lys Thr Ser Leu Thr
                965                 970                 975
```

Phe Gln Ser Val Phe Lys Ala Gly Lys Thr Met Arg Asn Lys Leu Leu
            980                 985                 990

Ser Val Leu Arg Leu Lys Cys His Gly Leu Phe Leu Asp Leu Gln Val
        995                 1000                1005

Asn Ser Leu Gln Thr Val Cys Ile Asn Ile Tyr Lys Ile Phe Leu Leu
    1010                1015                1020

Gln Ala Tyr Arg Phe His Ala Cys Val Ile Gln Leu Pro Phe Asp Gln
1025                1030                1035                1040

Arg Val Arg Lys Asn Leu Thr Phe Phe Leu Gly Ile Ile Ser Ser Gln
            1045                1050                1055

Ala Ser Cys Cys Tyr Ala Ile Leu Lys Val Lys Asn Pro Gly Met Thr
        1060                1065                1070

Leu Lys Ala Ser Gly Ser Phe Pro Pro Glu Ala Ala His Trp Leu Cys
    1075                1080                1085

Tyr Gln Ala Phe Leu Leu Lys Leu Ala Ala His Ser Val Ile Tyr Lys
1090                1095                1100

Cys Leu Leu Gly Pro Leu Arg Thr Ala Gln Lys Leu Leu Cys Arg Lys
1105                1110                1115                1120

Leu Pro Glu Ala Thr Met Thr Ile Leu Lys Ala Ala Asp Pro Ala
            1125                1130                1135

Leu Ser Thr Asp Phe Gln Thr Ile Leu Asp Ser Arg Ala Pro Gln Ser
        1140                1145                1150

Ile Thr Glu Leu Cys Ser Glu Tyr Arg Asn Thr Gln Ile Tyr Thr Ile
    1155                1160                1165

Asn Asp Lys Ile Leu Ser Tyr Thr Glu Ser Met Ala Gly Lys Arg Glu
1170                1175                1180

Met Val Ile Ile Thr Phe Lys Ser Gly Ala Thr Phe Gln Val Glu Val
1185                1190                1195                1200

Pro Gly Ser Gln His Ile Asp Ser Gln Lys Lys Ala Ile Glu Arg Met
            1205                1210                1215

Lys Asp Thr Leu Arg Ile Thr Tyr Leu Thr Glu Thr Lys Ile Asp Lys
        1220                1225                1230

Leu Cys Val Trp Asn Asn Lys Thr Pro Asn Ser Ile Ala Ala Ile Ser
    1235                1240                1245

Met Glu Asn
    1250

<210> SEQ ID NO 5
<211> LENGTH: 3711
<212> TYPE: DNA
<213> ORGANISM: Artificial Sequence
<220> FEATURE:
<223> OTHER INFORMATION: hTERT(AI)-LTBopt

<400> SEQUENCE: 5
cccagagccc ccagatgcag agccgtgcgg agcctgctgc ggagccacta ccgggaagtg      60 ctgccctgg ccaccttcgt gcggcggctg ggccccagg gctggcggct ggtgcagcgg       120
ggcgaccctg ccgccttccg ggccctggtg gctcagtgcc tggtgtgcgt gccctgggac      180
gccagacccc cccagccgc ccctagcttc cggcaggtga gctgcctgaa ggaactggtg       240
gccagagtgc tgcagcggct gtgcgagaga ggcgccaaga acgtgctggc cttcggcttc      300
gccctgctgg acggcgccag aggcggccct cccgaggcct tcaccacaag cgtgcggagc      360
tacctgccca acaccgtgac cgacgccctg cggggcagcg cgcctggggg cctgctgctg      420
agaagagtgg gcgacgacgt gctggtgcac ctgctggccc ggtgcgccct gttcgtgctg      480

```
gtggccccca gctgcgccta ccaggtgtgc ggcccacccc tgtaccagct gggagccgcc    540
acccaggcca ggcccccacc ccacgccagc ggccccagac ggagactggg ctgcgagcgg    600
gcctggaacc acagcgtgag agaggccggc gtgcccctgg gcctgccagc ccctggcgcc    660
agaagaagag gcggcagcgc cagccggagc ctgcccctgc ccaagcggcc agaagaggc    720 gctgcccccg agcccgagcg gaccccgtg ggcagggca gctgggccca ccccggcaga    780
accagaggcc ccagcgaccg ggcttctgc gtggtgagcc ccgccagacc cgccgaggag    840
gccacaagcc tggagggcgc cctgagcgg acccggcaca gccacccag cgtgggccgg    900 cagcaccacg ccggaccccc cagcaccagc agaccccca gaccctggga cacccctgc    960 ccccctgtgt acgccgagac caagcacttc ctgtacagca gcggcgacaa ggagcagctg   1020
cggcccagct tcctgctgag cagcctgaga cccagcctga ccgcgccag gagactggtg   1080 gagaccatct tcctgggcag ccggccctgg atgcccggca ccccccggag actgccccgg   1140
ctgccccagc ggtactggca gatgcggccc tgttcctgg agctgctggg caaccacgcc   1200
cagtgcccct acggcgtgct gctgaaaacc cactgccccc tgagagccgc cgtgaccccc   1260
gctgccggcg tgtgcgccag agagaagccc agggcagcg tggccgctcc cgaggaggag   1320
gacaccgacc ccagacgcct ggtgcagctg ctgcggcagc acagcagccc ttggcaggtg   1380
tacggcttcg tgcgggcctg cctgagaagg ctggtgcccc tggcctgtg ggcagcaga    1440 cacaacgagc ggcggttcct gcggaacacc aagaagttca tcagcctggg gaagcacgcc   1500
aagctgagcc tgcaggaact gacctggaag atgagcgtgc gggactgcgc ctggctgcgg   1560
cggagccctg gcgtgggctg cgtgccagcc gccgagcacc ggctgcggga ggagatcctg   1620
gccaagttcc tgcactggct gatgagcgtg tacgtggtgg aactgctgcg gtccttcttc   1680
tacgtgaccg aaaccacctt ccagaagaac cggctgttct ctaccggaa gagcgtgtgg   1740 agcaagctgc agagcatcgg catcaggcag cacctgaaga gagtgcagct gcgggagctg   1800
agcgaggccg aagtgagaca gcaccgggag gccagacctg ccctgctgac cagccggctg   1860
cggttcatcc ccaagcccga cggcctgcgg cccatcgtga acatggacta cgtggtgggc   1920
gccagaacct tccggcggga aagcgggcc gagcggctga ccagcagagt gaaggccctg   1980
ttcagcgtgc tgaactacga gcgggccagg agacccggcc tgctgggcgc cagcgtgctg   2040
ggcctggacg acatccaccg ggcctggcgg accttcgtgc tgagagtgcg ggcccaggac   2100
cccccacccg agctgtactt cgtgaaagtg gccataccg cgcctacga caccatcccc   2160 caggaccggc tgaccgaagt gatcgccagc atcatcaagc cccagaacac ctactgcgtg   2220
cggcggtacg ccgtggtgca aaggccgcc cacggccacg tgcggaaggc cttcaagagc   2280
cacgtgagca ccctgaccga cctgcagccc tacatgcggc agttcgtggc ccacctgcag   2340
gagaccagcc cctgcgggga tgccgtggtg atcgagcaga gcagcagcct gaacgaggcc   2400
agcagcggcc tgttcgacgt gttcctgcgc ttcatgtgcc accacgccgt gcggatccgg   2460
ggcaagagct acgtgcagtg ccagggcatc cctcagggca gcatcctgag cacactgctg   2520
tgctctctgt gctacggcga catggagaac aagctgttcg ccggcatccg gcgggacgga   2580
ctgctgctgc gcctggtgga cgacttcctg ctggtgaccc ctcacctgac ccacgccaag   2640
accttcctgc ggaccctggt gcggggcgtg cccgagtacg ctgtgtggt gaacctgcgc   2700 aagaccgtgg tgaacttccc cgtggaggac gaggccctgg cggcacagc cttcgtgcag   2760 atgcccgccc atggctgtt cccttggtgc gggctgctgc tggacacccg gaccctggaa   2820
gtgcagagcg actacagcag ctacgcccgg accagcatcc gggccagcct gacattcaac   2880
```

```
cgcggcttca aggccggcag aaacatgcgg cggaagctgt ttggcgtgct gcggctgaag    2940
tgccacagcc tgtttctgga cctgcaggtg aacagcctgc agaccgtgtg caccaacatc    3000
tacaagatcc tgctgctgca ggcctaccgg ttccacgcct gcgtgctgca gctgcccttc    3060
catcagcagg tgtggaagaa ccccaccttc ttcctgcgcg tgatctctga caccgccagc    3120
ctgtgctaca gcattctgaa ggccaagaac gccggcatga gcctgggcgc caagggcgct    3180
gccggacccc tgcccagcga ggccgtgcag tggctgtgtc accaggcctt tctgctgaag    3240
ctgacccggc accgcgtgac ctacgtgccc ctgctgggaa gcctgcggac cgcccagacc    3300
cagctgagcc ggaagctgcc tggcaccacc ctgacagccc tggaggccgc tgccaacccc    3360
gccctgccta cgacttcaa gaccatcctg gactctagag cccctcagag catcaccgag    3420
ctgtgcagcg agtaccggaa cacccagatt tacaccatca cgacaagat cctgagctac    3480 accgagtcta tggccggcaa gcggagatg gtgatcatca ccttcaagag cggcgccacc    3540
tttcaggtgg aagtgcctgg cagccagcac atcgacagcc agaagaaggc catcgagcgg    3600
atgaaggaca ccctgcggat cacctacctg accgagacca agatcgacaa gctgtgtgtg    3660
tggaacaaca gaccccccaa cagcatcgcc gccatctcta tggagaactg a             3711
```

<210> SEQ ID NO 6
<211> LENGTH: 1236
<212> TYPE: PRT
<213> ORGANISM: Artificial Sequence
<220> FEATURE:
<223> OTHER INFORMATION: hTERT(AI)-LTBopt

<400> SEQUENCE: 6

```
Pro Arg Ala Pro Arg Cys Arg Ala Val Arg Ser Leu Leu Arg Ser His
 1               5                  10                  15

Tyr Arg Glu Val Leu Pro Leu Ala Thr Phe Val Arg Arg Leu Gly Pro
                20                  25                  30

Gln Gly Trp Arg Leu Val Gln Arg Gly Asp Pro Ala Ala Phe Arg Ala
            35                  40                  45

Leu Val Ala Gln Cys Leu Val Cys Val Pro Trp Asp Ala Arg Pro Pro
        50                  55                  60

Pro Ala Ala Pro Ser Phe Arg Gln Val Ser Cys Leu Lys Glu Leu Val
 65                  70                  75                  80

Ala Arg Val Leu Gln Arg Leu Cys Glu Arg Gly Ala Lys Asn Val Leu
                85                  90                  95

Ala Phe Gly Phe Ala Leu Leu Asp Gly Ala Arg Gly Gly Pro Pro Glu
           100                 105                 110

Ala Phe Thr Thr Ser Val Arg Ser Tyr Leu Pro Asn Thr Val Thr Asp
       115                 120                 125

Ala Leu Arg Gly Ser Gly Ala Trp Gly Leu Leu Leu Arg Arg Val Gly
   130                 135                 140

Asp Asp Val Leu Val His Leu Leu Ala Arg Cys Ala Leu Phe Val Leu
145                 150                 155                 160

Val Ala Pro Ser Cys Ala Tyr Gln Val Cys Gly Pro Pro Leu Tyr Gln
               165                 170                 175

Leu Gly Ala Ala Thr Gln Ala Arg Pro Pro Pro His Ala Ser Gly Pro
           180                 185                 190

Arg Arg Arg Leu Gly Cys Glu Arg Ala Trp Asn His Ser Val Arg Glu
       195                 200                 205

Ala Gly Val Pro Leu Gly Leu Pro Ala Pro Gly Ala Arg Arg Arg Gly
   210                 215                 220
```

-continued

```
Gly Ser Ala Ser Arg Ser Leu Pro Leu Pro Lys Arg Pro Arg Gly
225                 230                 235                 240

Ala Ala Pro Glu Pro Glu Arg Thr Pro Val Gly Gln Gly Ser Trp Ala
            245                 250                 255

His Pro Gly Arg Thr Arg Gly Pro Ser Asp Arg Gly Phe Cys Val Val
            260                 265                 270

Ser Pro Ala Arg Pro Ala Glu Glu Ala Thr Ser Leu Glu Gly Ala Leu
            275                 280                 285

Ser Gly Thr Arg His Ser His Pro Ser Val Gly Arg Gln His His Ala
290                 295                 300

Gly Pro Pro Ser Thr Ser Arg Pro Pro Arg Pro Trp Asp Thr Pro Cys
305                 310                 315                 320

Pro Pro Val Tyr Ala Glu Thr Lys His Phe Leu Tyr Ser Ser Gly Asp
                325                 330                 335

Lys Glu Gln Leu Arg Pro Ser Phe Leu Leu Ser Ser Leu Arg Pro Ser
                340                 345                 350

Leu Thr Gly Ala Arg Arg Leu Val Glu Thr Ile Phe Leu Gly Ser Arg
                355                 360                 365

Pro Trp Met Pro Gly Thr Pro Arg Arg Leu Pro Arg Leu Pro Gln Arg
    370                 375                 380

Tyr Trp Gln Met Arg Pro Leu Phe Leu Glu Leu Leu Gly Asn His Ala
385                 390                 395                 400

Gln Cys Pro Tyr Gly Val Leu Leu Lys Thr His Cys Pro Leu Arg Ala
                405                 410                 415

Ala Val Thr Pro Ala Ala Gly Val Cys Ala Arg Glu Lys Pro Gln Gly
                420                 425                 430

Ser Val Ala Ala Pro Glu Glu Asp Thr Asp Pro Arg Arg Leu Val
                435                 440                 445

Gln Leu Leu Arg Gln His Ser Ser Pro Trp Gln Val Tyr Gly Phe Val
    450                 455                 460

Arg Ala Cys Leu Arg Arg Leu Val Pro Pro Gly Leu Trp Gly Ser Arg
465                 470                 475                 480

His Asn Glu Arg Arg Phe Leu Arg Asn Thr Lys Lys Phe Ile Ser Leu
                485                 490                 495

Gly Lys His Ala Lys Leu Ser Leu Gln Glu Leu Thr Trp Lys Met Ser
                500                 505                 510

Val Arg Asp Cys Ala Trp Leu Arg Arg Ser Pro Gly Val Gly Cys Val
    515                 520                 525

Pro Ala Ala Glu His Arg Leu Arg Glu Glu Ile Leu Ala Lys Phe Leu
530                 535                 540

His Trp Leu Met Ser Val Tyr Val Val Glu Leu Leu Arg Ser Phe Phe
545                 550                 555                 560

Tyr Val Thr Glu Thr Thr Phe Gln Lys Asn Arg Leu Phe Phe Tyr Arg
                565                 570                 575

Lys Ser Val Trp Ser Lys Leu Gln Ser Ile Gly Ile Arg Gln His Leu
                580                 585                 590

Lys Arg Val Gln Leu Arg Glu Leu Ser Glu Ala Glu Val Arg Gln His
                595                 600                 605

Arg Glu Ala Arg Pro Ala Leu Leu Thr Ser Arg Leu Arg Phe Ile Pro
    610                 615                 620

Lys Pro Asp Gly Leu Arg Pro Ile Val Asn Met Asp Tyr Val Val Gly
625                 630                 635                 640

Ala Arg Thr Phe Arg Arg Glu Lys Arg Ala Glu Arg Leu Thr Ser Arg
```

```
                    645                 650                 655
Val Lys Ala Leu Phe Ser Val Leu Asn Tyr Glu Arg Ala Arg Arg Pro
            660                 665                 670

Gly Leu Leu Gly Ala Ser Val Leu Gly Leu Asp Asp Ile His Arg Ala
            675                 680                 685

Trp Arg Thr Phe Val Leu Arg Val Ala Gln Asp Pro Pro Glu
            690                 695                 700

Leu Tyr Phe Val Lys Val Ala Ile Thr Gly Ala Tyr Asp Thr Ile Pro
705                 710                 715                 720

Gln Asp Arg Leu Thr Glu Val Ile Ala Ser Ile Ile Lys Pro Gln Asn
            725                 730                 735

Thr Tyr Cys Val Arg Arg Tyr Ala Val Val Gln Lys Ala Ala His Gly
            740                 745                 750

His Val Arg Lys Ala Phe Lys Ser His Val Ser Thr Leu Thr Asp Leu
            755                 760                 765

Gln Pro Tyr Met Arg Gln Phe Val Ala His Leu Gln Glu Thr Ser Pro
            770                 775                 780

Leu Arg Asp Ala Val Val Ile Glu Gln Ser Ser Ser Leu Asn Glu Ala
785                 790                 795                 800

Ser Ser Gly Leu Phe Asp Val Phe Leu Arg Phe Met Cys His His Ala
            805                 810                 815

Val Arg Ile Arg Gly Lys Ser Tyr Val Gln Cys Gln Gly Ile Pro Gln
            820                 825                 830

Gly Ser Ile Leu Ser Thr Leu Leu Cys Ser Leu Cys Tyr Gly Asp Met
            835                 840                 845

Glu Asn Lys Leu Phe Ala Gly Ile Arg Arg Asp Gly Leu Leu Leu Arg
            850                 855                 860

Leu Val Asp Asp Phe Leu Leu Val Thr Pro His Leu Thr His Ala Lys
865                 870                 875                 880

Thr Phe Leu Arg Thr Leu Val Arg Gly Val Pro Glu Tyr Gly Cys Val
            885                 890                 895

Val Asn Leu Arg Lys Thr Val Val Asn Phe Pro Val Glu Asp Glu Ala
            900                 905                 910

Leu Gly Gly Thr Ala Phe Val Gln Met Pro Ala His Gly Leu Phe Pro
            915                 920                 925

Trp Cys Gly Leu Leu Leu Asp Thr Arg Thr Leu Glu Val Gln Ser Asp
            930                 935                 940

Tyr Ser Ser Tyr Ala Arg Thr Ser Ile Arg Ala Ser Leu Thr Phe Asn
945                 950                 955                 960

Arg Gly Phe Lys Ala Gly Arg Asn Met Arg Arg Lys Leu Phe Gly Val
            965                 970                 975

Leu Arg Leu Lys Cys His Ser Leu Phe Leu Asp Leu Gln Val Asn Ser
            980                 985                 990

Leu Gln Thr Val Cys Thr Asn Ile Tyr Lys Ile Leu Leu Leu Gln Ala
            995                 1000                1005

Tyr Arg Phe His Ala Cys Val Leu Gln Leu Pro Phe His Gln Gln Val
            1010                1015                1020

Trp Lys Asn Pro Thr Phe Phe Leu Arg Val Ile Ser Asp Thr Ala Ser
1025                1030                1035                1040

Leu Cys Tyr Ser Ile Leu Lys Ala Lys Asn Ala Gly Met Ser Leu Gly
            1045                1050                1055

Ala Lys Gly Ala Ala Gly Pro Leu Pro Ser Glu Ala Val Gln Trp Leu
            1060                1065                1070
```

-continued

Cys His Gln Ala Phe Leu Leu Lys Leu Thr Arg His Arg Val Thr Tyr
        1075                1080                1085

Val Pro Leu Leu Gly Ser Leu Arg Thr Ala Gln Thr Gln Leu Ser Arg
    1090                1095                1100

Lys Leu Pro Gly Thr Thr Leu Thr Ala Leu Glu Ala Ala Ala Asn Pro
1105                1110                1115                1120

Ala Leu Pro Ser Asp Phe Lys Thr Ile Leu Asp Ser Arg Ala Pro Gln
            1125                1130                1135

Ser Ile Thr Glu Leu Cys Ser Glu Tyr Arg Asn Thr Gln Ile Tyr Thr
    1140                1145                1150

Ile Asn Asp Lys Ile Leu Ser Tyr Thr Glu Ser Met Ala Gly Lys Arg
        1155                1160                1165

Glu Met Val Ile Ile Thr Phe Lys Ser Gly Ala Thr Phe Gln Val Glu
    1170                1175                1180

Val Pro Gly Ser Gln His Ile Asp Ser Gln Lys Lys Ala Ile Glu Arg
1185                1190                1195                1200

Met Lys Asp Thr Leu Arg Ile Thr Tyr Leu Thr Glu Thr Lys Ile Asp
            1205                1210                1215

Lys Leu Cys Val Trp Asn Asn Lys Thr Pro Asn Ser Ile Ala Ala Ile
        1220                1225                1230

Ser Met Glu Asn
    1235

<210> SEQ ID NO 7
<211> LENGTH: 3681
<212> TYPE: DNA
<213> ORGANISM: Artificial Sequence
<220> FEATURE:
<223> OTHER INFORMATION: mTERT(AI)-LTBopt

<400> SEQUENCE: 7

```
accagagccc ccagatgccc tgccgtgaga agcctgctgc ggagccggta cagagaagtg      60
tggcccctgg ccacctttgt gaggagactg ggccctgagg caggagact  ggtgcagcct     120
ggcgacccca aaatctacag gaccctggtg gcccagtgtc tggtgtgtat gcactggggc     180
agccagcccc ctcccgccga cctgagcttc accaggtgt  ccagcctgaa ggaactggtg     240
gccagagtgg tgcagagact gtgcgagcgg aacgagagaa acgtgctggc cttcggcttc     300
gagctgctga cgaggccag  aggcggccct cccatggcct tcaccagctc tgtgaggagc     360
tacctgccca caccgtgat  cgagaccctg agagtgagcg cgcctggat  gctgctgctg     420
agcagagtgg gcgatgacct gctggtgtac ctgctggccc actgcgccct gtatctgctg     480
gtgcccccca gctgcgccta ccaggtgtgc ggatccccc  tgtaccagat tgcgccacc      540
accgacatct ggcccagcgt gtctgccagc tacagaccca ccagacctgt gggccggaac     600
ttcaccaacc tgcggttcct gcagcagatc aagagcagca gcagacagga ggcccccaag     660
cccctggccc tgcccagcag aggcaccaag agacacctga gcctgaccag caccagcgtg     720
cccagcgcca agaaagccag atgctacccc gtgcctagag tggaggaggg ccctcacaga     780
caggtgctgc ccacccccag cggcaagagc tgggtgccca gccccgccag aagcccgaa      840
gtgcccaccg ccgagaagga cctgagcagc aagggcaaag tgagcgacct gtctctgagc     900
ggcagcgtgt gttgcaagca caagcccagc agcaccagcc tgctgagccc cccagacag      960
aacgccttcc agctgaggcc tttcatcgag acccggcact tcctgtacag cagaggcgat    1020
ggccaggaga gactgaaccc cagcttcctg ctgagcaacc tgcagcctaa cctgaccggc    1080
gccagacgcc tggtggagat catcttcctg ggcagcagac ccagaaccag cggccctctg    1140
```

```
tgcagaaccc accggctgag caggcggtac tggcagatga gacccctgtt ccagcagctg      1200
ctggtgaacc acgccgagtg ccagtatgtg cggctgctga ggagccactg cagattcagg      1260
accgccaacc agcaggtgac cgacgccctg aacaccagcc ccctcacct gatggatctg       1320 ctgaggctgc acagcagccc ctggcaggtg tacggcttcc tgagagcctg cctgtgcaaa      1380
gtggtgtccg ccagcctgtg gggcaccaga cacaacgagc ggcggttctt caagaatctg      1440
aagaagttca tcagcctggg caagtacggc aagctgagcc tgcaggaact gatgtggaag      1500
atgaaagtgg aggactgcca ctggctgaga agcagcccg gcaaggacag agtgcctgcc       1560
gccgagcaca gactgaggga gagaatcctg gccacattcc tgttctggct gatggacacc      1620
tacgtggtgc agctgctgcg gtccttcttc tacatcaccg agagcacctt ccagaagaac      1680
cggctgttct tctaccggaa gtctgtgtgg agcaagctgc agagcatcgg agtgagacag      1740
cacctggaga gagtgaggct gagagagctg agccaggagg aagtgagaca ccaccaggat      1800
acctggctgg ccatgcccat ctgccggctg agattcatcc caagcccaa cggcctgaga       1860 cccatcgtga acatgagcta cagcatgggc acaagagccc tgggcagaag aaagcaggcc      1920
cagcacttca cccagcggct gaaaaccctg ttctccatgc tgaactacga gcggaccaag      1980
cacccacacc tgatgggcag cagcgtgctg ggcatgaacg acatctaccg gacctggaga      2040
gccttcgtgc tgagagtgcg ggccctggac cagacccctc ggatgtactt cgtgaaggcc      2100
gccatcaccg gcgcctacga cgccatcccc cagggcaaac tggtggaagt ggtggccaac      2160
atgatcagga cagcgagtc cacctactgc atcaggcagt acgccgtggt gagaagagac       2220
agccagggcc aggtgcacaa gagcttccgg agacaggtga ccaccctgag cgatctgcag      2280
ccttacatgg ccagttcct gaagcacctg caggatagcg acgccagcgc cctgagaaat       2340
agcgtggtga tcgagcagag catcagcatg aacgagtcca gcagcagcct gttcgacttc      2400
ttcctgcact tcctgaggca cagcgtggtg aagatcggcg acagatgcta cacccagtgt      2460
cagggcatcc ctcagggctc tagcctgagc accctgctgt gtagcctgtg cttcggcgac      2520
atggagaata gctgttcgc cgaagtgcag agagatggcc tgctgctgcg cttcgtggac       2580
gatttcctgc tggtgacccc acacctggac caggccaaga ccttcctgag cacactggtg      2640
cacggcgtgc ccgagtacgg ctgcatgatc aatctgcaga aaaccgtggt gaacttccct      2700
gtggagcccg gcaccctggg cggagccgcc ccttaccagc tgcccgccca ctgcctgttc      2760
ccctggtgcg gactgctgct ggatacccag accctggaag tgttctgcga ctacagcggc      2820
tacgcccaga ccagcatcaa gaccagcctg accttccaga gcgtgttcaa ggccggcaag      2880
accatgagga caagctgct gagcgtgctg agactgaagt gccacggcct gttcctggat       2940
ctgcaggtga acagcctgca gaccgtgtgt atcaacatct acaagatttt cctgctgcag      3000
gcctacagat tccacgcctg cgtgatccag ctgcccttcg accagagagt gcggaagaac      3060 ctgacccttct tcctggggat catcagcagc caggccagct gctgctacgc catcctgaaa      3120
gtgaagaacc ccggcatgac cctgaaggcc agcggcagct ccctcccga ggccgcccac       3180 tggctgtgct accaggcctt tctgctgaag ctggccgccc acagcgtgat ctacaagtgc      3240
ctgctgggcc ctctgagaac cgcccagaag ctgctgtgcc ggaagctgcc gaggccacc       3300 atgaccattc tgaaagccgc cgccgacccc gccctgagca ccgacttcca gaccatcctg      3360
gactctagag cccctcagag catcaccgag ctgtgcagcg agtaccggaa cacccagatt      3420
tacaccatca cgacaagat cctgagctac accgagtcta tggccggcaa gcgggagatg       3480
gtgatcatca ccttcaagag cggcgccacc tttcaggtgg aagtgcctgg cagccagcac      3540
```

```
atcgacagcc agaagaaggc catcgagcgg atgaaggaca ccctgcggat cacctacctg    3600
accgagacca agatcgacaa gctgtgtgtg tggaacaaca agacccccaa cagcatcgcc    3660
gccatctcta tggagaactg a                                              3681
```

<210> SEQ ID NO 8
<211> LENGTH: 1232
<212> TYPE: PRT
<213> ORGANISM: Artificial Sequence
<220> FEATURE:
<223> OTHER INFORMATION: mTERT(AI)-LTBopt

<400> SEQUENCE: 8

```
Thr Arg Ala Pro Arg Cys Pro Ala Val Arg Ser Leu Leu Arg Ser Arg
  1               5                  10                  15

Tyr Arg Glu Val Trp Pro Leu Ala Thr Phe Val Arg Arg Leu Gly Pro
             20                  25                  30

Glu Gly Arg Arg Leu Val Gln Pro Gly Asp Pro Lys Ile Tyr Arg Thr
         35                  40                  45

Leu Val Ala Gln Cys Leu Val Cys Met His Trp Gly Ser Gln Pro Pro
     50                  55                  60

Pro Ala Asp Leu Ser Phe His Gln Val Ser Ser Leu Lys Glu Leu Val
 65                  70                  75                  80

Ala Arg Val Val Gln Arg Leu Cys Glu Arg Asn Glu Arg Asn Val Leu
                 85                  90                  95

Ala Phe Gly Phe Glu Leu Leu Asn Glu Ala Arg Gly Gly Pro Pro Met
            100                 105                 110

Ala Phe Thr Ser Ser Val Arg Ser Tyr Leu Pro Asn Thr Val Ile Glu
        115                 120                 125

Thr Leu Arg Val Ser Gly Ala Trp Met Leu Leu Leu Ser Arg Val Gly
    130                 135                 140

Asp Asp Leu Leu Val Tyr Leu Leu Ala His Cys Ala Leu Tyr Leu Leu
145                 150                 155                 160

Val Pro Pro Ser Cys Ala Tyr Gln Val Cys Gly Ser Pro Leu Tyr Gln
                165                 170                 175

Ile Cys Ala Thr Thr Asp Ile Trp Pro Ser Val Ser Ala Ser Tyr Arg
            180                 185                 190

Pro Thr Arg Pro Val Gly Arg Asn Phe Thr Asn Leu Arg Phe Leu Gln
        195                 200                 205

Gln Ile Lys Ser Ser Arg Gln Glu Ala Pro Lys Pro Leu Ala Leu
    210                 215                 220

Pro Ser Arg Gly Thr Lys Arg His Leu Ser Leu Thr Ser Thr Ser Val
225                 230                 235                 240

Pro Ser Ala Lys Lys Ala Arg Cys Tyr Pro Val Pro Arg Val Glu Glu
                245                 250                 255

Gly Pro His Arg Gln Val Leu Pro Thr Pro Ser Gly Lys Ser Trp Val
            260                 265                 270

Pro Ser Pro Ala Arg Ser Pro Glu Val Pro Thr Ala Glu Lys Asp Leu
        275                 280                 285

Ser Ser Lys Gly Lys Val Ser Asp Leu Ser Ser Gly Ser Val Cys
    290                 295                 300

Cys Lys His Lys Pro Ser Ser Thr Ser Leu Leu Ser Pro Arg Gln
305                 310                 315                 320

Asn Ala Phe Gln Leu Arg Pro Phe Ile Glu Thr Arg His Phe Leu Tyr
                325                 330                 335
```

-continued

Ser Arg Gly Asp Gly Gln Glu Arg Leu Asn Pro Ser Phe Leu Leu Ser
            340                 345                 350

Asn Leu Gln Pro Asn Leu Thr Gly Ala Arg Arg Leu Val Glu Ile Ile
            355                 360                 365

Phe Leu Gly Ser Arg Pro Arg Thr Ser Gly Pro Leu Cys Arg Thr His
        370                 375                 380

Arg Leu Ser Arg Arg Tyr Trp Gln Met Arg Pro Leu Phe Gln Gln Leu
385                 390                 395                 400

Leu Val Asn His Ala Glu Cys Gln Tyr Val Arg Leu Leu Arg Ser His
                405                 410                 415

Cys Arg Phe Arg Thr Ala Asn Gln Gln Val Thr Asp Ala Leu Asn Thr
            420                 425                 430

Ser Pro Pro His Leu Met Asp Leu Leu Arg Leu His Ser Ser Pro Trp
        435                 440                 445

Gln Val Tyr Gly Phe Leu Arg Ala Cys Leu Cys Lys Val Val Ser Ala
            450                 455                 460

Ser Leu Trp Gly Thr Arg His Asn Glu Arg Arg Phe Phe Lys Asn Leu
465                 470                 475                 480

Lys Lys Phe Ile Ser Leu Gly Lys Tyr Gly Lys Leu Ser Leu Gln Glu
                485                 490                 495

Leu Met Trp Lys Met Lys Val Glu Asp Cys His Trp Leu Arg Ser Ser
            500                 505                 510

Pro Gly Lys Asp Arg Val Pro Ala Ala Glu His Arg Leu Arg Glu Arg
        515                 520                 525

Ile Leu Ala Thr Phe Leu Phe Trp Leu Met Asp Thr Tyr Val Val Gln
            530                 535                 540

Leu Leu Arg Ser Phe Phe Tyr Ile Thr Glu Ser Thr Phe Gln Lys Asn
545                 550                 555                 560

Arg Leu Phe Phe Tyr Arg Lys Ser Val Trp Ser Lys Leu Gln Ser Ile
                565                 570                 575

Gly Val Arg Gln His Leu Glu Arg Val Arg Leu Arg Glu Leu Ser Gln
            580                 585                 590

Glu Glu Val Arg His His Gln Asp Thr Trp Leu Ala Met Pro Ile Cys
        595                 600                 605

Arg Leu Arg Phe Ile Pro Lys Pro Asn Gly Leu Arg Pro Ile Val Asn
        610                 615                 620

Met Ser Tyr Ser Met Gly Thr Arg Ala Leu Gly Arg Arg Lys Gln Ala
625                 630                 635                 640

Gln His Phe Thr Gln Arg Leu Lys Thr Leu Phe Ser Met Leu Asn Tyr
                645                 650                 655

Glu Arg Thr Lys His Pro His Leu Met Gly Ser Ser Val Leu Gly Met
            660                 665                 670

Asn Asp Ile Tyr Arg Thr Trp Arg Ala Phe Val Leu Arg Val Arg Ala
        675                 680                 685

Leu Asp Gln Thr Pro Arg Met Tyr Phe Val Lys Ala Ala Ile Thr Gly
    690                 695                 700

Ala Tyr Asp Ala Ile Pro Gln Gly Lys Leu Val Glu Val Ala Asn
705                 710                 715                 720

Met Ile Arg His Ser Glu Ser Thr Tyr Cys Ile Arg Gln Tyr Ala Val
                725                 730                 735

Val Arg Arg Asp Ser Gln Gly Gln Val His Lys Ser Phe Arg Arg Gln
            740                 745                 750

Val Thr Thr Leu Ser Asp Leu Gln Pro Tyr Met Gly Gln Phe Leu Lys
        755                 760                 765

-continued

His Leu Gln Asp Ser Asp Ala Ser Ala Leu Arg Asn Ser Val Val Ile
770                 775                 780

Glu Gln Ser Ile Ser Met Asn Glu Ser Ser Ser Leu Phe Asp Phe
785                 790                 795                 800

Phe Leu His Phe Leu Arg His Ser Val Val Lys Ile Gly Asp Arg Cys
                805                 810                 815

Tyr Thr Gln Cys Gln Gly Ile Pro Gln Gly Ser Ser Leu Ser Thr Leu
            820                 825                 830

Leu Cys Ser Leu Cys Phe Gly Asp Met Glu Asn Lys Leu Phe Ala Glu
        835                 840                 845

Val Gln Arg Asp Gly Leu Leu Leu Arg Phe Val Asp Asp Phe Leu Leu
    850                 855                 860

Val Thr Pro His Leu Asp Gln Ala Lys Thr Phe Leu Ser Thr Leu Val
865                 870                 875                 880

His Gly Val Pro Glu Tyr Gly Cys Met Ile Asn Leu Gln Lys Thr Val
                885                 890                 895

Val Asn Phe Pro Val Glu Pro Gly Thr Leu Gly Gly Ala Ala Pro Tyr
            900                 905                 910

Gln Leu Pro Ala His Cys Leu Phe Pro Trp Cys Gly Leu Leu Leu Asp
        915                 920                 925

Thr Gln Thr Leu Glu Val Phe Cys Asp Tyr Ser Gly Tyr Ala Gln Thr
    930                 935                 940

Ser Ile Lys Thr Ser Leu Thr Phe Gln Ser Val Phe Lys Ala Gly Lys
945                 950                 955                 960

Thr Met Arg Asn Lys Leu Leu Ser Val Leu Arg Leu Lys Cys His Gly
                965                 970                 975

Leu Phe Leu Asp Leu Gln Val Asn Ser Leu Gln Thr Val Cys Ile Asn
            980                 985                 990

Ile Tyr Lys Ile Phe Leu Leu Gln Ala Tyr Arg Phe His Ala Cys Val
        995                 1000                1005

Ile Gln Leu Pro Phe Asp Gln Arg Val Arg Lys Asn Leu Thr Phe Phe
    1010                1015                1020

Leu Gly Ile Ile Ser Ser Gln Ala Ser Cys Cys Tyr Ala Ile Leu Lys
1025                1030                1035                1040

Val Lys Asn Pro Gly Met Thr Leu Lys Ala Ser Gly Ser Phe Pro Pro
                1045                1050                1055

Glu Ala Ala His Trp Leu Cys Tyr Gln Ala Phe Leu Leu Lys Leu Ala
            1060                1065                1070

Ala His Ser Val Ile Tyr Lys Cys Leu Leu Gly Pro Leu Arg Thr Ala
        1075                1080                1085

Gln Lys Leu Leu Cys Arg Lys Leu Pro Glu Ala Thr Met Thr Ile Leu
    1090                1095                1100

Lys Ala Ala Ala Asp Pro Ala Leu Ser Thr Asp Phe Gln Thr Ile Leu
1105                1110                1115                1120

Asp Ser Arg Ala Pro Gln Ser Ile Thr Glu Leu Cys Ser Glu Tyr Arg
                1125                1130                1135

Asn Thr Gln Ile Tyr Thr Ile Asn Asp Lys Ile Leu Ser Tyr Thr Glu
            1140                1145                1150

Ser Met Ala Gly Lys Arg Glu Met Val Ile Ile Thr Phe Lys Ser Gly
        1155                1160                1165

Ala Thr Phe Gln Val Glu Val Pro Gly Ser Gln His Ile Asp Ser Gln
    1170                1175                1180

Lys Lys Ala Ile Glu Arg Met Lys Asp Thr Leu Arg Ile Thr Tyr Leu

```
                1185              1190              1195              1200
Thr Glu Thr Lys Ile Asp Lys Leu Cys Val Trp Asn Asn Lys Thr Pro
                    1205              1210              1215

Asn Ser Ile Ala Ala Ile Ser Met Glu Asn Ser Glu Gln Ile Asp Asn
                    1220              1225              1230

<210> SEQ ID NO 9
<211> LENGTH: 3393
<212> TYPE: DNA
<213> ORGANISM: Artificial Sequence
<220> FEATURE:
<223> OTHER INFORMATION: hTERT(AI)

<400> SEQUENCE: 9
cccagagccc ccagatgcag agccgtgcgg agcctgctgc ggagccacta ccgggaagtg      60
ctgcccctgg ccaccttcgt gcggcggctg gcccccagg gctggcggct ggtgcagcgg      120
ggcgaccctg ccgccttccg ggccctggtg gctcagtgcc tggtgtgcgt gccctgggac     180
gccagacccc cccagccgc ccctagcttc ggcaggtga gctgcctgaa ggaactggtg       240
gccagagtgc tgcagcggct gtgcgagaga ggcgccaaga acgtgctggc cttcggcttc    300
gccctgctgg acggcgccag aggcggccct cccgaggcct tcaccacaag cgtgcggagc    360
tacctgccca acaccgtgac cgacgccctg cggggcagcg cgcctgggg cctgctgctg     420 agaagagtgg gcgacgacgt gctggtgcac ctgctggccc ggtgcgccct gttcgtgctg    480
gtggccccca gctgcgccta ccaggtgtgc ggcccacccc tgtaccagct gggagccgcc    540
acccaggcca ggcccccacc ccacgccagc ggccccagac ggagactggg ctgcgagcgg    600
gcctggaacc acagcgtgag agaggccggc gtgcccctgg cctgccagcc cctggcgcc    660 agaagaagag gcggcagcgc cagccggagc ctgcccctgc ccaagcggcc agaagaggc     720 gctgcccccg agcccgagcg gacccccgtg gcccagggca gctgggccca ccccggcaga    780
accagaggcc ccagcgaccg gggcttctgc gtggtgagcc ccgccagacc cgccgaggag    840
gccacaagcc tggagggcgc cctgagcggc acccggcaca gccacccag cgtgggccgg    900 cagcaccacg ccgacccccc cagcaccagc agacccccca ccctggga cacccccctgc    960 cccctgtgt acgccgagac caagcacttc ctgtacagca gcggcgacaa ggagcagctg    1020
cggcccagct cctgctgag cagcctgaga cccagcctga ccggcgccag agactggtg     1080 gagaccatct tcctgggcag ccggccctgg atgcccggca ccccccggag actgccccgg    1140
ctgccccagc ggtactggca gatgcggccc ctgttcctgg agctgctggg caaccacgcc    1200
cagtgcccct acggcgtgct gctgaaaacc cactgccccc tgagagccgc cgtgaccccc    1260
gctgccggcg tgtgcgccag agagaagccc cagggcagcg tggccgctcc cgaggaggag    1320
gacaccgacc ccagacgcct ggtgcagctg ctgcggcagc acagcagccc ttggcaggtg    1380
tacggcttcg tgcgggcctg cctgagaagg ctggtgcccc ctggcctgtg ggcagcaga    1440 cacaacgagc ggcggttcct gcggaacacc aagaagttca tcagcctggg gaagcacgcc    1500
aagctgagcc tgcaggaact gacctggaag atgagcgtgc gggactgcgc ctggctgcgg    1560
cggagccctg gcgtgggctg cgtgccagcc gccgagcacc ggctgcggga ggagatcctg    1620
gccaagttcc tgcactggct gatgagcgtg tacgtggtgg aactgctgcg gtccttcttc    1680
tacgtgaccg aaaccacctt ccagaagaac cggctgttct ctaccggaa gagcgtgtgg    1740 agcaagctgc agagcatcgg catcaggcag cacctgaaga gagtgcagct gcgggagctg    1800
agcgaggccg aagtgagaca gcaccgggag gccagacctg ccctgctgac cagccggctg    1860
```

-continued

```
cggttcatcc ccaagcccga cggcctgcgg cccatcgtga acatggacta cgtggtgggc      1920
gccagaacct tccggcggga gaagcgggcc gagcggctga ccagcagagt gaaggccctg      1980
ttcagcgtgc tgaactacga gcgggccagg agacccggcc tgctgggcgc cagcgtgctg      2040
ggcctggacg acatccaccg ggcctggcgg accttcgtgc tgagagtgcg ggcccaggac      2100
cccccacccg agctgtactt cgtgaaagtg gccatcaccg gcgcctacga caccatcccc      2160
caggaccggc tgaccgaagt gatcgccagc atcatcaagc ccagaacac ctactgcgtg       2220 cggcggtacg ccgtggtgca aaggccgcc cacggccacg tgcggaaggc cttcaagagc       2280
cacgtgagca ccctgaccga cctgcagccc tacatgcggc agttcgtggc ccacctgcag      2340
gagaccagcc ccctgcggga tgccgtggtg atcgagcaga gcagcagcct gaacgaggcc     2400
agcagcggcc tgttcgacgt gttcctgcgc ttcatgtgcc accacgccgt gcggatccgg      2460
ggcaagagct acgtgcagtg ccagggcatc cctcagggca gcatcctgag cacactgctg     2520
tgctctctgt gctacggcga catggagaac aagctgttcg ccggcatccg gcgggacgga     2580
ctgctgctgc gcctggtgga cgacttcctg ctggtgaccc tcacctgac ccacgccaag      2640 accttcctgc ggaccctggt gcggggcgtg cccgagtacg gctgtgtggt gaacctgcgc     2700
aagaccgtgg tgaacttccc cgtggaggac gaggccctgg gcggcacagc cttcgtgcag    2760
atgcccgccc atggcctgtt cccttggtgc gggctgctgc tggacacccg gaccctggaa    2820
gtgcagagcg actacagcag ctacgcccgg accagcatcc gggccagcct gacattcaac    2880
cgcggcttca aggccggcag aaacatgcgg cggaagctgt ttggcgtgct gcggctgaag    2940
tgccacagcc tgtttctgga cctgcaggtg aacagcctgc agaccgtgtg caccaacatc    3000
tacaagatcc tgctgctgca ggcctaccgg ttccacgcct gcgtgctgca gctgcccttc    3060
catcagcagg tgtggaagaa ccccaccttc ttcctgcgcg tgatctctga caccgccagc    3120
ctgtgctaca gcattctgaa ggccaagaac gccggcatga gcctgggcgc caagggcgct    3180
gccggacccc tgcccagcga ggccgtgcag tggctgtgtc accaggcctt tctgctgaag   3240
ctgacccggc accgcgtgac ctacgtgccc ctgctgggaa gcctgcggac cgcccagacc    3300
cagctgagcc ggaagctgcc tggcaccacc ctgacagccc tggaggccgc tgccaaccc    3360 gccctgccta cgacttcaa gaccatcctg gac                                   3393
```

<210> SEQ ID NO 10
<211> LENGTH: 1137
<212> TYPE: PRT
<213> ORGANISM: Artificial Sequence
<220> FEATURE:
<223> OTHER INFORMATION: hTERT(AI)

<400> SEQUENCE: 10

```
Pro Arg Ala Pro Arg Cys Arg Ala Val Arg Ser Leu Leu Arg Ser His
1               5                   10                  15

Tyr Arg Glu Val Leu Pro Leu Ala Thr Phe Val Arg Arg Leu Gly Pro
            20                  25                  30

Gln Gly Trp Arg Leu Val Gln Arg Gly Asp Pro Ala Ala Phe Arg Ala
        35                  40                  45

Leu Val Ala Gln Cys Leu Val Cys Val Pro Trp Asp Ala Arg Pro Pro
    50                  55                  60

Pro Ala Ala Pro Ser Phe Arg Gln Val Ser Cys Leu Lys Glu Leu Val
65                  70                  75                  80

Ala Arg Val Leu Gln Arg Leu Cys Glu Arg Gly Ala Lys Asn Val Leu
                85                  90                  95
```

```
Ala Phe Gly Phe Ala Leu Leu Asp Gly Ala Arg Gly Pro Pro Glu
            100                 105                 110

Ala Phe Thr Thr Ser Val Arg Ser Tyr Leu Pro Asn Thr Val Thr Asp
            115                 120                 125

Ala Leu Arg Gly Ser Gly Ala Trp Gly Leu Leu Arg Arg Val Gly
130             135                 140

Asp Asp Val Leu Val His Leu Leu Ala Arg Cys Ala Leu Phe Val Leu
145                 150                 155                 160

Val Ala Pro Ser Cys Ala Tyr Gln Val Cys Gly Pro Leu Tyr Gln
                165                 170                 175

Leu Gly Ala Ala Thr Gln Ala Arg Pro Pro His Ala Ser Gly Pro
            180                 185                 190

Arg Arg Arg Leu Gly Cys Glu Arg Ala Trp Asn His Ser Val Arg Glu
            195                 200                 205

Ala Gly Val Pro Leu Gly Leu Pro Ala Pro Gly Ala Arg Arg Gly
            210                 215                 220

Gly Ser Ala Ser Arg Ser Leu Pro Leu Pro Lys Arg Pro Arg Gly
225                 230                 235                 240

Ala Ala Pro Glu Pro Glu Arg Thr Pro Val Gly Gln Gly Ser Trp Ala
                245                 250                 255

His Pro Gly Arg Thr Arg Gly Pro Ser Asp Arg Gly Phe Cys Val Val
            260                 265                 270

Ser Pro Ala Arg Pro Ala Glu Glu Ala Thr Ser Leu Glu Gly Ala Leu
            275                 280                 285

Ser Gly Thr Arg His Ser His Pro Ser Val Gly Arg Gln His His Ala
            290                 295                 300

Gly Pro Pro Ser Thr Ser Arg Pro Pro Arg Pro Trp Asp Thr Pro Cys
305                 310                 315                 320

Pro Pro Val Tyr Ala Glu Thr Lys His Phe Leu Tyr Ser Ser Gly Asp
                325                 330                 335

Lys Glu Gln Leu Arg Pro Ser Phe Leu Leu Ser Ser Leu Arg Pro Ser
            340                 345                 350

Leu Thr Gly Ala Arg Arg Leu Val Glu Thr Ile Phe Leu Gly Ser Arg
            355                 360                 365

Pro Trp Met Pro Gly Thr Pro Arg Arg Leu Pro Arg Leu Pro Gln Arg
370                 375                 380

Tyr Trp Gln Met Arg Pro Leu Phe Leu Glu Leu Gly Asn His Ala
385             390                 395                 400

Gln Cys Pro Tyr Gly Val Leu Leu Lys Thr His Cys Pro Leu Arg Ala
                405                 410                 415

Ala Val Thr Pro Ala Ala Gly Val Cys Ala Arg Glu Lys Pro Gln Gly
            420                 425                 430

Ser Val Ala Ala Pro Glu Glu Asp Thr Asp Pro Arg Arg Leu Val
            435                 440                 445

Gln Leu Leu Arg Gln His Ser Ser Pro Trp Gln Val Tyr Gly Phe Val
            450                 455                 460

Arg Ala Cys Leu Arg Arg Leu Val Pro Pro Gly Leu Trp Gly Ser Arg
465                 470                 475                 480

His Asn Glu Arg Arg Phe Leu Arg Asn Thr Lys Lys Phe Ile Ser Leu
                485                 490                 495

Gly Lys His Ala Lys Leu Ser Leu Gln Glu Leu Thr Trp Lys Met Ser
            500                 505                 510

Val Arg Asp Cys Ala Trp Leu Arg Arg Ser Pro Gly Val Gly Cys Val
            515                 520                 525
```

```
Pro Ala Ala Glu His Arg Leu Arg Glu Glu Ile Leu Ala Lys Phe Leu
    530                 535                 540

His Trp Leu Met Ser Val Tyr Val Val Glu Leu Leu Arg Ser Phe Phe
545                 550                 555                 560

Tyr Val Thr Glu Thr Thr Phe Gln Lys Asn Arg Leu Phe Phe Tyr Arg
                565                 570                 575

Lys Ser Val Trp Ser Lys Leu Gln Ser Ile Gly Ile Arg Gln His Leu
            580                 585                 590

Lys Arg Val Gln Leu Arg Glu Leu Ser Glu Ala Glu Val Arg Gln His
        595                 600                 605

Arg Glu Ala Arg Pro Ala Leu Leu Thr Ser Arg Leu Arg Phe Ile Pro
    610                 615                 620

Lys Pro Asp Gly Leu Arg Pro Ile Val Asn Met Asp Tyr Val Val Gly
625                 630                 635                 640

Ala Arg Thr Phe Arg Arg Glu Lys Arg Ala Glu Arg Leu Thr Ser Arg
                645                 650                 655

Val Lys Ala Leu Phe Ser Val Leu Asn Tyr Glu Arg Ala Arg Arg Pro
            660                 665                 670

Gly Leu Leu Gly Ala Ser Val Leu Gly Leu Asp Asp Ile His Arg Ala
        675                 680                 685

Trp Arg Thr Phe Val Leu Arg Val Arg Ala Gln Asp Pro Pro Glu
    690                 695                 700

Leu Tyr Phe Val Lys Val Ala Ile Thr Gly Ala Tyr Asp Thr Ile Pro
705                 710                 715                 720

Gln Asp Arg Leu Thr Glu Val Ile Ala Ser Ile Ile Lys Pro Gln Asn
                725                 730                 735

Thr Tyr Cys Val Arg Arg Tyr Ala Val Val Gln Lys Ala Ala His Gly
            740                 745                 750

His Val Arg Lys Ala Phe Lys Ser His Val Ser Thr Leu Thr Asp Leu
        755                 760                 765

Gln Pro Tyr Met Arg Gln Phe Val Ala His Leu Gln Glu Thr Ser Pro
    770                 775                 780

Leu Arg Asp Ala Val Val Ile Glu Gln Ser Ser Ser Leu Asn Glu Ala
785                 790                 795                 800

Ser Ser Gly Leu Phe Asp Val Phe Leu Arg Phe Met Cys His His Ala
                805                 810                 815

Val Arg Ile Arg Gly Lys Ser Tyr Val Gln Cys Gln Gly Ile Pro Gln
            820                 825                 830

Gly Ser Ile Leu Ser Thr Leu Leu Cys Ser Leu Cys Tyr Gly Asp Met
        835                 840                 845

Glu Asn Lys Leu Phe Ala Gly Ile Arg Arg Asp Gly Leu Leu Leu Arg
    850                 855                 860

Leu Val Asp Asp Phe Leu Leu Val Thr Pro His Leu Thr His Ala Lys
865                 870                 875                 880

Thr Phe Leu Arg Thr Leu Val Arg Gly Val Pro Glu Tyr Gly Cys Val
                885                 890                 895

Val Asn Leu Arg Lys Thr Val Val Asn Phe Pro Val Glu Asp Glu Ala
            900                 905                 910

Leu Gly Gly Thr Ala Phe Val Gln Met Pro Ala His Gly Leu Phe Pro
        915                 920                 925

Trp Cys Gly Leu Leu Leu Asp Thr Arg Thr Leu Glu Val Gln Ser Asp
    930                 935                 940

Tyr Ser Ser Tyr Ala Arg Thr Ser Ile Arg Ala Ser Leu Thr Phe Asn
```

```
                  945                 950                 955                 960
Arg Gly Phe Lys Ala Gly Arg Asn Met Arg Arg Lys Leu Phe Gly Val
                    965                 970                 975
Leu Arg Leu Lys Cys His Ser Leu Phe Leu Asp Leu Gln Val Asn Ser
                980                 985                 990
Leu Gln Thr Val Cys Thr Asn Ile Tyr Lys Ile Leu Leu Gln Ala
        995                1000                1005
Tyr Arg Phe His Ala Cys Val Leu Gln Leu Pro Phe His Gln Val
       1010                1015                1020
Trp Lys Asn Pro Thr Phe Phe Leu Arg Val Ile Ser Asp Thr Ala Ser
1025                1030                1035                1040
Leu Cys Tyr Ser Ile Leu Lys Ala Lys Asn Ala Gly Met Ser Leu Gly
                1045                1050                1055
Ala Lys Gly Ala Ala Gly Pro Leu Pro Ser Glu Ala Val Gln Trp Leu
                1060                1065                1070
Cys His Gln Ala Phe Leu Leu Lys Leu Thr Arg His Arg Val Thr Tyr
            1075                1080                1085
Val Pro Leu Leu Gly Ser Leu Arg Thr Ala Gln Thr Gln Leu Ser Arg
        1090                1095                1100
Lys Leu Pro Gly Thr Thr Leu Thr Ala Leu Glu Ala Ala Asn Pro
1105                1110                1115                1120
Ala Leu Pro Ser Asp Phe Lys Thr Ile Leu Asp Ser Glu Gln Ile Asp
                1125                1130                1135

Asn

<210> SEQ ID NO 11
<211> LENGTH: 3399
<212> TYPE: DNA
<213> ORGANISM: Homo Sapiens

<400> SEQUENCE: 11
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgccccccgc cgcccccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcgggggc cccccgagg ccttcaccac cagcgtgcgc     360
agctacctgc ccaacacggt gaccgacgca ctgcggggga gcgggcgtg ggggctgctg     420
ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcggggcag tgccagccga agtctgccgt tgcccaagag gcccaggcgt     720
ggcgctgccc ctgagccgga gcggacgccc gttgggcagg ggtcctgggc ccacccgggc     780
aggacgcgtg gaccgagtga ccgtggtttc tgtgtggtgt cacctgccag acccgccgaa     840
gaagccacct ctttggaggg tgcgctctct ggcacgcgcc actccaccc atccgtgggc     900
cgccagcacc acgcgggccc cccatccaca tcgcggccac cacgtccctg ggacacgcct     960
tgtccccgg tgtacgccga gaccaagcac ttcctctact cctcaggcga caaggagcag    1020
ctgcggccct ccttcctact cagctctctg aggcccagcc tgactggcgc tcggaggctc    1080
```

```
gtggagacca tctttctggg ttccaggccc tggatgccag ggactcccg caggttgccc      1140 cgcctgcccc agcgctactg gcaaatgcgg cccctgtttc tggagctgct tgggaaccac      1200
gcgcagtgcc cctacggggt gctcctcaag acgcactgcc cgctgcgagc tgcggtcacc      1260
ccagcagccg gtgtctgtgc ccgggagaag ccccagggct ctgtggcggc ccccgaggag      1320
gaggacacag accccgtcg cctggtgcag ctgctccgcc agcacagcag ccctggcag       1380 gtgtacggct tcgtgcgggc ctgcctgcgc cggctggtgc ccccaggcct ctggggctcc      1440
aggcacaacg aacgccgctt cctcaggaac accaagaagt tcatctccct ggggaagcat      1500
gccaagctct cgctgcagga gctgacgtgg aagatgagcg tgcgggactg cgcttggctg      1560
cgcaggagcc caggggttgg ctgtgttccg ccgcagagc accgtctgcg tgaggagatc      1620
ctggccaagt tcctgcactg gctgatgagt gtgtacgtcg tcgagctgct caggtctttc      1680
ttttatgtca cggagaccac gtttcaaaag aacaggctct ttttctaccg gaagagtgtc      1740
tggagcaagt tgcaaagcat tggaatcaga cagcacttga gagggtgca gctgcgggag      1800 ctgtcggaag cagaggtcag gcagcatcgg gaagccaggc ccgccctgct gacgtccaga      1860
ctccgcttca tccccaagcc tgacgggctg cggccgattg tgaacatgga ctacgtcgtg      1920
ggagccagaa cgttccgcag agaaaagagg gccgagcgtc tcacctcgag ggtgaaggca      1980
ctgttcagcg tgctcaacta cgagcgggcg cggcgccccg gcctcctggg cgcctctgtg      2040
ctgggcctgg acgatatcca cagggcctgg cgcaccttcg tgctgcgtgt gcgggcccag      2100
gacccgccgc ctgagctgta ctttgtcaag gtggatgtga cgggcgcgta cgacaccatc      2160
ccccaggaca ggctcacgga ggtcatcgcc agcatcatca aaccccagaa cacgtactgc      2220
gtgcgtcggt atgccgtggt ccagaaggcc gcccatgggc acgtccgcaa ggccttcaag      2280
agccacgtct ctaccttgac agacctccag ccgtacatgc gacagttcgt ggctcacctg      2340
caggagacca gcccgctgag ggatgccgtc gtcatcgagc agagctcctc cctgaatgag      2400
gccagcagtg gcctcttcga cgtcttccta cgcttcatgt gccaccacgc cgtgcgcatc      2460
aggggcaagt cctacgtcca gtgccagggg atcccgcagg gctccatcct ctccacgctg      2520
ctctgcagcc tgtgctacgg cgacatggag aacaagctgt ttgcggggat tcggcgggac      2580
gggctgctcc tgcgttttgg ggatgatttc ttgttggtga cacctcacct cacccacgcg      2640
aaaaccttcc tcaggaccct ggtccgaggt gtccctgagt atggctgcgt ggtgaacttg      2700
cggaagacag tggtgaactt ccctgtagaa gacgaggccc tgggtggcac ggcttttgtt      2760
cagatgccgg cccacggcct attcccctgg tgcggcctgc tgctggatac ccggaccctg      2820
gaggtgcaga gcgactactc cagctatgcc cggacctcca tcagagccag tctcaccttc      2880
aaccgcggct tcaaggctgg gaggaacatg cgtcgcaaac tctttggggt cttgcggctg      2940
aagtgtcaca gcctgtttct ggatttgcag gtgaacagcc tccagacggt gtgcaccaac      3000
atctacaaga tcctcctgct gcaggcgtac aggtttcacg catgtgtgct gcagctccca      3060
tttcatcagc aagtttggaa gaaccccaca tttttcctgc gcgtcatctc tgacacggcc      3120
tccctctgct actccatcct gaaagccaag aacgcaggga tgtcgctggg ggccaagggc      3180
gccgccggcc ctctgccctc cgaggccgtg cagtggctgt gccaccaagc attcctgctc      3240
aagctgactc gacaccgtgt cacctacgtg ccactcctgg ggtcactcag acagcccag      3300 acgcagctga tcggaagct cccggggacg acgctgactg ccctggaggc cgcagccaac      3360
ccggcactgc cctcagactt caagaccatc ctggactga                            3399
```

```
<210> SEQ ID NO 12
<211> LENGTH: 1132
<212> TYPE: PRT
<213> ORGANISM: Homo Sapiens

<400> SEQUENCE: 12

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
```

```
              385                 390                 395                 400
Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
                530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro Pro
                690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815
```

```
Ala Val Arg Ile Arg Gly Lys Ser Tyr Val Gln Cys Gln Gly Ile Pro
            820                 825                 830

Gln Gly Ser Ile Leu Ser Thr Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
            930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln Gln
            1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
            1075                1080                1085

Tyr Val Pro Leu Leu Gly Ser Leu Arg Thr Ala Gln Thr Gln Leu Ser
            1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130

<210> SEQ ID NO 13
<211> LENGTH: 309
<212> TYPE: DNA
<213> ORGANISM: E. coli

<400> SEQUENCE: 13
gcccctcaga gcatcaccga gctgtgcagc gagtaccgga acacccagat ttacaccatc      60
aacgacaaga tcctgagcta caccgagtct atggccggca agcgggagat ggtgatcatc     120
accttcaaga gcggcgccac ctttcaggtg gaagtgcctg cagccagca catcgacagc      180 cagaagaagg ccatcgagcg gatgaaggac accctgcgga tcacctacct gaccgagacc     240
aagatcgaca agctgtgtgt gtggaacaac aagacccccca cagcatcgc cgccatctct    300 atggagaac                                                             309
```

```
<210> SEQ ID NO 14
<211> LENGTH: 109
<212> TYPE: PRT
<213> ORGANISM: E. coli

<400> SEQUENCE: 14

Ala Pro Gln Ser Ile Thr Glu Leu Cys Ser Glu Tyr Arg Asn Thr Gln
  1               5                  10                  15

Ile Tyr Thr Ile Asn Asp Lys Ile Leu Ser Tyr Thr Glu Ser Met Ala
             20                  25                  30

Gly Lys Arg Glu Met Val Ile Ile Thr Phe Lys Ser Gly Ala Thr Phe
         35                  40                  45

Gln Val Glu Val Pro Gly Ser Gln His Ile Asp Ser Gln Lys Lys Ala
     50                  55                  60

Ile Glu Arg Met Lys Asp Thr Leu Arg Ile Thr Tyr Leu Thr Glu Thr
 65                  70                  75                  80

Lys Ile Asp Lys Leu Cys Val Trp Asn Asn Lys Thr Pro Asn Ser Ile
                 85                  90                  95

Ala Ala Ile Ser Met Glu Asn Ser Glu Gln Ile Asp Asn
            100                 105

<210> SEQ ID NO 15
<211> LENGTH: 40
<212> TYPE: DNA
<213> ORGANISM: Artificial Sequence
<220> FEATURE:
<223> OTHER INFORMATION: PCR Primer

<400> SEQUENCE: 15
gatctgatga tatcgccacc atgaccagag cccccagatg                             40

<210> SEQ ID NO 16
<211> LENGTH: 36
<212> TYPE: DNA
<213> ORGANISM: Artificial Sequence
<220> FEATURE:
<223> OTHER INFORMATION: PCR Primer

<400> SEQUENCE: 16
aggggggatc cgcacacctg gtaggcgcag ctgggg                                 36

<210> SEQ ID NO 17
<211> LENGTH: 37
<212> TYPE: DNA
<213> ORGANISM: Artificial Sequence
<220> FEATURE:
<223> OTHER INFORMATION: PCR Primer

<400> SEQUENCE: 17
ctgtactttg tcaaggtggc tatcacgggc gcgtacg                                37

<210> SEQ ID NO 18
<211> LENGTH: 15
<212> TYPE: PRT
<213> ORGANISM: Artificial Sequence
<220> FEATURE:
<223> OTHER INFORMATION: Peptide

<400> SEQUENCE: 18

Leu Val Pro Pro Ser Cys Ala Tyr Gln Val Cys Gly Ser Pro Leu
  1               5                  10                  15

<210> SEQ ID NO 19
```

-continued

```
<211> LENGTH: 15
<212> TYPE: PRT
<213> ORGANISM: Artificial Sequence
<220> FEATURE:
<223> OTHER INFORMATION: Peptide

<400> SEQUENCE: 19

Ser Cys Ala Tyr Gln Val Cys Gly Ser Pro Leu Tyr Gln Ile Cys
 1               5                  10                  15

<210> SEQ ID NO 20
<211> LENGTH: 9
<212> TYPE: PRT
<213> ORGANISM: Artificial Sequence
<220> FEATURE:
<223> OTHER INFORMATION: Peptide

<400> SEQUENCE: 20

Ala Tyr Gln Val Cys Gly Ser Pro Leu
 1               5

<210> SEQ ID NO 21
<211> LENGTH: 8
<212> TYPE: PRT
<213> ORGANISM: Artificial Sequence
<220> FEATURE:
<223> OTHER INFORMATION: Peptide

<400> SEQUENCE: 21

Val Gly Arg Asn Phe Thr Asn Leu
 1               5

<210> SEQ ID NO 22
<211> LENGTH: 8
<212> TYPE: PRT
<213> ORGANISM: Artificial Sequence
<220> FEATURE:
<223> OTHER INFORMATION: Peptide

<400> SEQUENCE: 22

Ser Leu Gly Lys Tyr Gly Lys Leu
 1               5

<210> SEQ ID NO 23
<211> LENGTH: 9
<212> TYPE: PRT
<213> ORGANISM: Artificial Sequence
<220> FEATURE:
<223> OTHER INFORMATION: Peptide

<400> SEQUENCE: 23

Arg Leu Val Asp Asp Phe Leu Leu Val
 1               5
```